(12) United States Patent
Deb et al.

(10) Patent No.: US 10,724,006 B2
(45) Date of Patent: Jul. 28, 2020

(54) BUFFERS FOR STABILIZATION OF LENTIVIRAL PREPARATIONS

(71) Applicants: Novartis AG, Basel (CH); The Trustees of the University of Pennsylvania, Philadelphia, PA (US)

(72) Inventors: Amitabha Deb, Cambridge, MA (US); Eugene Nebelitsky, Norwood, MA (US); Vladimir Slepushkin, Everett, MA (US)

(73) Assignees: Novartis AG, Basel (CH); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/777,290

(22) PCT Filed: Nov. 18, 2016

(86) PCT No.: PCT/US2016/062871
§ 371 (c)(1),
(2) Date: May 18, 2018

(87) PCT Pub. No.: WO2017/087861
PCT Pub. Date: May 26, 2017

(65) Prior Publication Data
US 2018/0363002 A1    Dec. 20, 2018

Related U.S. Application Data

(60) Provisional application No. 62/257,444, filed on Nov. 19, 2015.

(51) Int. Cl.
| | | |
|---|---|---|
| C12N 15/113 | (2010.01) |
| C07H 21/04 | (2006.01) |
| C07H 21/02 | (2006.01) |
| C12N 15/11 | (2006.01) |
| A61K 31/713 | (2006.01) |
| C12N 7/00 | (2006.01) |

(52) U.S. Cl.
CPC ...... *C12N 7/00* (2013.01); *C12N 2740/15051* (2013.01); *C12N 2740/16051* (2013.01)

(58) Field of Classification Search
CPC ...... C12N 2310/321; C12N 2310/3521; C12N 2310/14; C12N 2310/322; A61K 2300/00
See application file for complete search history.

(56) References Cited

U.S. PATENT DOCUMENTS

2015/0056696 A1    2/2015    Fan et al.

FOREIGN PATENT DOCUMENTS

| WO | WO2007149343 | * | 12/2007 |
| WO | WO2015028969 | * | 3/2015 |
| WO | WO-2015/097650 A1 | | 7/2015 |

OTHER PUBLICATIONS

Carmo et al., "Stabilization of gammaretroviral and lentiviral vectors: from production to gene transfer," J Gene Med. 11(8):670-8 (2009).
Cribbs et al., "Simplified production and concentration of lentiviral vectors to achieve high transduction in primary human T cells," BMC Biotechnol. 13:98 (2013).
International Search Report and Written Opinion dated Apr. 4, 2017 for International Application No. PCT/US2016/062871, Deb et al., "Buffers for Stabilization of Lentiviral Preparations," filed Nov. 18, 2016 (24 pages).
Kutner et al., "Production, concentration and titration of pseudotyped HIV-1-based lentiviral vectors," Nat Protoc. 4(4):495-505 (2009).
Salmon et al., "Production and titration of lentiviral vectors," Curr Protoc Human Genetics. Chapter 4:Unit 12.10 (2007).
Schweizer et al., "Large-scale production means for the manufacturing of lentiviral vectors," Curr Gene Ther. 10(6):474-86 (2010).
Tiscornia et al., "Production and purification of lentiviral vectors," Nat Protoc. 1(1):241-5 (2006).
International Preliminary Report on Patentability dated May 31, 2018 for International Application No. PCT/US2016/062871, Deb et al., "Buffers for Stabilization of Lentiviral Preparations," filed Nov. 18, 2016 (14 pages).
Barde et al., Chapter 4: Unit 4.21: Production and Titration of Lentiviral Vectors. *Current Protocols in Neuroscience.* John Wiley & Sons, Inc., Supplement 53(1):4.21.1-4.21.23 (2010) (23 pages).
Official Notification and Search Report for Russian Patent Application No. 2018122106, dated Apr. 3, 2020 (13 pages).
Supotnitskiy, "Genotherapeutic Vector Systems Based on Viruses," Biopharmaceuticals. 3:15-26 (2011) (12 pages).

* cited by examiner

*Primary Examiner* — Barry A Chestnut
(74) *Attorney, Agent, or Firm* — Clark & Elbing LLP; Susan M. Michaud

(57) ABSTRACT

The invention provides lentiviral preparations containing a sulfonic acid buffer, such as 1,4-piperazinediethanesulfonic acid (PIPES), 2-(N-morpholino)ethanesulfonic acid (MES), and 3-morpholinopropane-1-sulfonic acid (MOPS), a sodium citrate buffer, or a phosphate buffer. The invention additionally encompasses methods of lentiviral purification as well as methods of transducing human cells.

23 Claims, 43 Drawing Sheets

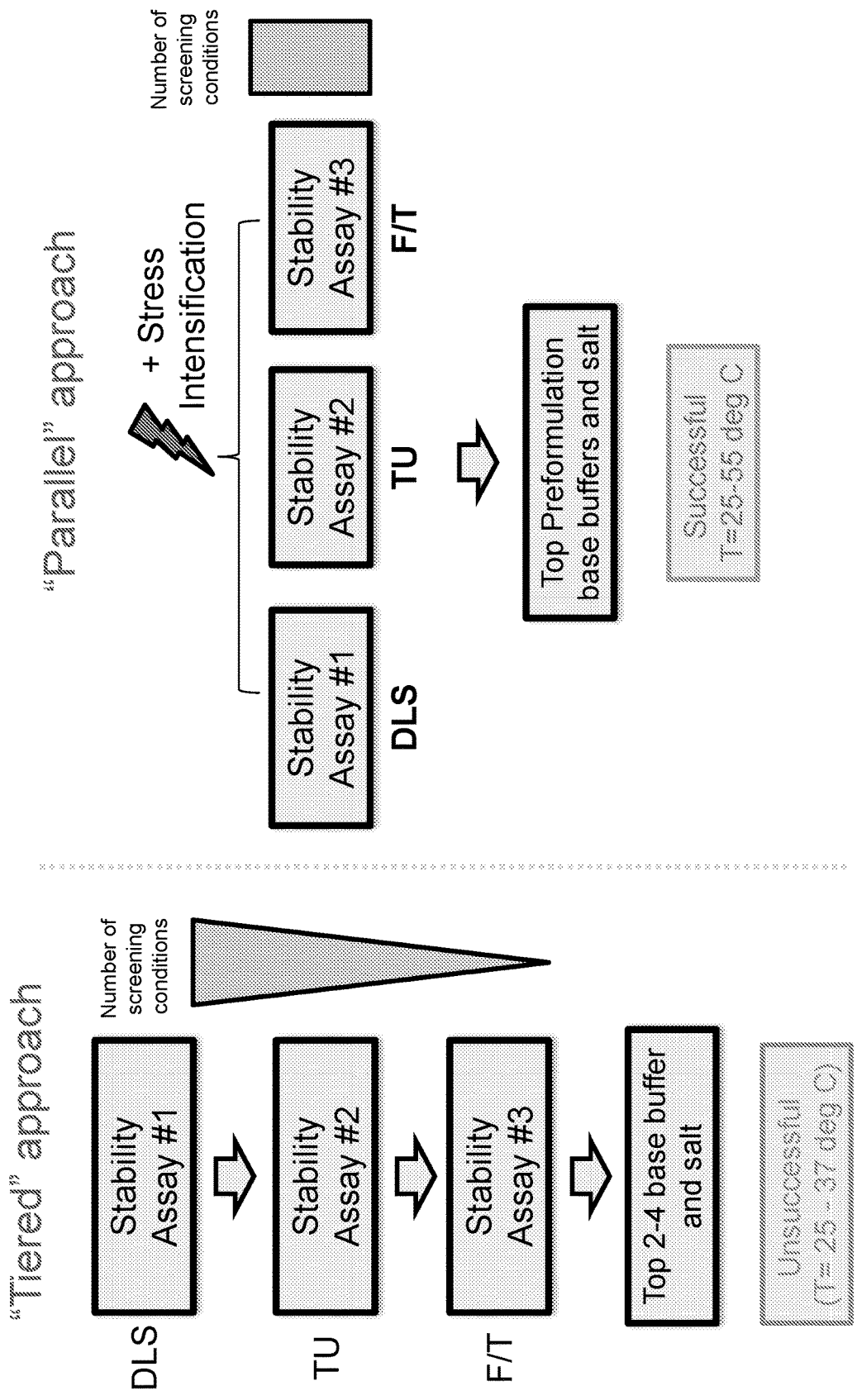
Fig. 1: Strategy and screening methodology to identify stabilizing buffers

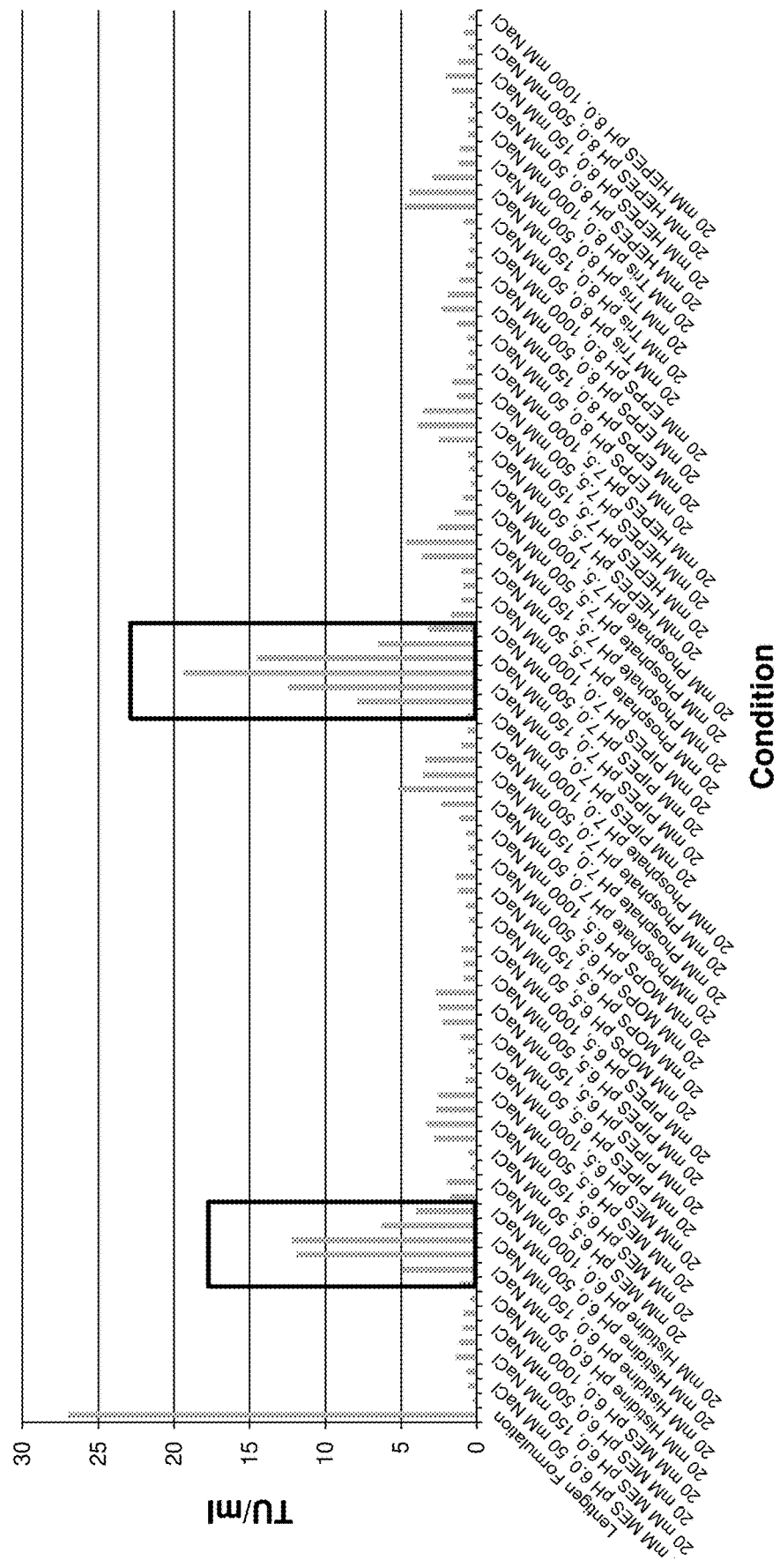
Fig. 2: Stability of commercially available lentiviral vector in buffers

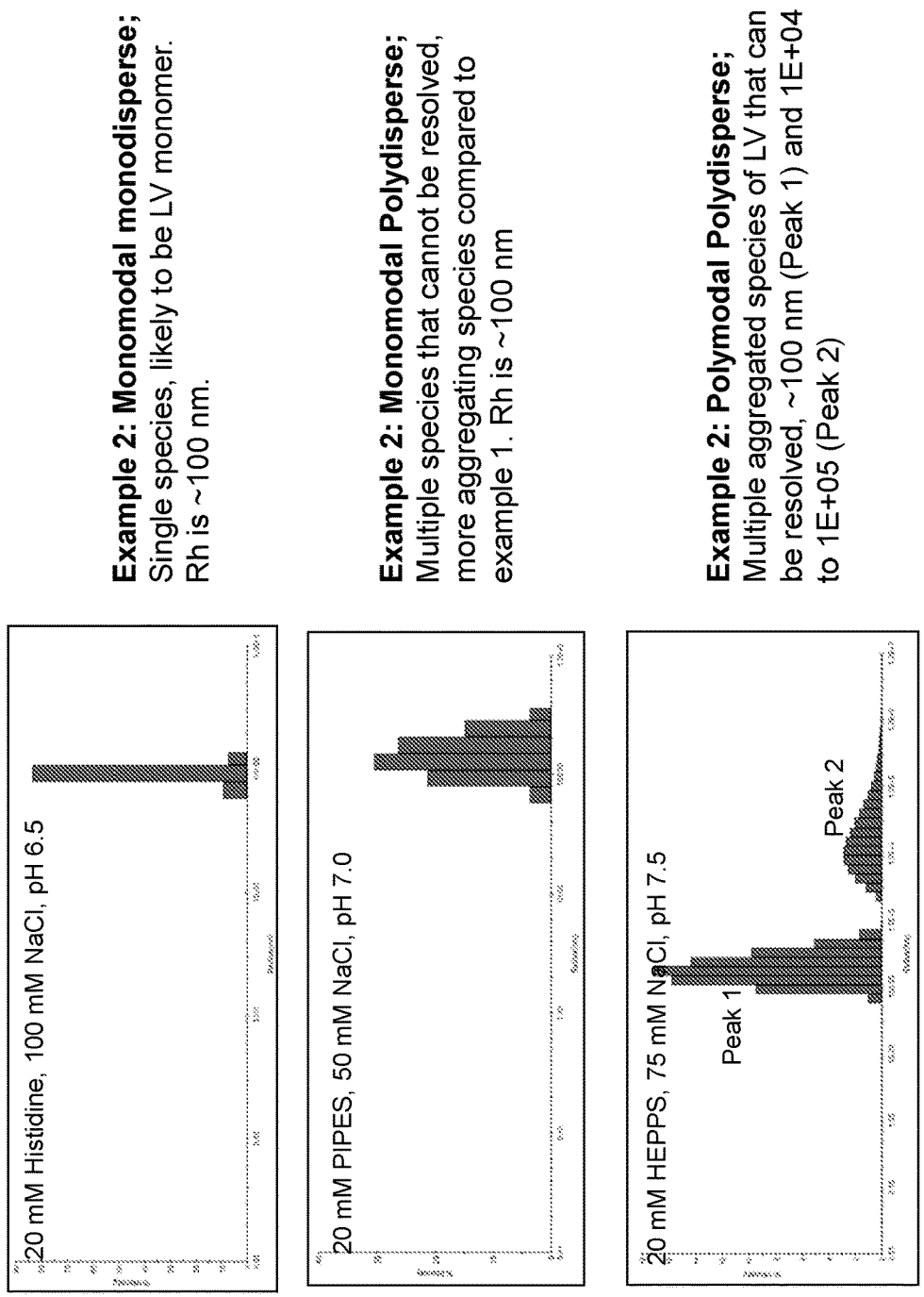
Fig. 3: Examples of size interpretations from DLS results

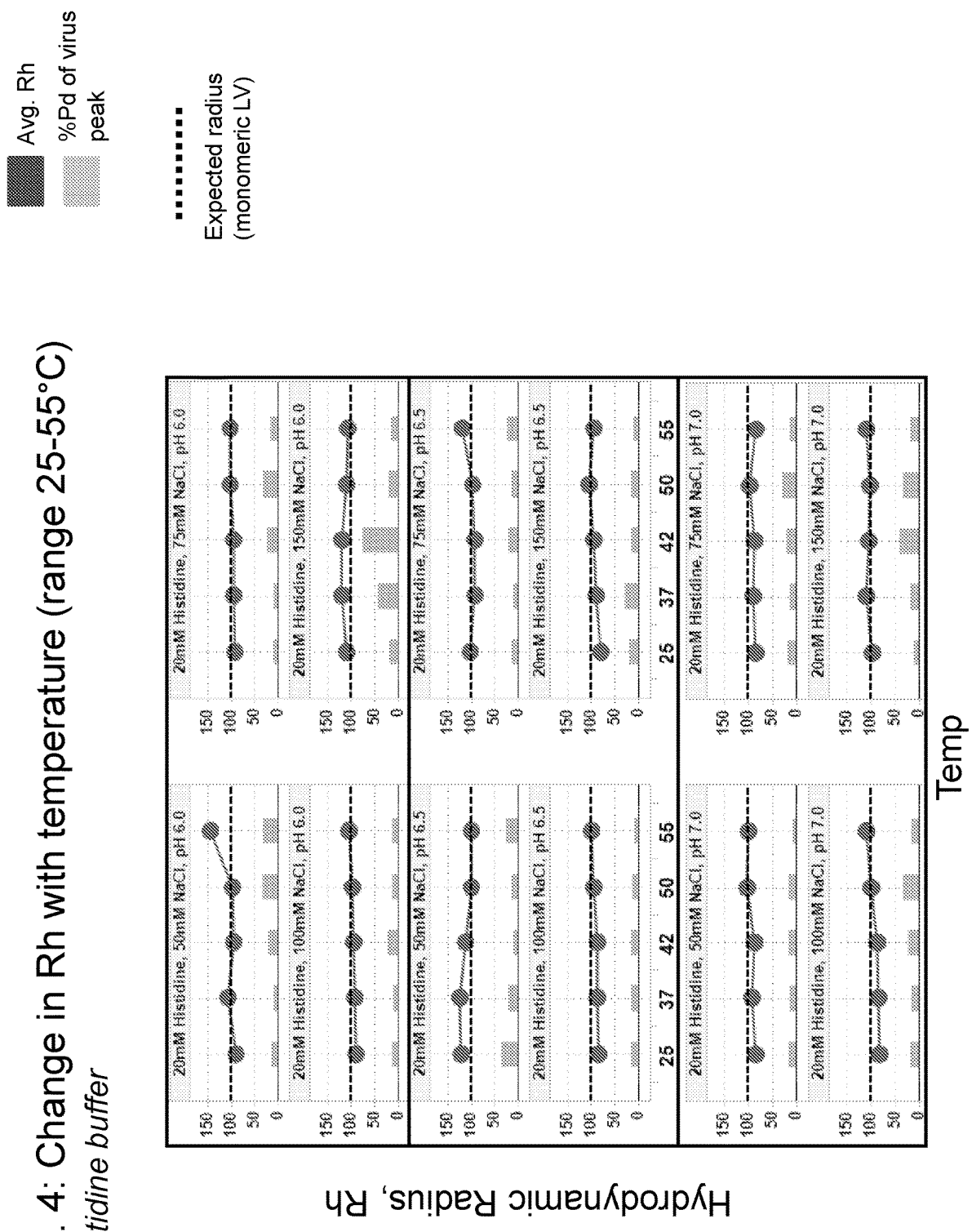
Fig. 4: Change in Rh with temperature (range 25-55°C)
*Histidine buffer*

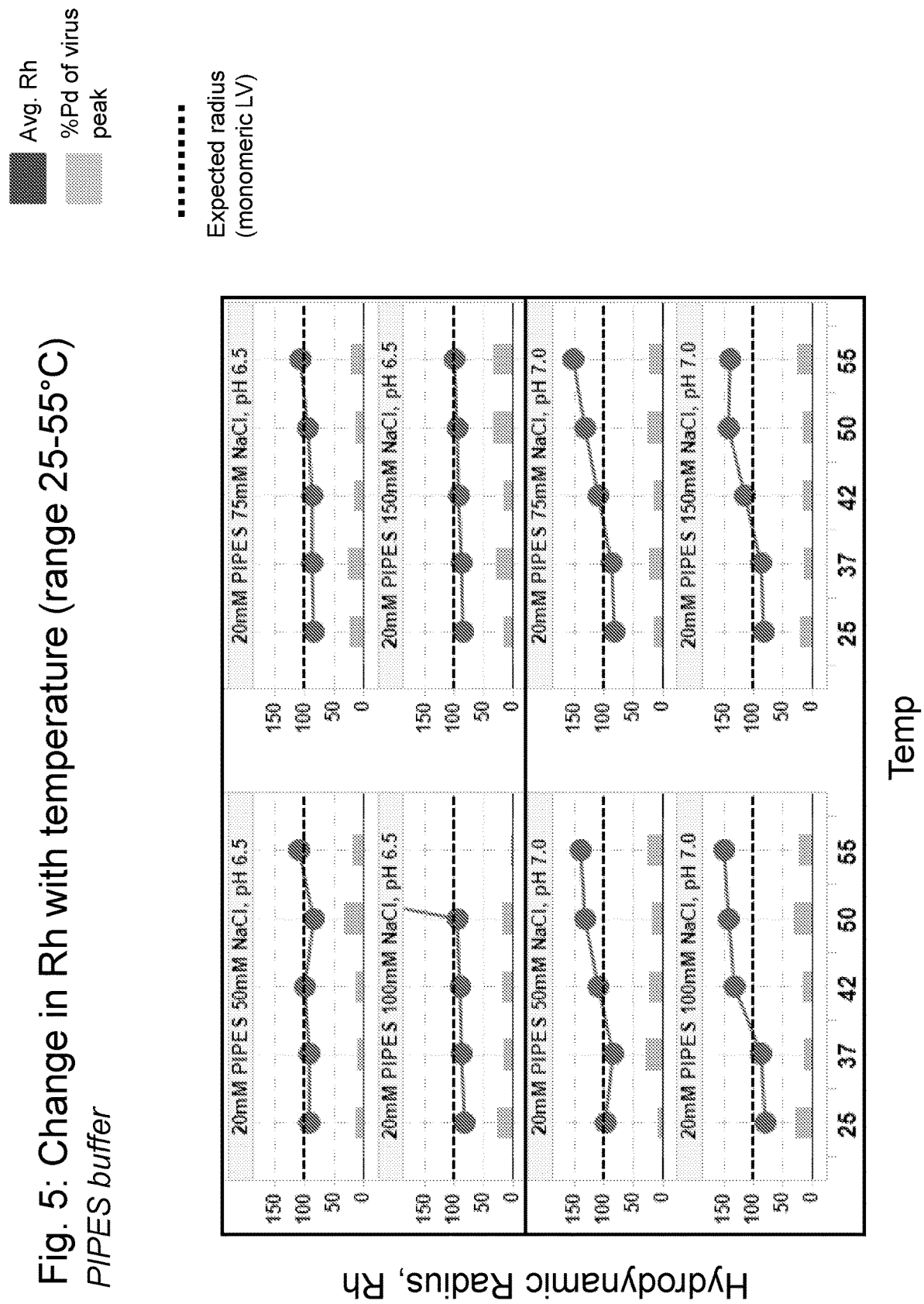
Fig. 5: Change in Rh with temperature (range 25-55°C)
*PIPES buffer*

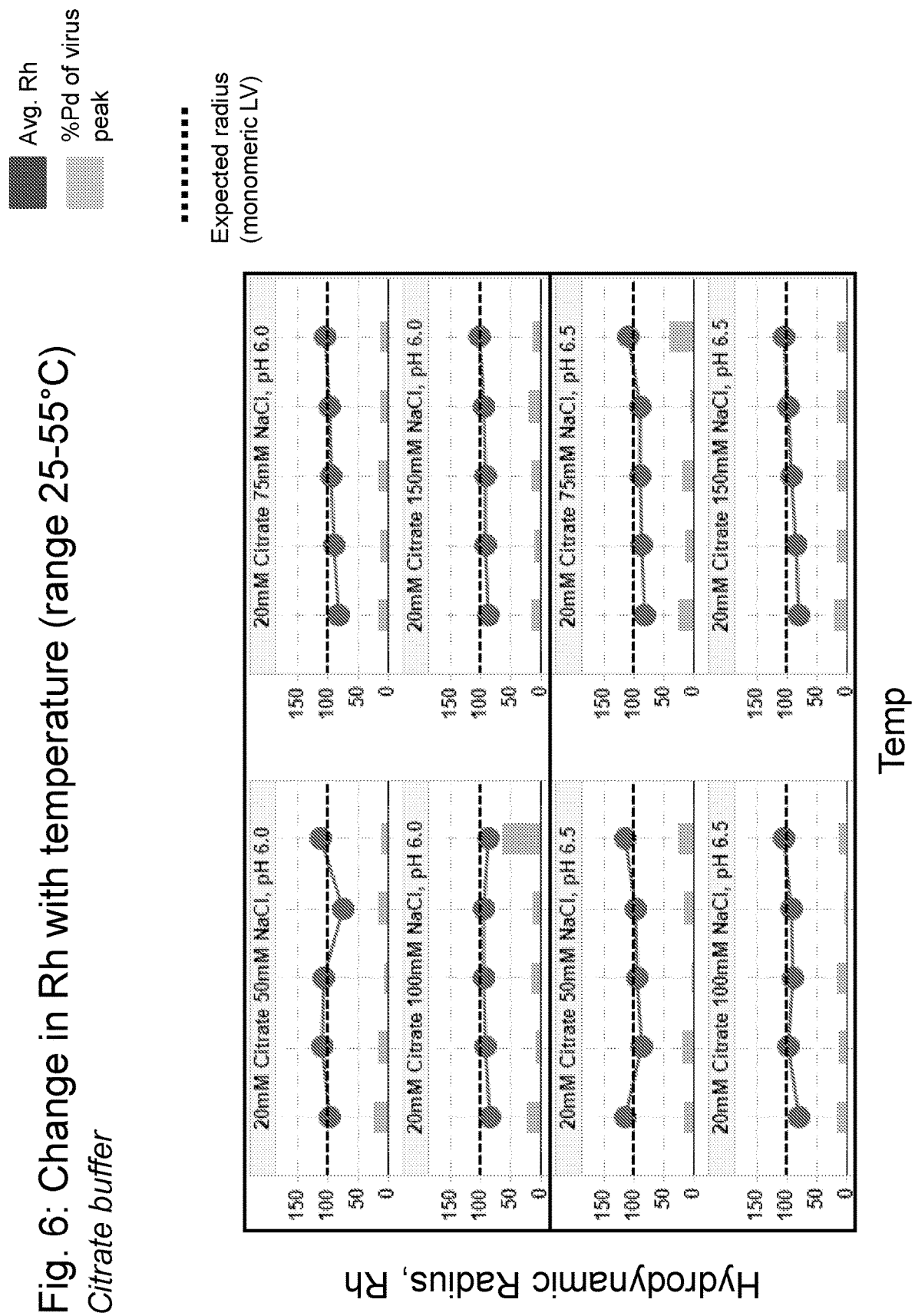
Fig. 6: Change in Rh with temperature (range 25-55°C)
*Citrate buffer*

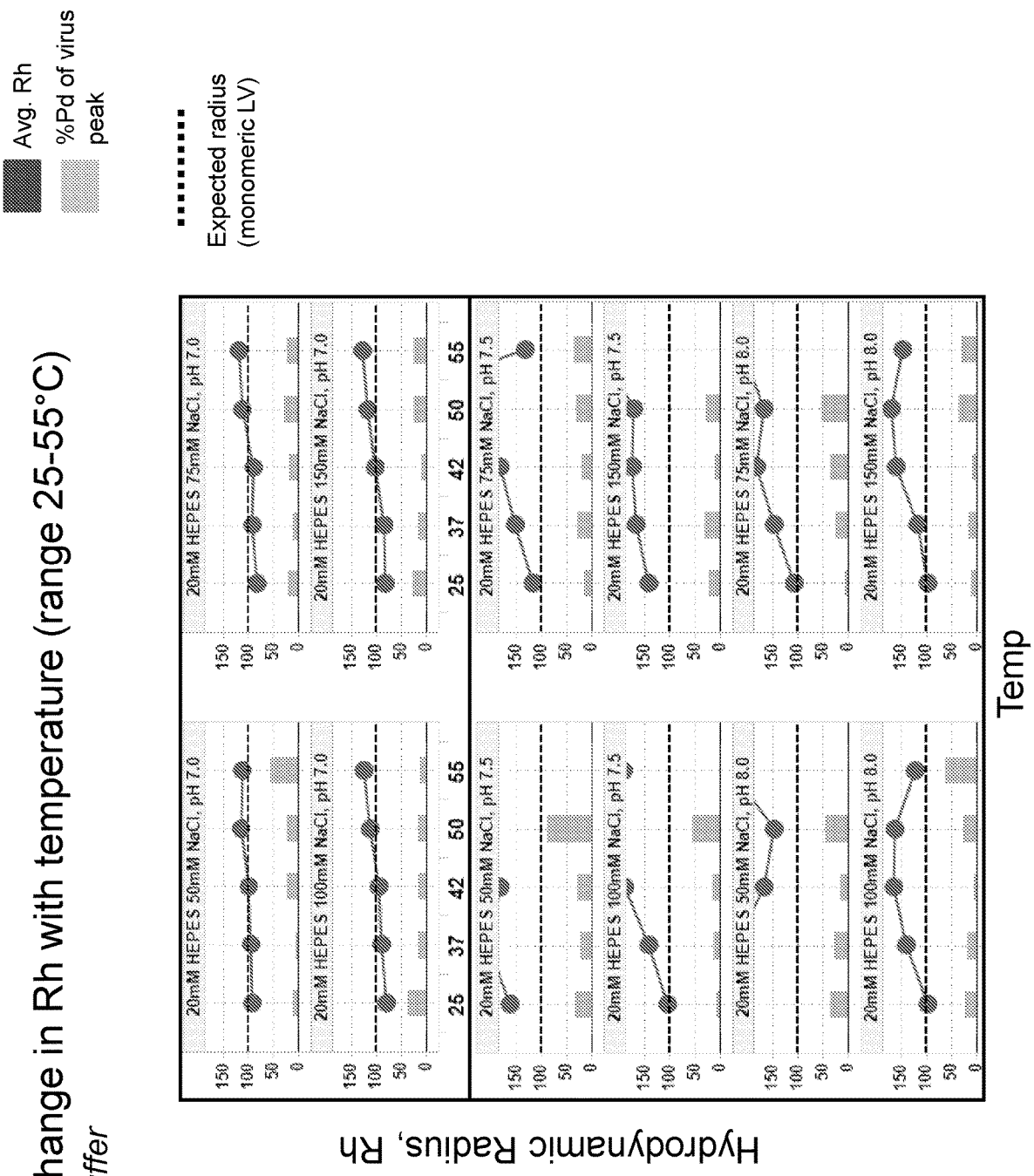
Fig. 7: Change in Rh with temperature (range 25-55°C)
*HEPES buffer*

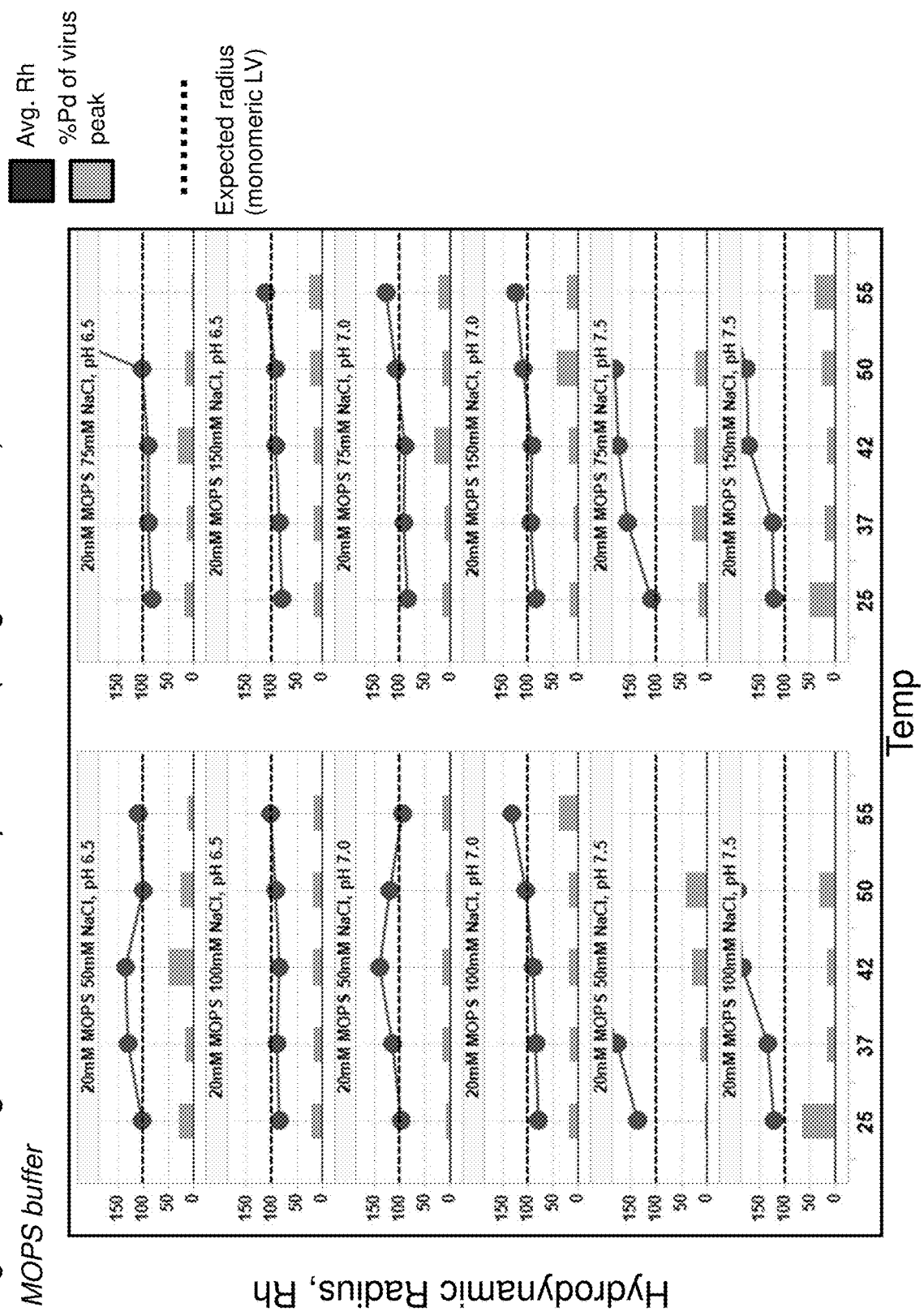
Fig. 8: Change in Rh with temperature (range 25-55°C)
MOPS buffer

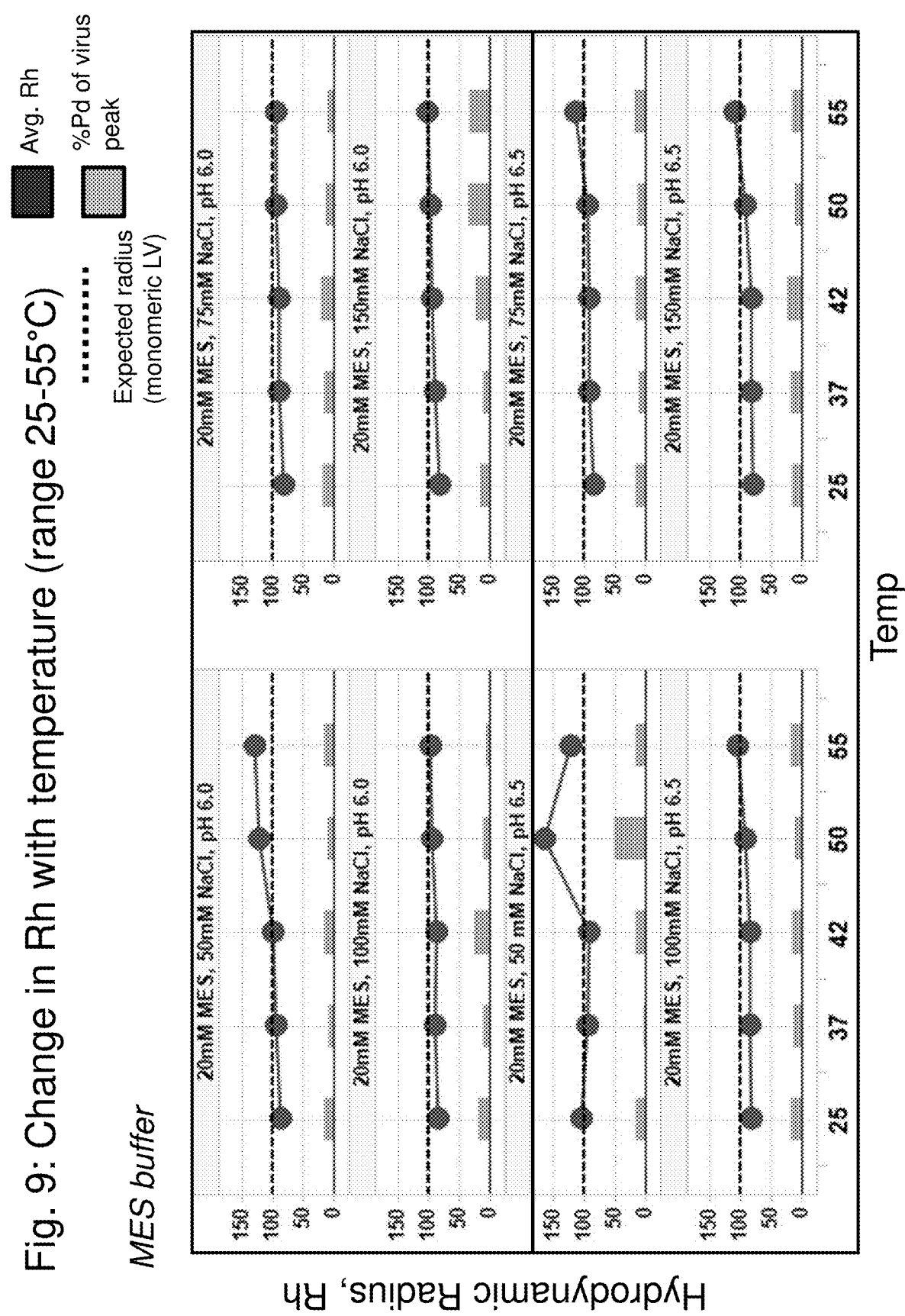
Fig. 9: Change in Rh with temperature (range 25-55°C)
*MES buffer*

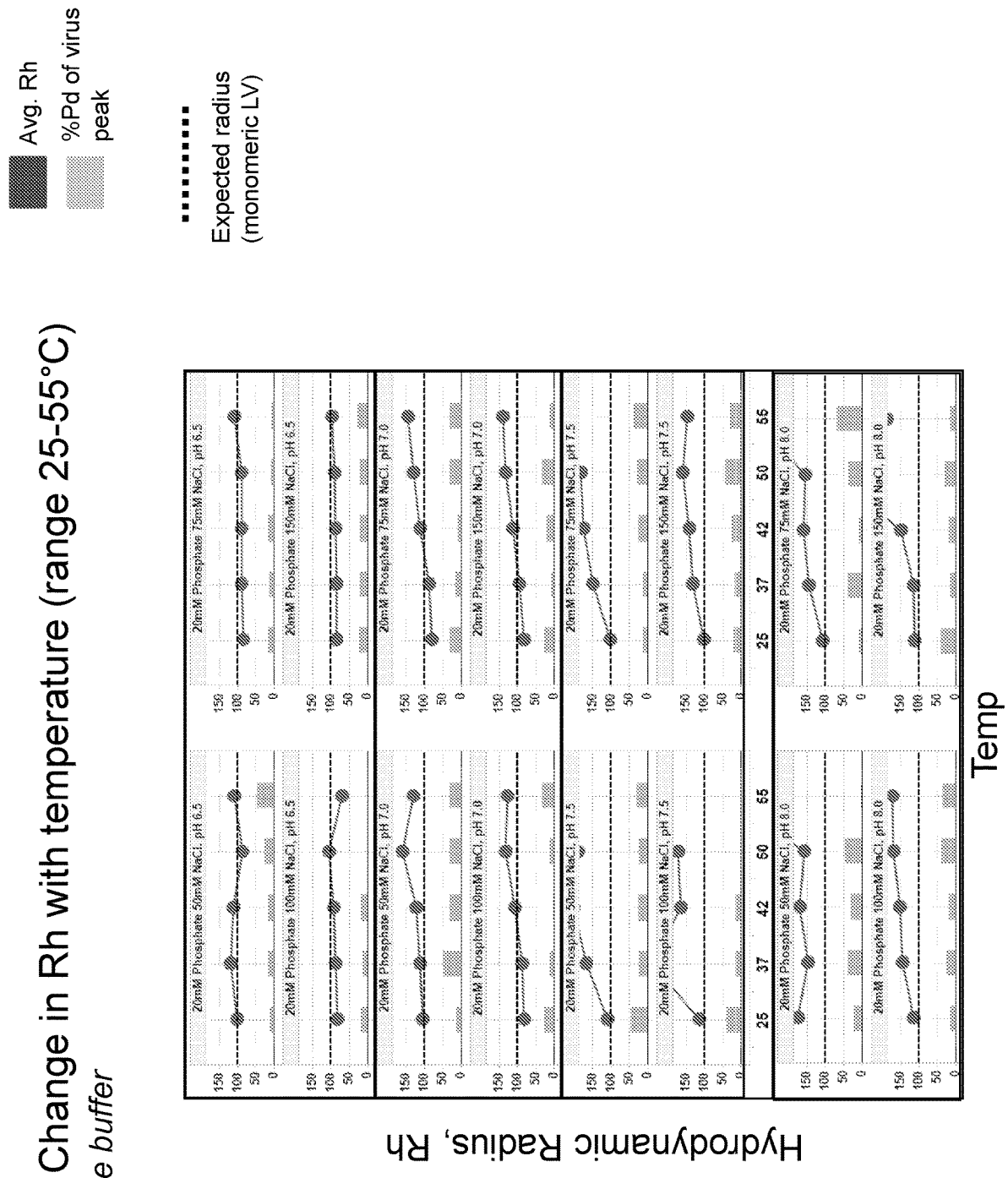
Fig. 10: Change in Rh with temperature (range 25-55°C)
*Phosphate buffer*

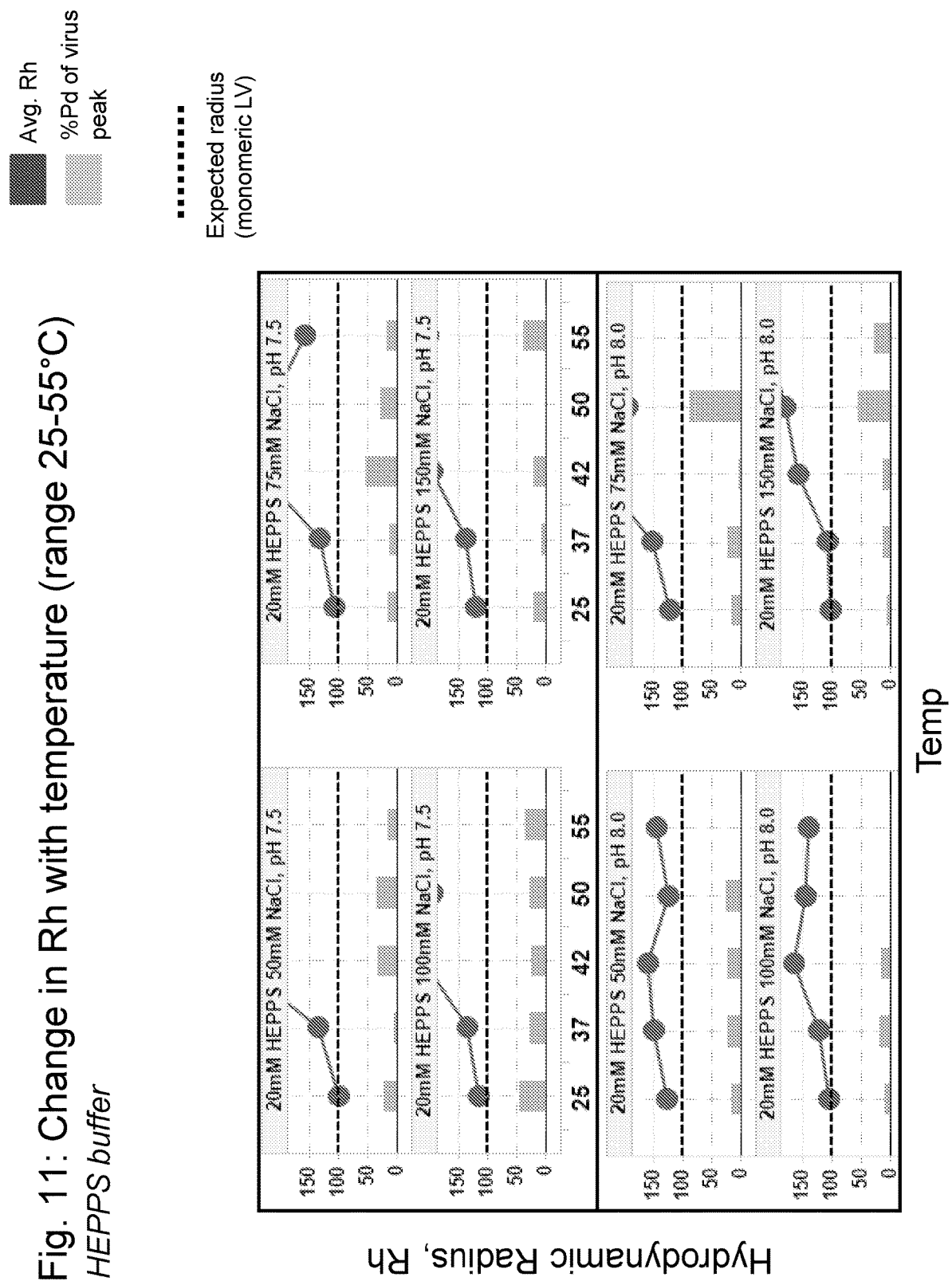
Fig. 11: Change in Rh with temperature (range 25-55°C)
*HEPPS buffer*

Fig. 12: Change in Rh with temperature (range 25-55°C)
*Tris buffer*

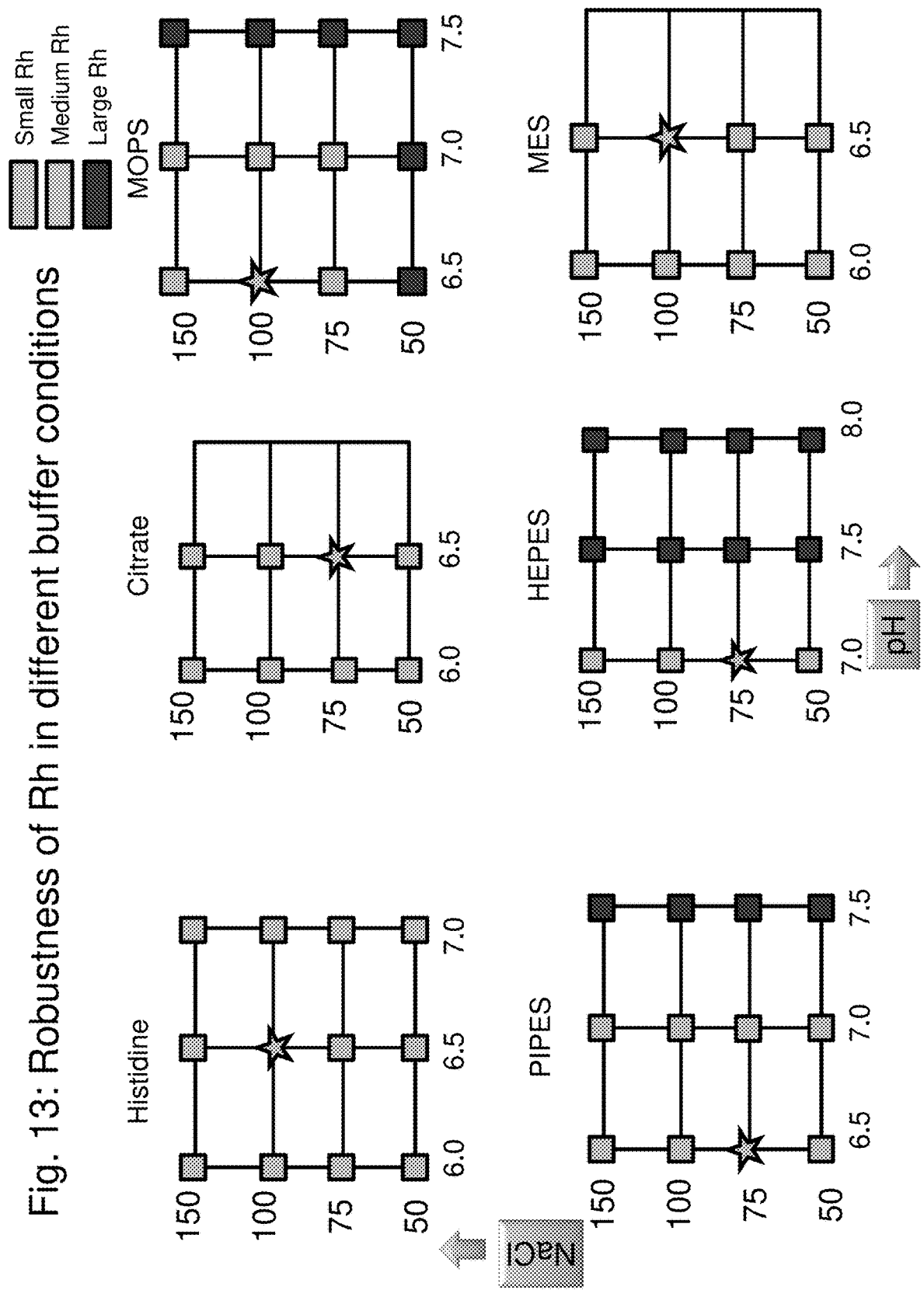
Fig. 13: Robustness of Rh in different buffer conditions

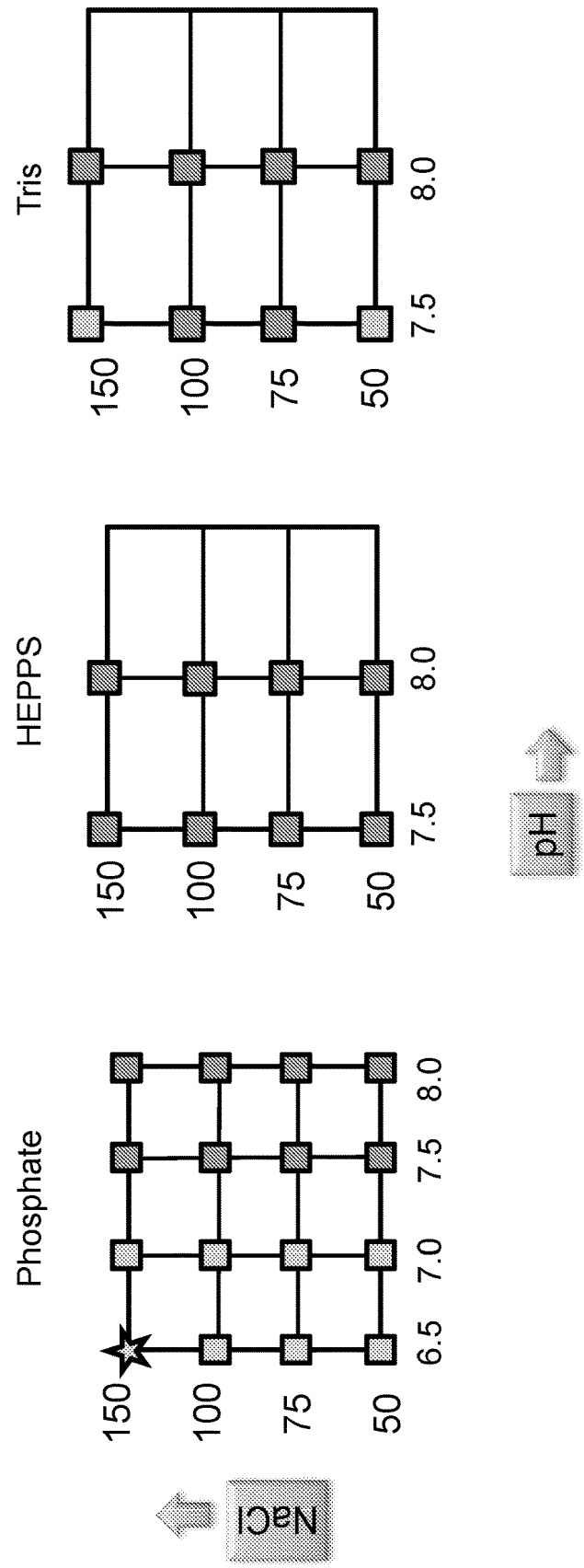
Fig. 14: Robustness of Rh in different buffer conditions

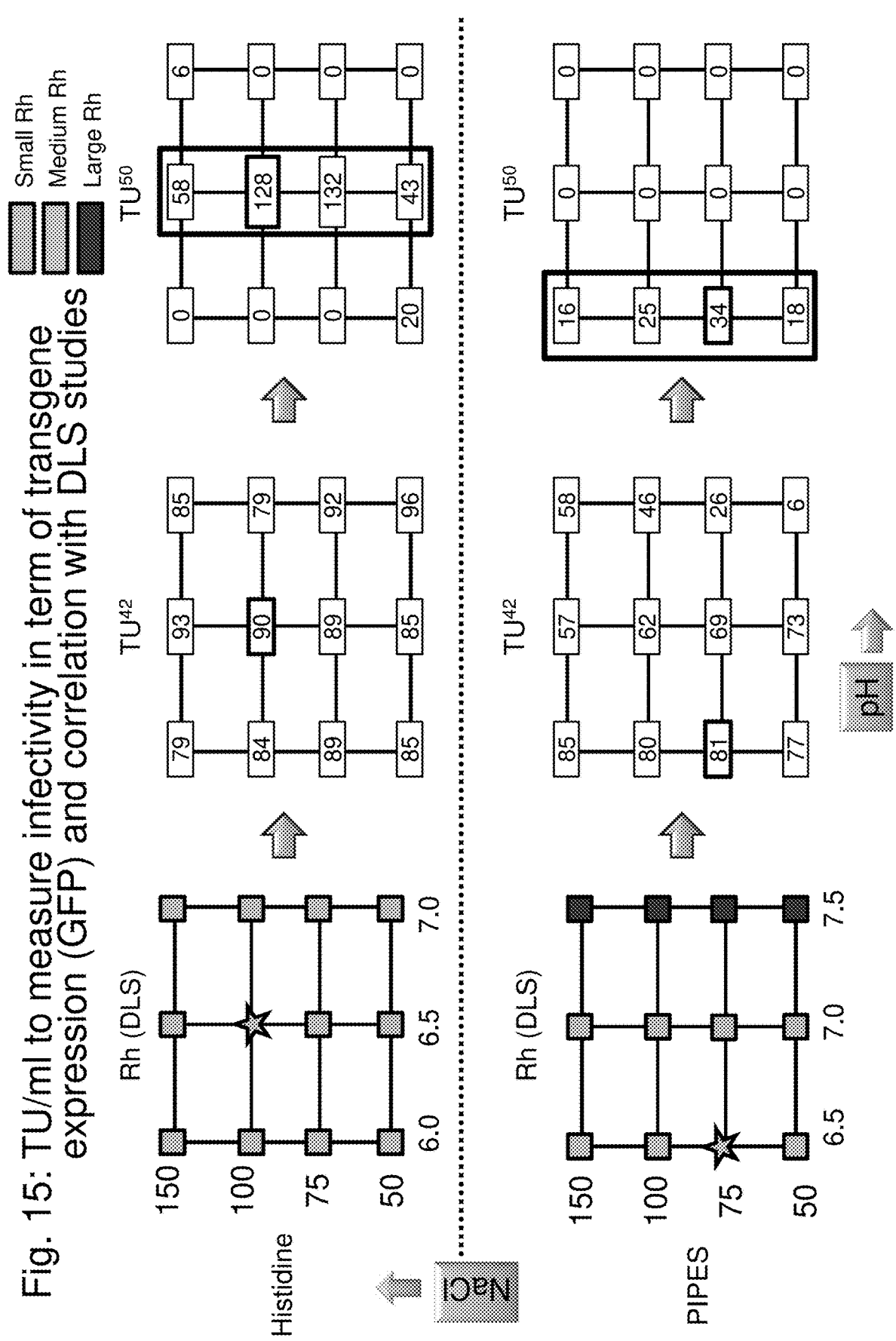
Fig. 15: TU/ml to measure infectivity in term of transgene expression (GFP) and correlation with DLS studies

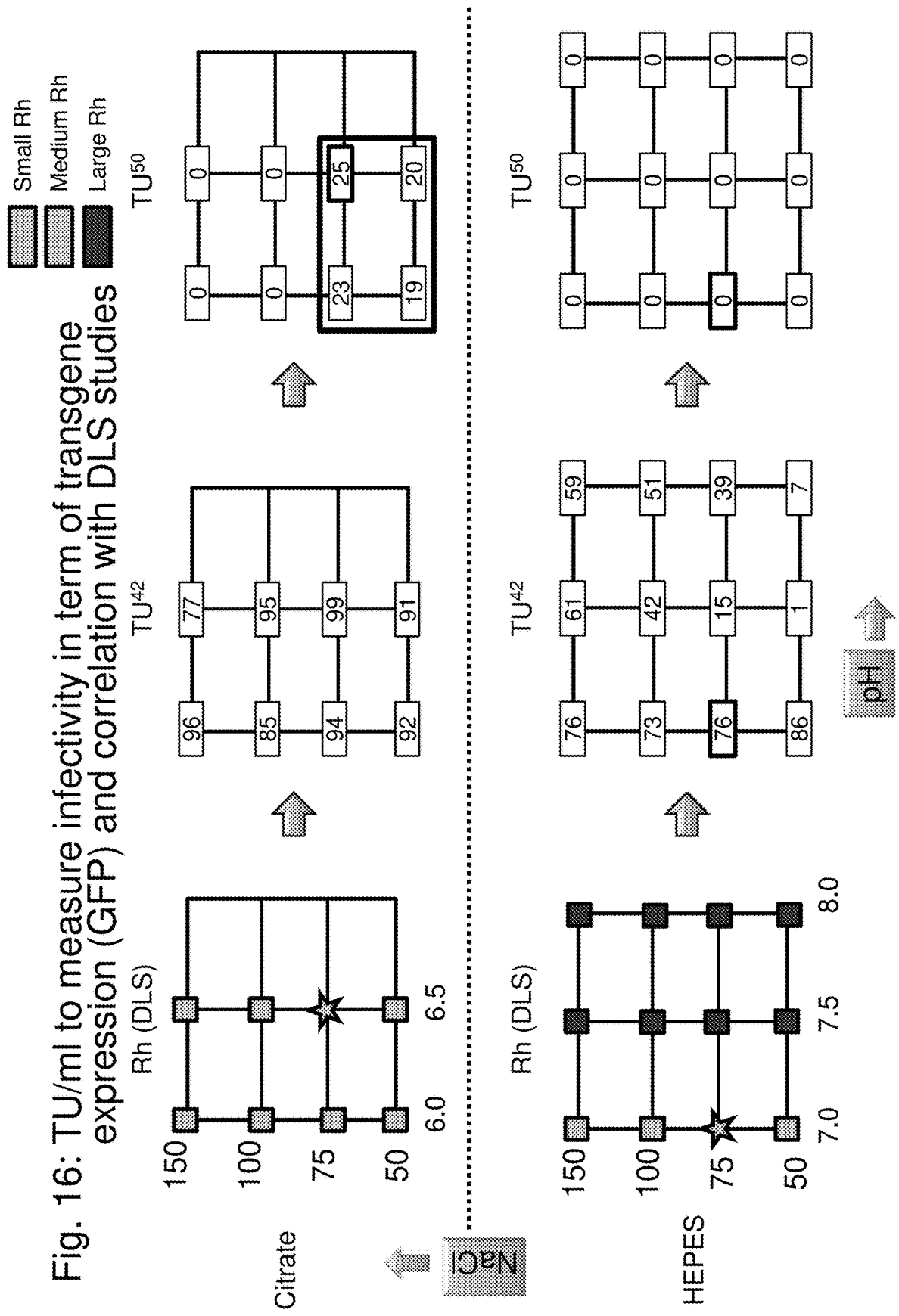
Fig. 16: TU/ml to measure infectivity in term of transgene expression (GFP) and correlation with DLS studies

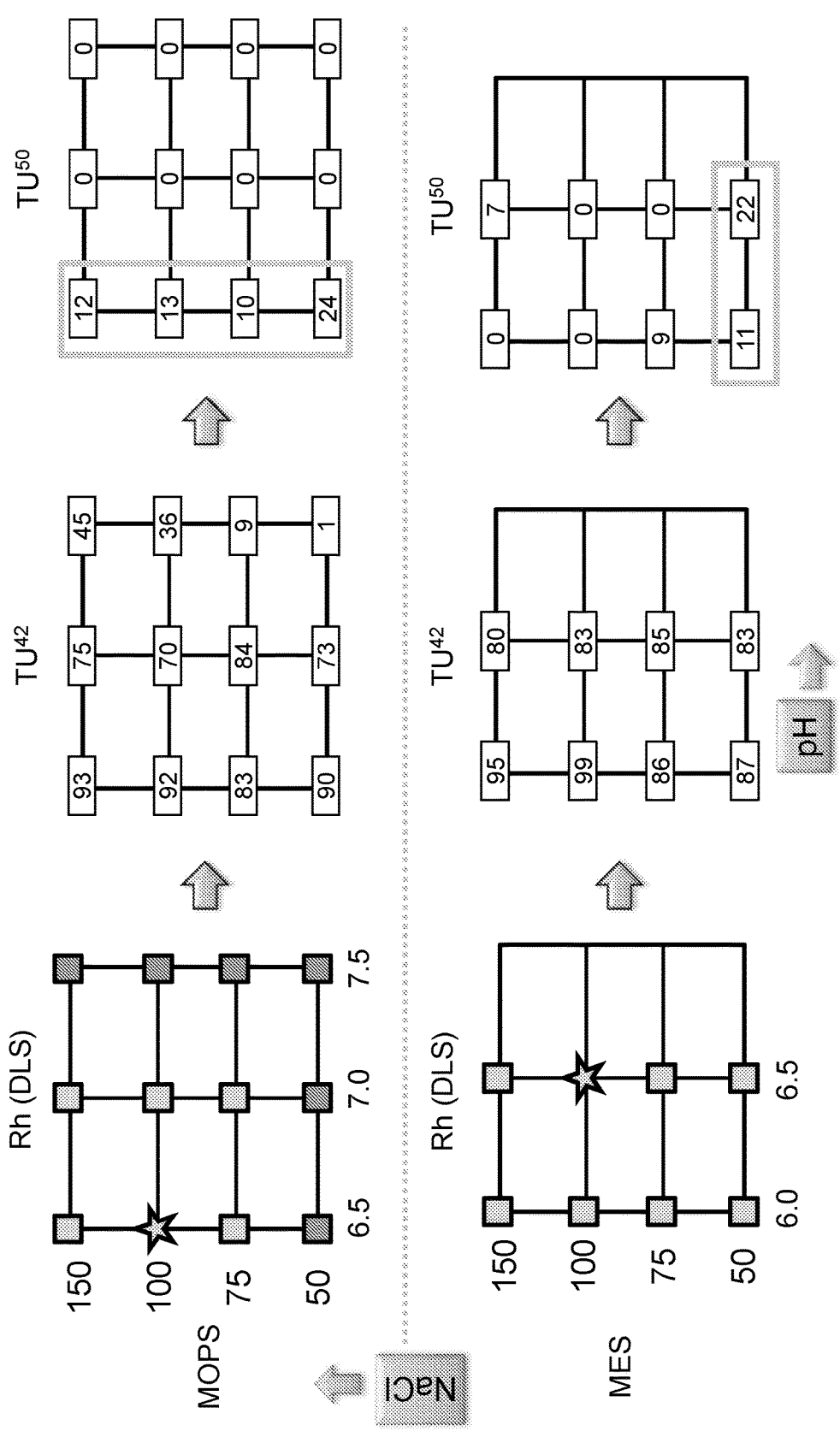
Fig. 17: TU/ml to measure infectivity in term of transgene expression (GFP) and correlation with DLS studies

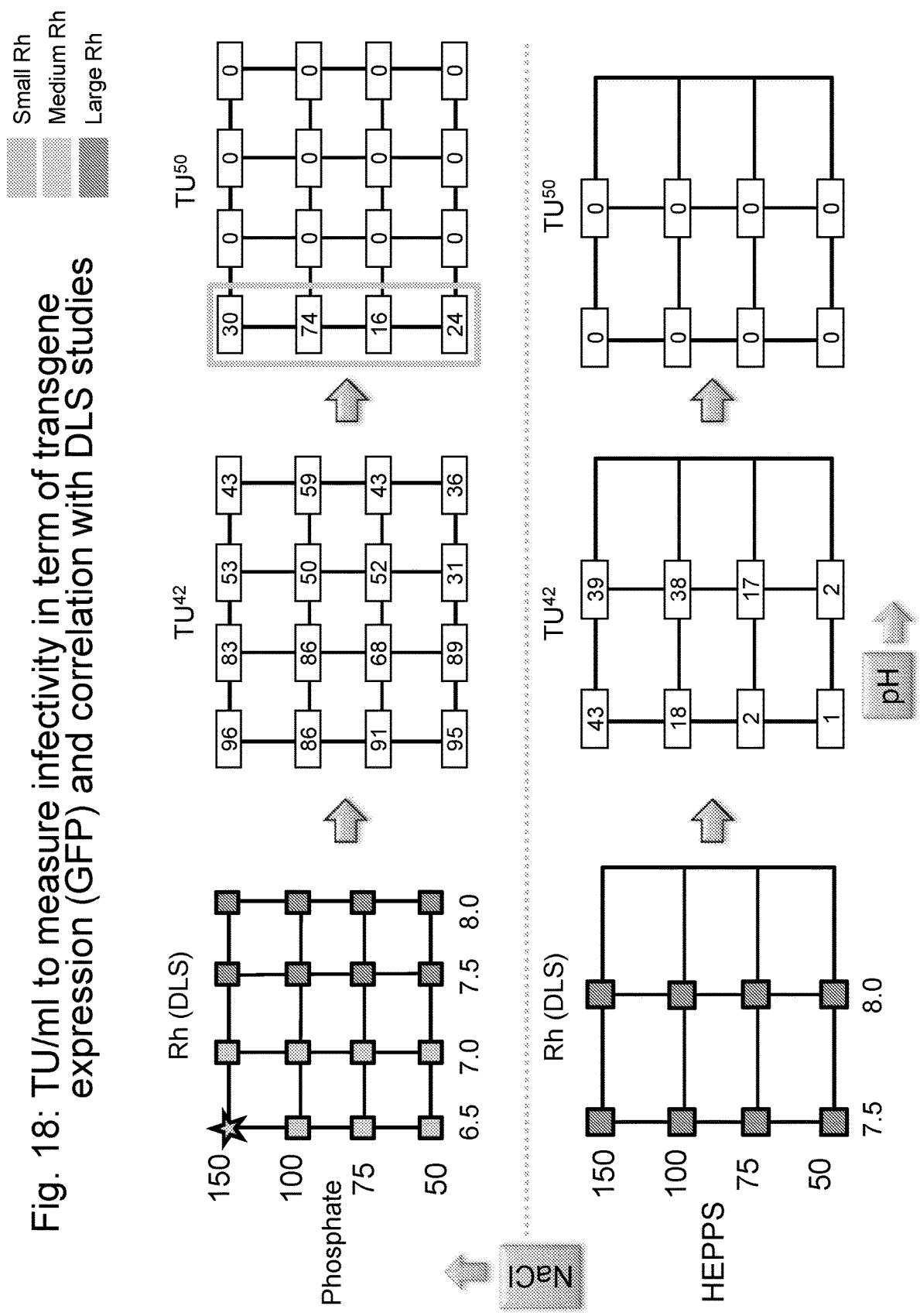
Fig. 18: TU/ml to measure infectivity in term of transgene expression (GFP) and correlation with DLS studies

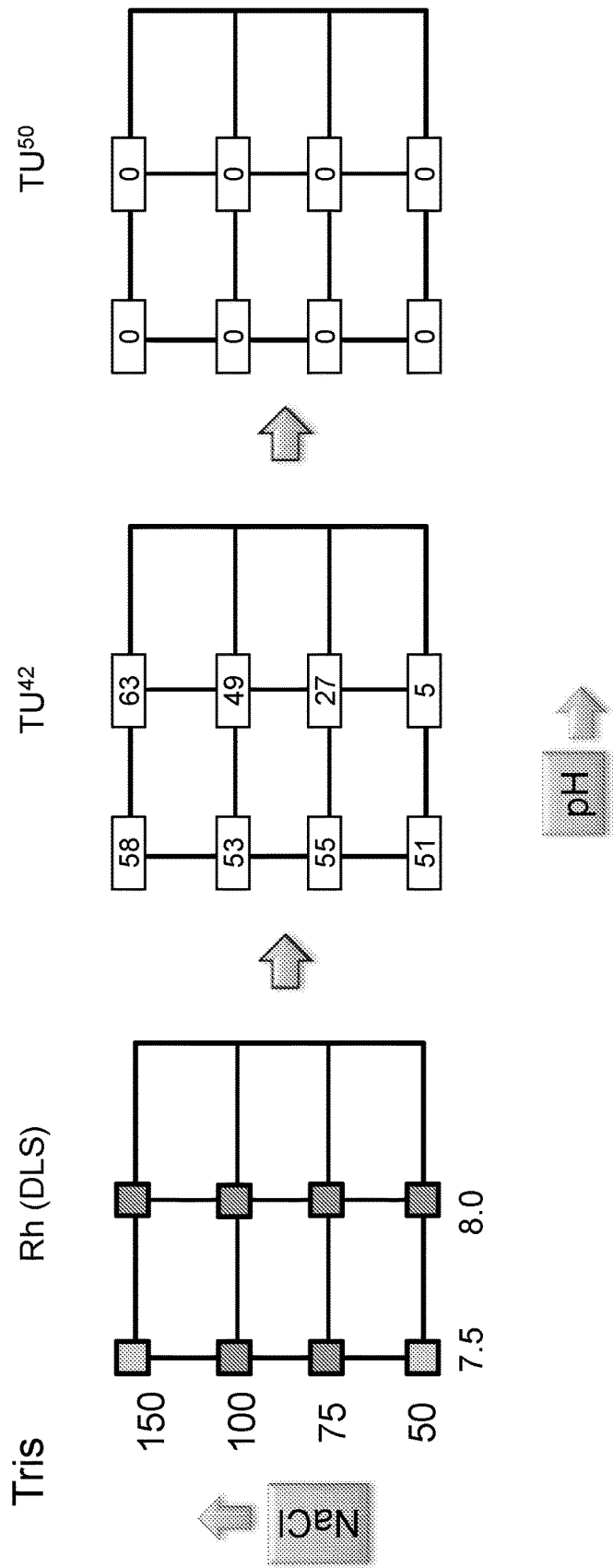
Fig. 19: TU/ml to measure infectivity in term of transgene expression (GFP) and correlation with DLS studies

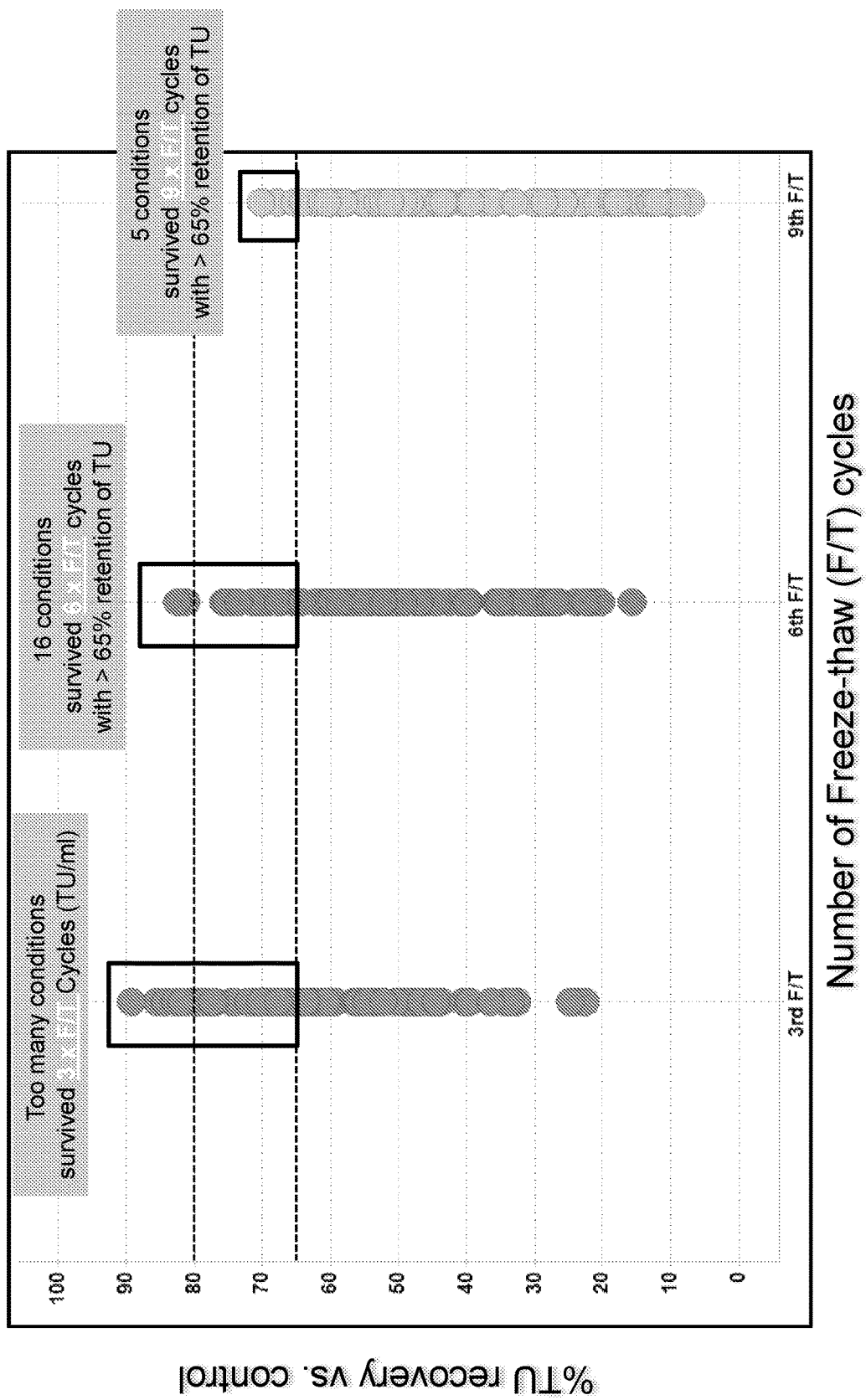
Fig. 20: Freeze-thaw studies of buffer conditions without carbohydrate

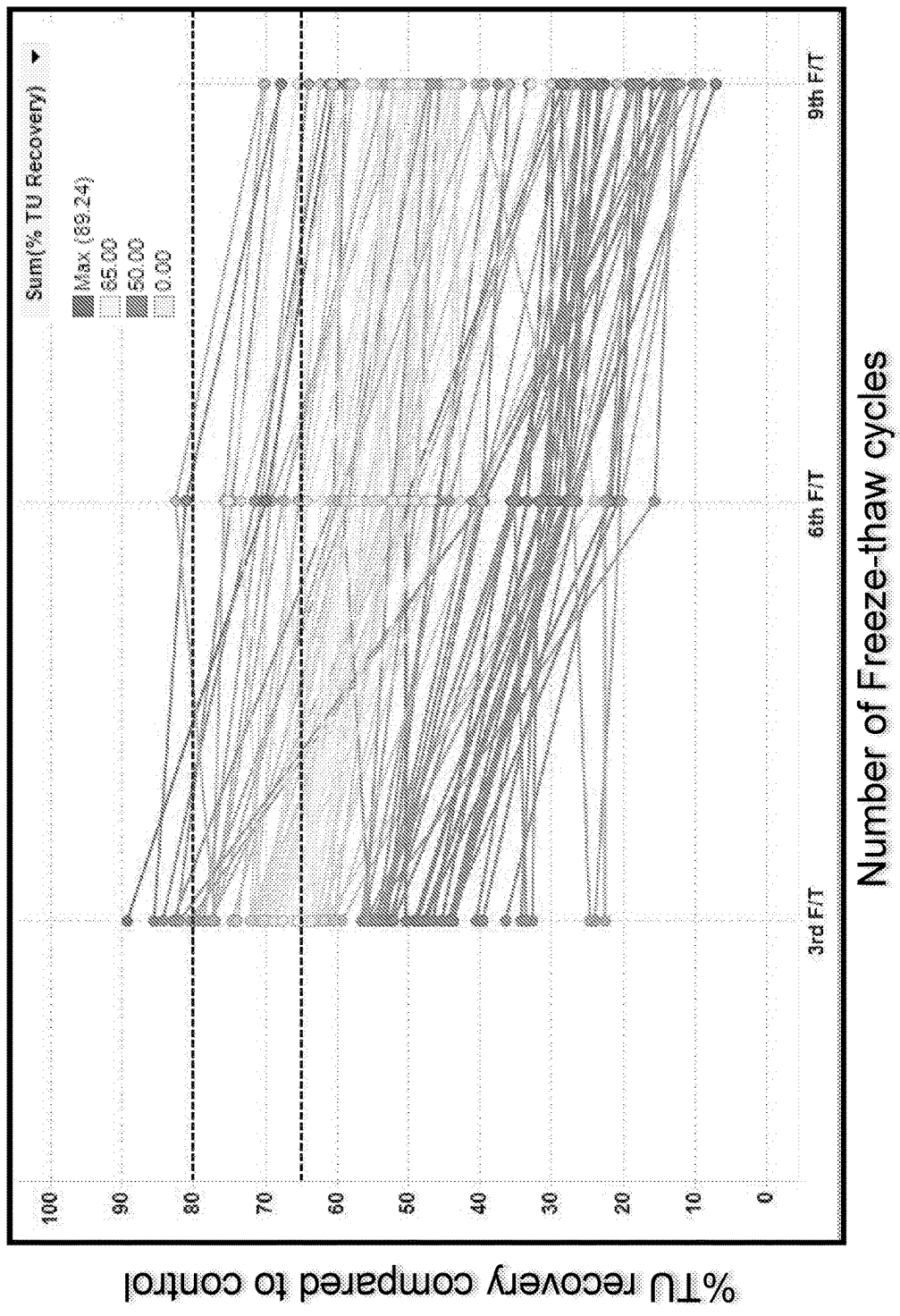
Fig. 21: Inactivation kinetics of lentiviral vectors: buffers without carbohydrate with increase in F/T cycles Fig. 22: Data table of freeze-thaw studies without carbohydrate

| Conditions | TU, Control | FT Cycle | TU @ post sp. F/T Cycle | % TU Recovery vs. Control |
|---|---|---|---|---|
| 20mM MES, 50mM NaCl, pH 6.0 | 2.53E+08 | 3rd F/T | 2.13E+08 | 84.4 |
| 20mM MES, 75mM NaCl, pH 6.0 | 3.20E+08 | 3rd F/T | 2.25E+08 | 70.3 |
| 20mM MES, 100mM NaCl, pH 6.0 | 3.30E+08 | 3rd F/T | 2.34E+08 | 71.1 |
| 20mM MES, 150mM NaCl, pH 6.0 | 3.28E+08 | 3rd F/T | 2.45E+08 | 74.7 |
| 20mM MES, 50 mM NaCl, pH 6.5 | 2.48E+08 | 3rd F/T | 2.21E+08 | 89.2 |
| 20mM MES, 75mM NaCl, pH 6.5 | 2.89E+08 | 3rd F/T | 2.40E+08 | 82.9 |
| 20mM MES, 100mM NaCl, pH 6.5 | 2.86E+08 | 3rd F/T | 2.25E+08 | 78.7 |
| 20mM MES, 150mM NaCl, pH 6.5 | 2.76E+08 | 3rd F/T | 2.04E+08 | 74.0 |
| 20mM MES, 50mM NaCl, pH 6.0 | 2.53E+08 | 6th F/T | 1.81E+08 | 71.6 |
| 20mM MES, 75mM NaCl, pH 6.0 | 3.20E+08 | 6th F/T | 1.68E+08 | 52.6 |
| 20mM MES, 100mM NaCl, pH 6.0 | 3.30E+08 | 6th F/T | 1.90E+08 | 57.8 |
| 20mM MES, 150mM NaCl, pH 6.0 | 3.28E+08 | 6th F/T | 1.89E+08 | 57.7 |
| 20mM MES, 50 mM NaCl, pH 6.5 | 2.48E+08 | 6th F/T | 1.73E+08 | 70.0 |
| 20mM MES, 75mM NaCl, pH 6.5 | 2.89E+08 | 6th F/T | 1.75E+08 | 60.6 |
| 20mM MES, 100mM NaCl, pH 6.5 | 2.86E+08 | 6th F/T | 2.03E+08 | 70.7 |
| 20mM MES, 150mM NaCl, pH 6.5 | 2.76E+08 | 6th F/T | 1.80E+08 | 65.3 |
| 20mM MES, 50mM NaCl, pH 6.0 | 2.53E+08 | 9th F/T | 1.55E+08 | 61.2 |
| 20mM MES, 75mM NaCl, pH 6.0 | 3.20E+08 | 9th F/T | 1.74E+08 | 54.4 |
| 20mM MES, 100mM NaCl, pH 6.0 | 3.30E+08 | 9th F/T | 1.66E+08 | 50.3 |
| 20mM MES, 150mM NaCl, pH 6.0 | 3.28E+08 | 9th F/T | 1.58E+08 | 48.3 |
| 20mM MES, 50 mM NaCl, pH 6.5 | 2.48E+08 | 9th F/T | 1.49E+08 | 60.2 |
| 20mM MES, 75mM NaCl, pH 6.5 | 2.89E+08 | 9th F/T | 1.70E+08 | 58.9 |
| 20mM MES, 100mM NaCl, pH 6.5 | 2.86E+08 | 9th F/T | 1.84E+08 | 64.1 |
| 20mM MES, 150mM NaCl, pH 6.5 | 2.76E+08 | 9th F/T | 1.59E+08 | 57.6 |
| 20mM Histidine, 50mM NaCl, pH 6.0 | 2.70E+08 | 3rd F/T | 1.70E+08 | 63.0 |
| 20mM Histidine, 75mM NaCl, pH 6.0 | 3.07E+08 | 3rd F/T | 2.10E+08 | 68.4 |
| 20mM Histidine, 100mM NaCl, pH 6.0 | 3.50E+08 | 3rd F/T | 2.37E+08 | 67.6 |
| 20mM Histidine, 150mM NaCl, pH 6.0 | 3.66E+08 | 3rd F/T | 2.41E+08 | 65.8 |

Fig. 22 Continued

| Conditions | TU, Control | FT Cycle | TU @ post sp. F/T Cycle | % TU Recovery vs. Control |
|---|---|---|---|---|
| 20mM Histidine, 50mM NaCl, pH 6.5 | 3.09E+08 | 3rd F/T | 2.46E+08 | 79.6 |
| 20mM Histidine, 75mM NaCl, pH 6.5 | 3.41E+08 | 3rd F/T | 2.37E+08 | 69.3 |
| 20mM Histidine, 100mM NaCl, pH 6.5 | 3.45E+08 | 3rd F/T | 2.18E+08 | 63.3 |
| 20mM Histidine, 150mM NaCl, pH 6.5 | 3.19E+08 | 3rd F/T | 2.07E+08 | 65.0 |
| 20mM Histidine, 50mM NaCl, pH 7.0 | 2.83E+08 | 3rd F/T | 1.73E+08 | 61.3 |
| 20mM Histidine, 75mM NaCl, pH 7.0 | 3.38E+08 | 3rd F/T | 1.70E+08 | 50.3 |
| 20mM Histidine, 100mM NaCl, pH 7.0 | 3.62E+08 | 3rd F/T | 1.94E+08 | 53.4 |
| 20mM Histidine, 150mM NaCl, pH 7.0 | 3.68E+08 | 3rd F/T | 1.95E+08 | 53.0 |
| 20mM Histidine, 50mM NaCl, pH 6.0 | 2.70E+08 | 6th F/T | 1.83E+08 | 67.6 |
| 20mM Histidine, 75mM NaCl, pH 6.0 | 3.07E+08 | 6th F/T | 1.67E+08 | 54.6 |
| 20mM Histidine, 100mM NaCl, pH 6.0 | 3.50E+08 | 6th F/T | 2.04E+08 | 58.4 |
| 20mM Histidine, 150mM NaCl, pH 6.0 | 3.66E+08 | 6th F/T | 2.06E+08 | 56.2 |
| 20mM Histidine, 50mM NaCl, pH 6.5 | 3.09E+08 | 6th F/T | 1.80E+08 | 58.3 |
| 20mM Histidine, 75mM NaCl, pH 6.5 | 3.41E+08 | 6th F/T | 1.77E+08 | 51.9 |
| 20mM Histidine, 100mM NaCl, pH 6.5 | 3.45E+08 | 6th F/T | 2.11E+08 | 61.0 |
| 20mM Histidine, 150mM NaCl, pH 6.5 | 3.19E+08 | 6th F/T | 1.90E+08 | 59.4 |
| 20mM Histidine, 50mM NaCl, pH 7.0 | 2.83E+08 | 6th F/T | 1.58E+08 | 56.0 |
| 20mM Histidine, 75mM NaCl, pH 7.0 | 3.38E+08 | 6th F/T | 1.71E+08 | 50.4 |
| 20mM Histidine, 100mM NaCl, pH 7.0 | 3.62E+08 | 6th F/T | 1.44E+08 | 39.9 |
| 20mM Histidine, 150mM NaCl, pH 7.0 | 3.68E+08 | 6th F/T | 1.69E+08 | 46.1 |
| 20mM Histidine, 50mM NaCl, pH 6.0 | 2.70E+08 | 9th F/T | 1.39E+08 | 51.4 |
| 20mM Histidine, 75mM NaCl, pH 6.0 | 3.07E+08 | 9th F/T | 1.64E+08 | 53.6 |
| 20mM Histidine, 100mM NaCl, pH 6.0 | 3.50E+08 | 9th F/T | 1.67E+08 | 47.7 |
| 20mM Histidine, 150mM NaCl, pH 6.0 | 3.66E+08 | 9th F/T | 1.73E+08 | 47.2 |
| 20mM Histidine, 50mM NaCl, pH 6.5 | 3.09E+08 | 9th F/T | 1.61E+08 | 52.2 |
| 20mM Histidine, 75mM NaCl, pH 6.5 | 3.41E+08 | 9th F/T | 1.60E+08 | 47.0 |
| 20mM Histidine, 100mM NaCl, pH 6.5 | 3.45E+08 | 9th F/T | 1.54E+08 | 44.7 |
| 20mM Histidine, 150mM NaCl, pH 6.5 | 3.19E+08 | 9th F/T | 1.77E+08 | 55.4 |

Fig. 22 Continued

| Conditions | TU, Control | FT Cycle | TU @ post sp. F/T Cycle | % TU Recovery vs. Control |
|---|---|---|---|---|
| 20mM Histidine, 50mM NaCl, pH 7.0 | 2.83E+08 | 9th F/T | 1.20E+08 | 42.6 |
| 20mM Histidine, 75mM NaCl, pH 7.0 | 3.38E+08 | 9th F/T | 9.59E+07 | 28.3 |
| 20mM Histidine, 100mM NaCl, pH 7.0 | 3.62E+08 | 9th F/T | 1.30E+08 | 36.0 |
| 20mM Histidine, 150mM NaCl, pH 7.0 | 3.68E+08 | 9th F/T | 1.23E+08 | 33.3 |
| 20mM MOPS 50mM NaCl, pH 6.5 | 3.3E+08 | 3rd F/T | 1.87E+08 | 56.6 |
| 20mM MOPS 75mM NaCl, pH 6.5 | 3.7E+08 | 3rd F/T | 2.08E+08 | 56.3 |
| 20mM MOPS 100mM NaCl, pH 6.5 | 3.21E+08 | 3rd F/T | 2.13E+08 | 66.4 |
| 20mM MOPS 150mM NaCl, pH 6.5 | 3.24E+08 | 3rd F/T | 2.05E+08 | 63.1 |
| 20mM MOPS 50mM NaCl, pH 7.0 | 3.06E+08 | 3rd F/T | 1.91E+08 | 62.4 |
| 20mM MOPS 75mM NaCl, pH 7.0 | 3.3E+08 | 3rd F/T | 2.11E+08 | 63.8 |
| 20mM MOPS 100mM NaCl, pH 7.0 | 3.52E+08 | 3rd F/T | 2.53E+08 | 71.8 |
| 20mM MOPS 150mM NaCl, pH 7.0 | 3.73E+08 | 3rd F/T | 2.03E+08 | 54.3 |
| 20mM MOPS 50mM NaCl, pH 7.5 | 4.05E+08 | 3rd F/T | 1.32E+08 | 32.7 |
| 20mM MOPS 75mM NaCl, pH 7.5 | 4.07E+08 | 3rd F/T | 1.80E+08 | 44.2 |
| 20mM MOPS 100mM NaCl, pH 7.5 | 3.70E+08 | 3rd F/T | 1.50E+08 | 40.5 |
| 20mM MOPS 150mM NaCl, pH 7.5 | 2.21E+08 | 3rd F/T | 1.34E+08 | 60.6 |
| 20mM MOPS 50mM NaCl, pH 6.5 | 3.3E+08 | 6th F/T | 1.62E+08 | 49.0 |
| 20mM MOPS 75mM NaCl, pH 6.5 | 3.7E+08 | 6th F/T | 1.64E+08 | 44.3 |
| 20mM MOPS 100mM NaCl, pH 6.5 | 3.21E+08 | 6th F/T | 2.00E+08 | 62.2 |
| 20mM MOPS 150mM NaCl, pH 6.5 | 3.24E+08 | 6th F/T | 2.10E+08 | 64.7 |
| 20mM MOPS 50mM NaCl, pH 7.0 | 3.06E+08 | 6th F/T | 1.36E+08 | 44.4 |
| 20mM MOPS 75mM NaCl, pH 7.0 | 3.3E+08 | 6th F/T | 1.72E+08 | 52.1 |
| 20mM MOPS 100mM NaCl, pH 7.0 | 3.52E+08 | 6th F/T | 1.74E+08 | 49.3 |
| 20mM MOPS 150mM NaCl, pH 7.0 | 3.73E+08 | 6th F/T | 1.71E+08 | 45.7 |
| 20mM MOPS 50mM NaCl, pH 7.5 | 4.05E+08 | 6th F/T | 1.29E+08 | 31.8 |
| 20mM MOPS 75mM NaCl, pH 7.5 | 4.07E+08 | 6th F/T | 8.47E+07 | 20.8 |
| 20mM MOPS 100mM NaCl, pH 7.5 | 3.70E+08 | 6th F/T | 1.11E+08 | 30.0 |
| 20mM MOPS 150mM NaCl, pH 7.5 | 2.21E+08 | 6th F/T | 1.17E+08 | 52.6 |

Fig. 22 Continued

| Conditions | TU, Control | FT Cycle | TU @ post sp. F/T Cycle | % TU Recovery vs. Control |
|---|---|---|---|---|
| 20mM MOPS 50mM NaCl, pH 6.5 | 3.30E+08 | 9th F/T | 1.51E+08 | 45.7 |
| 20mM MOPS 75mM NaCl, pH 6.5 | 3.70E+08 | 9th F/T | 1.11E+08 | 30.0 |
| 20mM MOPS 100mM NaCl, pH 6.5 | 3.21E+08 | 9th F/T | 1.60E+08 | 49.9 |
| 20mM MOPS 150mM NaCl, pH 6.5 | 3.24E+08 | 9th F/T | 1.78E+08 | 55.0 |
| 20mM MOPS 50mM NaCl, pH 7.0 | 3.06E+08 | 9th F/T | 1.32E+08 | 43.0 |
| 20mM MOPS 75mM NaCl, pH 7.0 | 3.30E+08 | 9th F/T | 1.45E+08 | 44.0 |
| 20mM MOPS 100mM NaCl, pH 7.0 | 3.52E+08 | 9th F/T | 1.62E+08 | 45.9 |
| 20mM MOPS 150mM NaCl, pH 7.0 | 3.73E+08 | 9th F/T | 1.40E+08 | 37.6 |
| 20mM MOPS 50mM NaCl, pH 7.5 | 4.05E+08 | 9th F/T | 5.50E+07 | 13.6 |
| 20mM MOPS 75mM NaCl, pH 7.5 | 4.07E+08 | 9th F/T | 7.10E+07 | 17.4 |
| 20mM MOPS 100mM NaCl, pH 7.5 | 3.70E+08 | 9th F/T | 9.07E+07 | 24.5 |
| 20mM MOPS 150mM NaCl, pH 7.5 | 2.21E+08 | 9th F/T | 8.00E+07 | 36.1 |
| 20mM Phosphate 50mM NaCl, pH 6.5 | 2.66E+08 | 3rd F/T | 1.88E+08 | 70.7 |
| 20mM Phosphate 75mM NaCl, pH 6.5 | 3.27E+08 | 3rd F/T | 2.15E+08 | 65.6 |
| 20mM Phosphate 100mM NaCl, pH 6.5 | 3.37E+08 | 3rd F/T | 2.61E+08 | 77.4 |
| 20mM Phosphate 150mM NaCl, pH 6.5 | 3.61E+08 | 3rd F/T | 2.00E+08 | 55.3 |
| 20mM Phosphate 50mM NaCl, pH 7.0 | 3.48E+08 | 3rd F/T | 2.25E+08 | 64.8 |
| 20mM Phosphate 75mM NaCl, pH 7.0 | 3.76E+08 | 3rd F/T | 2.58E+08 | 68.6 |
| 20mM Phosphate 100mM NaCl, pH 7.0 | 3.58E+08 | 3rd F/T | 2.24E+08 | 62.7 |
| 20mM Phosphate 150mM NaCl, pH 7.0 | 2.95E+08 | 3rd F/T | 2.07E+08 | 70.1 |
| 20mM Phosphate 50mM NaCl, pH 7.5 | 2.26E+08 | 3rd F/T | 1.63E+08 | 72.0 |
| 20mM Phosphate 75mM NaCl, pH 7.5 | 3.46E+08 | 3rd F/T | 2.14E+08 | 61.9 |
| 20mM Phosphate 100mM NaCl, pH 7.5 | 3.81E+08 | 3rd F/T | 1.78E+08 | 46.7 |
| 20mM Phosphate 150mM NaCl, pH 7.5 | 3.50E+08 | 3rd F/T | 1.56E+08 | 44.5 |
| 20mM Phosphate 50mM NaCl, pH 8.0 | 3.62E+08 | 3rd F/T | 1.96E+08 | 54.0 |
| 20mM Phosphate 75mM NaCl, pH 8.0 | 3.56E+08 | 3rd F/T | 2.92E+08 | 82.0 |
| 20mM Phosphate 100mM NaCl, pH 8.0 | 4.13E+08 | 3rd F/T | 1.81E+08 | 43.9 |
| 20mM Phosphate 150mM NaCl, pH 8.0 | 2.16E+08 | 3rd F/T | 1.13E+08 | 52.3 |

Fig. 22 Continued

| Conditions | TU, Control | FT Cycle | TU @ post sp. F/T Cycle | % TU Recovery vs. Control |
|---|---|---|---|---|
| 20mM Phosphate 50mM NaCl pH 6.5 | 2.66E+08 | 6th F/T | 1.95E+08 | 73.5 |
| 20mM Phosphate 75mM NaCl pH 6.5 | 3.27E+08 | 6th F/T | 1.90E+08 | 58.2 |
| 20mM Phosphate 100mM NaCl pH 6.5 | 3.37E+08 | 6th F/T | 2.28E+08 | 67.7 |
| 20mM Phosphate 150mM NaCl pH 6.5 | 3.61E+08 | 6th F/T | 2.14E+08 | 59.2 |
| 20mM Phosphate 50mM NaCl pH 7.0 | 3.48E+08 | 6th F/T | 1.99E+08 | 57.1 |
| 20mM Phosphate 75mM NaCl pH 7.0 | 3.76E+08 | 6th F/T | 2.05E+08 | 54.4 |
| 20mM Phosphate 100mM NaCl pH 7.0 | 3.58E+08 | 6th F/T | 1.81E+08 | 50.7 |
| 20mM Phosphate 150mM NaCl pH 7.0 | 2.95E+08 | 6th F/T | 1.79E+08 | 60.6 |
| 20mM Phosphate 50mM NaCl pH 7.5 | 2.26E+08 | 6th F/T | 1.19E+08 | 52.8 |
| 20mM Phosphate 75mM NaCl pH 7.5 | 3.46E+08 | 6th F/T | 1.65E+08 | 47.6 |
| 20mM Phosphate 100mM NaCl pH 7.5 | 3.81E+08 | 6th F/T | 1.37E+08 | 35.9 |
| 20mM Phosphate 150mM NaCl pH 7.5 | 3.50E+08 | 6th F/T | 9.76E+07 | 27.9 |
| 20mM Phosphate 50mM NaCl pH 8.0 | 3.62E+08 | 6th F/T | 1.29E+08 | 35.5 |
| 20mM Phosphate 75mM NaCl pH 8.0 | 3.56E+08 | 6th F/T | 1.41E+08 | 39.8 |
| 20mM Phosphate 100mM NaCl pH 8.0 | 4.13E+08 | 6th F/T | 1.14E+08 | 27.5 |
| 20mM Phosphate 150mM NaCl pH 8.0 | 2.16E+08 | 6th F/T | 8.56E+07 | 39.6 |
| 20mM Phosphate 50mM NaCl pH 6.5 | 2.66E+08 | 9th F/T | 1.54E+08 | 58.1 |
| 20mM Phosphate 75mM NaCl pH 6.5 | 3.27E+08 | 9th F/T | 1.45E+08 | 44.4 |
| 20mM Phosphate 100mM NaCl pH 6.5 | 3.37E+08 | 9th F/T | 1.79E+08 | 53.1 |
| 20mM Phosphate 150mM NaCl pH 6.5 | 3.61E+08 | 9th F/T | 1.70E+08 | 47.2 |
| 20mM Phosphate 50mM NaCl pH 7.0 | 3.48E+08 | 9th F/T | 1.78E+08 | 51.1 |
| 20mM Phosphate 75mM NaCl pH 7.0 | 3.76E+08 | 9th F/T | 1.97E+08 | 52.2 |
| 20mM Phosphate 100mM NaCl pH 7.0 | 3.58E+08 | 9th F/T | 1.71E+08 | 47.8 |
| 20mM Phosphate 150mM NaCl pH 7.0 | 2.95E+08 | 9th F/T | 1.46E+08 | 49.4 |
| 20mM Phosphate 50mM NaCl pH 7.5 | 2.26E+08 | 9th F/T | 8.94E+07 | 39.6 |
| 20mM Phosphate 75mM NaCl pH 7.5 | 3.46E+08 | 9th F/T | 1.05E+08 | 30.3 |
| 20mM Phosphate 100mM NaCl pH 7.5 | 3.81E+08 | 9th F/T | 8.00E+07 | 21.0 |
| 20mM Phosphate 150mM NaCl pH 7.5 | 3.50E+08 | 9th F/T | 8.21E+07 | 23.4 |

Fig. 22 Continued

| Conditions | TU, Control | FT Cycle | TU @ post sp. F/T Cycle | % TU Recovery vs. Control |
|---|---|---|---|---|
| 20mM Phosphate 50mM NaCl, pH 8.0 | 3.62E+08 | 9th F/T | 4.77E+07 | 13.2 |
| 20mM Phosphate 75mM NaCl, pH 8.0 | 3.56E+08 | 9th F/T | 3.66E+07 | 10.3 |
| 20mM Phosphate 100mM NaCl, pH 8.0 | 4.13E+08 | 9th F/T | 2.92E+07 | 7.1 |
| 20mM Phosphate 150mM NaCl, pH 8.0 | 2.16E+08 | 9th F/T | 3.10E+07 | 14.3 |
| 20mM PIPES 50mM NaCl, pH 6.5 | 2.58E+08 | 3rd F/T | 1.99E+08 | 77.0 |
| 20mM PIPES 75mM NaCl, pH 6.5 | 3.51E+08 | 3rd F/T | 2.46E+08 | 70.2 |
| 20mM PIPES 100mM NaCl, pH 6.5 | 3.86E+08 | 3rd F/T | 2.16E+08 | 56.1 |
| 20mM PIPES 150mM NaCl, pH 6.5 | 3.64E+08 | 3rd F/T | 2.35E+08 | 64.6 |
| 20mM PIPES 50mM NaCl, pH 7.0 | 3.31E+08 | 3rd F/T | 2.17E+08 | 65.5 |
| 20mM PIPES 75mM NaCl, pH 7.0 | 3.67E+08 | 3rd F/T | 2.49E+08 | 67.7 |
| 20mM PIPES 100mM NaCl, pH 7.0 | 3.57E+08 | 3rd F/T | 2.26E+08 | 63.4 |
| 20mM PIPES 150mM NaCl, pH 7.0 | 2.80E+08 | 3rd F/T | 1.93E+08 | 68.8 |
| 20mM PIPES 50mM NaCl, pH 7.5 | 2.15E+08 | 3rd F/T | 1.66E+08 | 77.4 |
| 20mM PIPES 75mM NaCl, pH 7.5 | 2.96E+08 | 3rd F/T | 1.89E+08 | 63.7 |
| 20mM PIPES 100mM NaCl, pH 7.5 | 3.15E+08 | 3rd F/T | 1.90E+08 | 60.5 |
| 20mM PIPES 150mM NaCl, pH 7.5 | 2.90E+08 | 3rd F/T | 1.59E+08 | 54.7 |
| 20mM PIPES 50mM NaCl, pH 6.5 | 2.58E+08 | 6th F/T | 2.13E+08 | 82.5 |
| 20mM PIPES 75mM NaCl, pH 6.5 | 3.51E+08 | 6th F/T | 2.06E+08 | 58.8 |
| 20mM PIPES 100mM NaCl, pH 6.5 | 3.86E+08 | 6th F/T | 2.02E+08 | 52.3 |
| 20mM PIPES 150mM NaCl, pH 6.5 | 3.64E+08 | 6th F/T | 2.16E+08 | 59.3 |
| 20mM PIPES 50mM NaCl, pH 7.0 | 3.31E+08 | 6th F/T | 1.55E+08 | 46.8 |
| 20mM PIPES 75mM NaCl, pH 7.0 | 3.67E+08 | 6th F/T | 1.81E+08 | 49.2 |
| 20mM PIPES 100mM NaCl, pH 7.0 | 3.57E+08 | 6th F/T | 1.96E+08 | 54.9 |
| 20mM PIPES 150mM NaCl, pH 7.0 | 2.80E+08 | 6th F/T | 1.80E+08 | 64.2 |
| 20mM PIPES 50mM NaCl, pH 7.5 | 2.15E+08 | 6th F/T | 1.29E+08 | 59.9 |
| 20mM PIPES 75mM NaCl, pH 7.5 | 2.96E+08 | 6th F/T | 1.55E+08 | 52.2 |
| 20mM PIPES 100mM NaCl, pH 7.5 | 3.15E+08 | 6th F/T | 1.26E+08 | 39.9 |
| 20mM PIPES 150mM NaCl, pH 7.5 | 2.90E+08 | 6th F/T | 1.02E+08 | 35.1 |

Fig. 22 Continued

| Conditions | TU, Control | FT Cycle | TU @ post sp. F/T Cycle | % TU Recovery vs. Control |
|---|---|---|---|---|
| 20mM PIPES 50mM NaCl, pH 6.5 | 2.58E+08 | 9th F/T | 1.81E+08 | 70.3 |
| 20mM PIPES 75mM NaCl, pH 6.5 | 3.51E+08 | 9th F/T | 2.13E+08 | 60.7 |
| 20mM PIPES 100mM NaCl, pH 6.5 | 3.86E+08 | 9th F/T | 1.80E+08 | 46.7 |
| 20mM PIPES 150mM NaCl, pH 6.5 | 3.64E+08 | 9th F/T | 1.76E+08 | 48.4 |
| 20mM PIPES 50mM NaCl, pH 7.0 | 3.31E+08 | 9th F/T | 1.70E+08 | 51.4 |
| 20mM PIPES 75mM NaCl, pH 7.0 | 3.67E+08 | 9th F/T | 1.60E+08 | 43.4 |
| 20mM PIPES 100mM NaCl, pH 7.0 | 3.57E+08 | 9th F/T | 1.57E+08 | 44.1 |
| 20mM PIPES 150mM NaCl, pH 7.0 | 2.80E+08 | 9th F/T | 1.38E+08 | 49.3 |
| 20mM PIPES 50mM NaCl, pH 7.5 | 2.15E+08 | 9th F/T | 8.47E+07 | 39.5 |
| 20mM PIPES 75mM NaCl, pH 7.5 | 2.96E+08 | 9th F/T | 9.76E+07 | 32.9 |
| 20mM PIPES 100mM NaCl, pH 7.5 | 3.15E+08 | 9th F/T | 6.58E+07 | 20.9 |
| 20mM PIPES 150mM NaCl, pH 7.5 | 2.90E+08 | 9th F/T | 5.46E+07 | 18.8 |
| 20mM HEPES 50mM NaCl, pH 7.0 | 3.16E+08 | 3rd F/T | 2.21E+08 | 69.9 |
| 20mM HEPES 75mM NaCl, pH 7.0 | 3.78E+08 | 3rd F/T | 2.61E+08 | 69.1 |
| 20mM HEPES 100mM NaCl, pH 7.0 | 3.26E+08 | 3rd F/T | 2.14E+08 | 65.6 |
| 20mM HEPES 150mM NaCl, pH 7.0 | 2.94E+08 | 3rd F/T | 1.85E+08 | 63.0 |
| 20mM HEPES 50mM NaCl, pH 7.5 | 1.51E+08 | 3rd F/T | 1.22E+08 | 80.7 |
| 20mM HEPES 75mM NaCl, pH 7.5 | 3.12E+08 | 3rd F/T | 1.74E+08 | 55.8 |
| 20mM HEPES 100mM NaCl, pH 7.5 | 2.85E+08 | 3rd F/T | 1.35E+08 | 47.5 |
| 20mM HEPES 150mM NaCl, pH 7.5 | 3.02E+08 | 3rd F/T | 1.44E+08 | 47.8 |
| 20mM HEPES 50mM NaCl, pH 8.0 | 2.09E+08 | 3rd F/T | 1.16E+08 | 55.4 |
| 20mM HEPES 75mM NaCl, pH 8.0 | 2.42E+08 | 3rd F/T | 1.16E+08 | 47.8 |
| 20mM HEPES 100mM NaCl, pH 8.0 | 2.72E+08 | 3rd F/T | 1.20E+08 | 44.1 |
| 20mM HEPES 150mM NaCl, pH 8.0 | 1.75E+08 | 3rd F/T | 9.25E+07 | 52.7 |
| 20mM HEPES 50mM NaCl, pH 7.0 | 3.16E+08 | 6th F/T | 1.58E+08 | 50.0 |
| 20mM HEPES 75mM NaCl, pH 7.0 | 3.78E+08 | 6th F/T | 1.62E+08 | 42.7 |
| 20mM HEPES 100mM NaCl, pH 7.0 | 3.26E+08 | 6th F/T | 1.76E+08 | 54.0 |
| 20mM HEPES 150mM NaCl, pH 7.0 | 2.94E+08 | 6th F/T | 1.51E+08 | 51.2 |

Fig. 22 Continued

| Conditions | TU, Control | FT Cycle | TU @ post sp. F/T Cycle | % TU Recovery vs. Control |
|---|---|---|---|---|
| 20mM HEPES 50mM NaCl, pH 7.5 | 1.51E+08 | 6th F/T | 6.02E+07 | 39.8 |
| 20mM HEPES 75mM NaCl, pH 7.5 | 3.12E+08 | 6th F/T | 8.73E+07 | 28.0 |
| 20mM HEPES 100mM NaCl, pH 7.5 | 2.85E+08 | 6th F/T | 8.34E+07 | 29.3 |
| 20mM HEPES 150mM NaCl, pH 7.5 | 3.02E+08 | 6th F/T | 8.39E+07 | 27.7 |
| 20mM HEPES 50mM NaCl, pH 8.0 | 2.09E+08 | 6th F/T | 3.27E+07 | 15.6 |
| 20mM HEPES 75mM NaCl, pH 8.0 | 2.42E+08 | 6th F/T | 5.29E+07 | 21.8 |
| 20mM HEPES 100mM NaCl, pH 8.0 | 2.72E+08 | 6th F/T | 7.61E+07 | 28.0 |
| 20mM HEPES 150mM NaCl, pH 8.0 | 1.75E+08 | 6th F/T | 6.11E+07 | 34.8 |
| 20mM HEPES 50mM NaCl, pH 7.0 | 3.16E+08 | 9th F/T | 1.52E+08 | 48.1 |
| 20mM HEPES 75mM NaCl, pH 7.0 | 3.78E+08 | 9th F/T | 1.65E+08 | 43.6 |
| 20mM HEPES 100mM NaCl, pH 7.0 | 3.26E+08 | 9th F/T | 1.55E+08 | 47.4 |
| 20mM HEPES 150mM NaCl, pH 7.0 | 2.94E+08 | 9th F/T | 1.44E+08 | 48.8 |
| 20mM HEPES 50mM NaCl, pH 7.5 | 1.51E+08 | 9th F/T | 4.09E+07 | 27.0 |
| 20mM HEPES 75mM NaCl, pH 7.5 | 3.12E+08 | 9th F/T | 4.09E+07 | 13.1 |
| 20mM HEPES 100mM NaCl, pH 7.5 | 2.85E+08 | 9th F/T | 6.54E+07 | 22.9 |
| 20mM HEPES 150mM NaCl, pH 7.5 | 3.02E+08 | 9th F/T | 7.53E+07 | 24.9 |
| 20mM HEPES 50mM NaCl, pH 8.0 | 2.09E+08 | 9th F/T | 2.62E+07 | 12.5 |
| 20mM HEPES 75mM NaCl, pH 8.0 | 2.42E+08 | 9th F/T | 3.83E+07 | 15.8 |
| 20mM HEPES 100mM NaCl, pH 8.0 | 2.72E+08 | 9th F/T | 5.25E+07 | 19.3 |
| 20mM HEPES 150mM NaCl, pH 8.0 | 1.75E+08 | 9th F/T | 4.47E+07 | 25.5 |
| 20mM HEPPS 50mM NaCl, pH 7.5 | 2.12E+08 | 3rd F/T | 1.65E+08 | 77.7 |
| 20mM HEPPS 75mM NaCl, pH 7.5 | 2.46E+08 | 3rd F/T | 1.46E+08 | 59.4 |
| 20mM HEPPS 100mM NaCl, pH 7.5 | 2.95E+08 | 3rd F/T | 1.82E+08 | 61.7 |
| 20mM HEPPS 150mM NaCl, pH 7.5 | 2.98E+08 | 3rd F/T | 1.32E+08 | 44.2 |
| 20mM HEPPS 50mM NaCl, pH 8.0 | 2.07E+08 | 3rd F/T | 1.11E+08 | 53.7 |
| 20mM HEPPS 75mM NaCl, pH 8.0 | 1.97E+08 | 3rd F/T | 9.63E+07 | 48.8 |
| 20mM HEPPS 100mM NaCl, pH 8.0 | 2.46E+08 | 3rd F/T | 1.21E+08 | 49.0 |
| 20mM HEPPS 150mM NaCl, pH 8.0 | 2.25E+08 | 3rd F/T | 1.02E+08 | 45.4 |

Fig. 22 Continued

| Conditions | TU, Control | FT Cycle | TU @ post sp. F/T Cycle | % TU Recovery vs. Control |
|---|---|---|---|---|
| 20mM HEPPS 50mM NaCl, pH 7.5 | 2.12E+08 | 6th F/T | 1.05E+08 | 49.5 |
| 20mM HEPPS 75mM NaCl, pH 7.5 | 2.46E+08 | 6th F/T | 6.72E+07 | 27.3 |
| 20mM HEPPS 100mM NaCl, pH 7.5 | 2.95E+08 | 6th F/T | 7.14E+07 | 24.2 |
| 20mM HEPPS 150mM NaCl, pH 7.5 | 2.98E+08 | 6th F/T | 8.99E+07 | 30.2 |
| 20mM HEPPS 50mM NaCl, pH 8.0 | 2.07E+08 | 6th F/T | 8.51E+07 | 41.1 |
| 20mM HEPPS 75mM NaCl, pH 8.0 | 1.97E+08 | 6th F/T | 6.19E+07 | 31.4 |
| 20mM HEPPS 100mM NaCl, pH 8.0 | 2.46E+08 | 6th F/T | 7.61E+07 | 30.9 |
| 20mM HEPPS 150mM NaCl, pH 8.0 | 2.25E+08 | 6th F/T | 7.53E+07 | 33.4 |
| 20mM HEPPS 50mM NaCl, pH 7.5 | 2.12E+08 | 9th F/T | 5.81E+07 | 27.4 |
| 20mM HEPPS 75mM NaCl, pH 7.5 | 2.46E+08 | 9th F/T | 9.98E+07 | 40.6 |
| 20mM HEPPS 100mM NaCl, pH 7.5 | 2.95E+08 | 9th F/T | 8.39E+07 | 28.4 |
| 20mM HEPPS 150mM NaCl, pH 7.5 | 2.98E+08 | 9th F/T | 8.90E+07 | 29.9 |
| 20mM HEPPS 50mM NaCl, pH 8.0 | 2.07E+08 | 9th F/T | 2.58E+07 | 12.4 |
| 20mM HEPPS 75mM NaCl, pH 8.0 | 1.97E+08 | 9th F/T | 5.03E+07 | 25.5 |
| 20mM HEPPS 100mM NaCl, pH 8.0 | 2.46E+08 | 9th F/T | 5.59E+07 | 22.7 |
| 20mM HEPPS 150mM NaCl, pH 8.0 | 2.25E+08 | 9th F/T | 6.71E+07 | 29.8 |
| 20mM Tris 50mM NaCl, pH 7.5 | 2.37E+08 | 3rd F/T | 8.64E+07 | 36.4 |
| 20mM Tris 75mM NaCl, pH 7.5 | 2.61E+08 | 3rd F/T | 1.36E+08 | 52.2 |
| 20mM Tris 100mM NaCl, pH 7.5 | 2.97E+08 | 3rd F/T | 1.18E+08 | 39.7 |
| 20mM Tris 150mM NaCl, pH 7.5 | 2.61E+08 | 3rd F/T | 8.94E+07 | 34.3 |
| 20mM Tris 50mM NaCl, pH 8.0 | 1.92E+08 | 3rd F/T | 4.34E+07 | 22.6 |
| 20mM Tris 75mM NaCl, pH 8.0 | 1.74E+08 | 3rd F/T | 4.30E+07 | 24.8 |
| 20mM Tris 100mM NaCl, pH 8.0 | 1.95E+08 | 3rd F/T | 4.69E+07 | 24.1 |
| 20mM Tris 150mM NaCl, pH 8.0 | 1.57E+08 | 3rd F/T | 5.29E+07 | 33.6 |
| 20mM Tris 50mM NaCl, pH 7.5 | 2.37E+08 | 6th F/T | 5.25E+07 | 22.1 |
| 20mM Tris 75mM NaCl, pH 7.5 | 2.61E+08 | 6th F/T | 7.22E+07 | 27.7 |
| 20mM Tris 100mM NaCl, pH 7.5 | 2.97E+08 | 6th F/T | 7.87E+07 | 26.5 |
| 20mM Tris 150mM NaCl, pH 7.5 | 2.61E+08 | 6th F/T | 8.21E+07 | 31.5 |

Fig. 22 Continued

| Conditions | TU, Control | FT Cycle | TU @ post sp. F/T Cycle | % TU Recovery vs. Control |
|---|---|---|---|---|
| 20mM Tris 50mM NaCl, pH 8.0 | 1.92E+08 | 6th F/T | 4.34E+07 | 22.6 |
| 20mM Tris 75mM NaCl, pH 8.0 | 1.74E+08 | 6th F/T | 4.69E+07 | 27.0 |
| 20mM Tris 100mM NaCl, pH 8.0 | 1.95E+08 | 6th F/T | 3.96E+07 | 20.3 |
| 20mM Tris 150mM NaCl, pH 8.0 | 1.57E+08 | 6th F/T | 5.55E+07 | 35.2 |
| 20mM Tris 50mM NaCl, pH 7.5 | 2.37E+08 | 9th F/T | 4.26E+07 | 17.9 |
| 20mM Tris 75mM NaCl, pH 7.5 | 2.61E+08 | 9th F/T | 7.48E+07 | 28.7 |
| 20mM Tris 100mM NaCl, pH 7.5 | 2.97E+08 | 9th F/T | 3.78E+07 | 12.7 |
| 20mM Tris 150mM NaCl, pH 7.5 | 2.61E+08 | 9th F/T | 6.71E+07 | 25.7 |
| 20mM Tris 50mM NaCl, pH 8.0 | 1.92E+08 | 9th F/T | 1.76E+07 | 9.2 |
| 20mM Tris 75mM NaCl, pH 8.0 | 1.74E+08 | 9th F/T | 2.11E+07 | 12.1 |
| 20mM Tris 100mM NaCl, pH 8.0 | 1.95E+08 | 9th F/T | 1.85E+07 | 9.5 |
| 20mM Tris 150mM NaCl, pH 8.0 | 1.57E+08 | 9th F/T | 2.88E+07 | 18.3 |
| 20mM Citrate 50mM NaCl, pH 6.0 | 2.91E+08 | 3rd F/T | 2.25E+08 | 77.4 |
| 20mM Citrate 75mM NaCl, pH 6.0 | 3.18E+08 | 3rd F/T | 2.10E+08 | 65.9 |
| 20mM Citrate 100mM NaCl, pH 6.0 | 3.12E+08 | 3rd F/T | 2.57E+08 | 82.4 |
| 20mM Citrate 150mM NaCl, pH 6.0 | 3.35E+08 | 3rd F/T | 2.40E+08 | 71.9 |
| 20mM Citrate 50mM NaCl, pH 6.5 | 2.63E+08 | 3rd F/T | 2.25E+08 | 85.6 |
| 20mM Citrate 75mM NaCl, pH 6.5 | 3.10E+08 | 3rd F/T | 1.98E+08 | 64.0 |
| 20mM Citrate 100mM NaCl, pH 6.5 | 3.32E+08 | 3rd F/T | 2.39E+08 | 72.1 |
| 20mM Citrate 150mM NaCl, pH 6.5 | 3.17E+08 | 3rd F/T | 2.46E+08 | 77.4 |
| 20mM Citrate 50mM NaCl, pH 6.0 | 2.91E+08 | 6th F/T | 2.01E+08 | 69.1 |
| 20mM Citrate 75mM NaCl, pH 6.0 | 3.18E+08 | 6th F/T | 2.14E+08 | 67.3 |
| 20mM Citrate 100mM NaCl, pH 6.0 | 3.12E+08 | 6th F/T | 2.33E+08 | 74.7 |
| 20mM Citrate 150mM NaCl, pH 6.0 | 3.35E+08 | 6th F/T | 2.19E+08 | 65.4 |
| 20mM Citrate 50mM NaCl, pH 6.5 | 2.63E+08 | 6th F/T | 2.14E+08 | 81.2 |
| 20mM Citrate 75mM NaCl, pH 6.5 | 3.10E+08 | 6th F/T | 2.33E+08 | 75.3 |
| 20mM Citrate 100mM NaCl, pH 6.5 | 3.32E+08 | 6th F/T | 2.30E+08 | 69.4 |
| 20mM Citrate 150mM NaCl, pH 6.5 | 3.17E+08 | 6th F/T | 2.40E+08 | 75.7 |
| 20mM Citrate 50mM NaCl, pH 6.0 | 2.91E+08 | 9th F/T | 1.45E+08 | 49.8 |
| 20mM Citrate 75mM NaCl, pH 6.0 | 3.18E+08 | 9th F/T | 1.87E+08 | 58.6 |
| 20mM Citrate 100mM NaCl, pH 6.0 | 3.12E+08 | 9th F/T | 2.12E+08 | 67.9 |
| 20mM Citrate 150mM NaCl, pH 6.0 | 3.35E+08 | 9th F/T | 2.04E+08 | 60.9 |
| 20mM Citrate 50mM NaCl, pH 6.5 | 2.63E+08 | 9th F/T | 1.78E+08 | 67.8 |
| 20mM Citrate 75mM NaCl, pH 6.5 | 3.10E+08 | 9th F/T | 2.03E+08 | 65.4 |
| 20mM Citrate 100mM NaCl, pH 6.5 | 3.32E+08 | 9th F/T | 2.07E+08 | 62.4 |
| 20mM Citrate 150mM NaCl, pH 6.5 | 3.17E+08 | 9th F/T | 2.22E+08 | 70.1 |

Fig. 23: Examples of selected stabilizing buffer conditions, post 9th freeze-thaw cycle, without carbohydrate

| Conditions | % TU retained (9th F/T) | % TU retained (6th F/T) | % TU retained (3rd F/T) |
|---|---|---|---|
| 20 mM PIPES 50 mM NaCl, pH 6.5 | 70.3 | 82.5 | 77.0 |
| 20 mM Citrate 100 mM NaCl, pH 6.0 | 67.9 | 74.7 | 82.4 |
| 20 mM Citrate 50 mM NaCl, pH 6.5 | 67.8 | 81.2 | 85.6 |
| 20 mM Citrate 75 mM NaCl, pH 6.5 | 65.4 | 75.3 | 64.0 |
| 20 mM Citrate 150 mM NaCl, pH 6.5 | 70.1 | 75.7 | 77.4 |

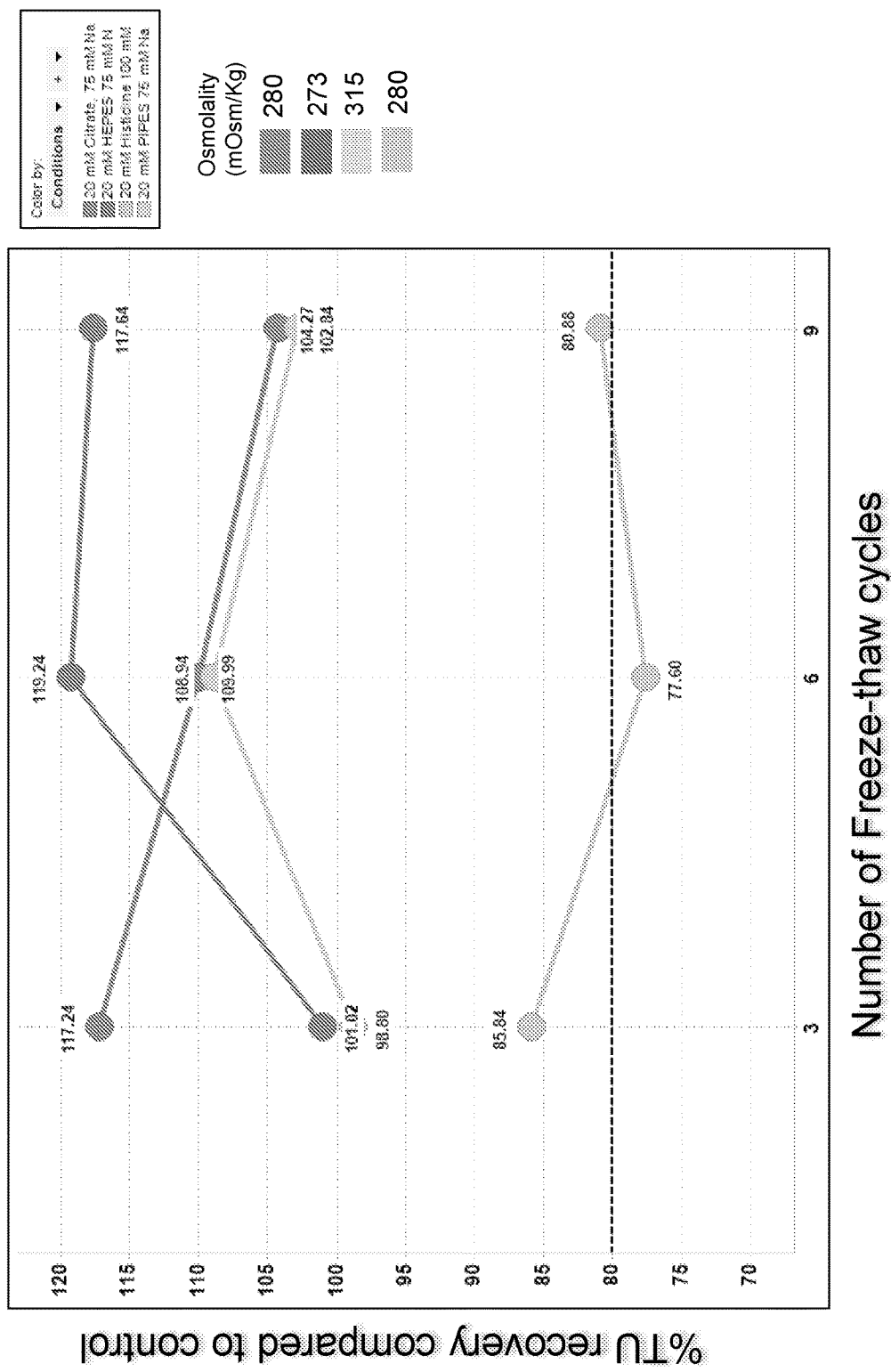
Fig. 24: Freeze-thaw studies of selected buffer conditions with carbohydrate Fig. 25: Data table, freeze-thaw studies of selected buffer conditions with carbohydrate

| Conditions | TU, Control | FT Cycle | TU | %TU recovery | Average %TU recovery |
|---|---|---|---|---|---|
| 20 mM Histidine 100 mM NaCl, 2.5% Sucrose, pH 6.5 | 7.78E+07 | 3 | 6.67E+07 | 85.6 | 85.8 |
|  | 7.40E+07 | 3 | 6.36E+07 | 86.0 |  |
| 20 mM HEPES 75 mM NaCl, 2.5% Sucrose, pH 7.0 | 7.44E+07 | 3 | 6.72E+07 | 90.2 | 101.0 |
|  | 5.07E+07 | 3 | 5.68E+07 | 111.9 |  |
| 20 mM Citrate 75 mM NaCl, 2.5% Sucrose, pH 6.5 | 1.06E+08 | 3 | 1.28E+08 | 120.2 | 117.2 |
|  | 1.12E+08 | 3 | 1.28E+08 | 114.2 |  |
| 20 mM PIPES 75 mM NaCl, 2.5% Sucrose, pH 6.5 | 8.47E+07 | 3 | 9.33E+07 | 110.2 | 98.8 |
|  | 9.93E+07 | 3 | 8.69E+07 | 87.4 |  |
| 20 mM Histidine 100 mM NaCl, 2.5% Sucrose, pH 6.5 | 7.78E+07 | 6 | 6.11E+07 | 78.5 | 77.6 |
|  | 7.40E+07 | 6 | 5.68E+07 | 76.7 |  |
| 20 mM HEPES 75 mM NaCl, 2.5% Sucrose, pH 7.0 | 7.44E+07 | 6 | 6.71E+07 | 90.2 | 119.2 |
|  | 5.07E+07 | 6 | 7.53E+07 | 148.3 |  |
| 20 mM Citrate 75 mM NaCl, 2.5% Sucrose, pH 6.5 | 1.06E+08 | 6 | 1.14E+08 | 107.3 | 110.0 |
|  | 1.12E+08 | 6 | 1.26E+08 | 112.7 |  |
| 20 mM PIPES 75 mM NaCl, 2.5% Sucrose, pH 6.5 | 8.47E+07 | 6 | 1.08E+08 | 127.4 | 108.9 |
|  | 9.93E+07 | 6 | 8.99E+07 | 90.5 |  |
| 20 mM Histidine 100 mM NaCl, 2.5% Sucrose, pH 6.5 | 7.78E+07 | 9 | 5.85E+07 | 75.1 | 80.9 |
|  | 7.40E+07 | 9 | 6.41E+07 | 86.6 |  |
| 20 mM HEPES 75 mM NaCl, 2.5% Sucrose, pH 7.0 | 7.44E+07 | 9 | 7.35E+07 | 98.8 | 117.6 |
|  | 5.07E+07 | 9 | 6.92E+07 | 136.4 |  |
| 20 mM Citrate 75 mM NaCl, 2.5% Sucrose, pH 6.5 | 1.06E+08 | 9 | 1.16E+08 | 109.3 | 104.3 |
|  | 1.12E+08 | 9 | 1.11E+08 | 99.2 |  |
| 20 mM PIPES 75 mM NaCl, 2.5% Sucrose, pH 6.5 | 8.47E+07 | 9 | 1.05E+08 | 123.9 | 102.8 |
|  | 9.93E+07 | 9 | 8.13E+07 | 81.8 |  |

Fig. 26: Examples of selected stabilizing buffer conditions with carbohydrate

| Conditions | % TU retained (3rd F/T) | % TU retained (6th F/T) | % TU retained (9th F/T) |
|---|---|---|---|
| 20 mM Histidine, 100 mM NaCl, 2.5% Sucrose, pH 6.5 | 85.8 | 77.6 | 80.9 |
| 20 mM HEPES, 75 mM NaCl, 2.5% Sucrose, pH 7.0 | 101.0 | 119.2 | 117.6 |
| 20 mM PIPES, 75 mM NaCl, 2.5% Sucrose, pH 6.5 | 98.8 | 108.9 | 102.8 |
| 20 mM Citrate, 75 mM NaCl, 2.5% Sucrose, pH 6.5 | 117.2 | 110.0 | 104.3 |

Fig. 27: Viral titers in primary T cells

| Description | TU/ml | Average TU/ml |
|---|---|---|
| GFP Vector | 3.12E+07 | |
| | 3.25E+07 | |
| | 3.50E+07 | 3.29E+07 |
| | 2.76E+07 | |
| | 2.26E+07 | |
| 20 mM His, 100 mM NaCl, 2.5% Sucrose, pH 6.5 | 2.65E+07 | 2.56E+07 |
| | 3.63E+07 | |
| | 3.59E+07 | |
| 20 mM Citrate, 75 mM NaCl, 2.5% Sucrose, pH 6.5 | 3.76E+07 | 3.66E+07 |
| | 2.86E+07 | |
| | 2.40E+07 | |
| 20 mM HEPES, 75 mM NaCl, 2.5% Sucrose, pH 6.5 | 3.05E+07 | 2.77E+07 |
| | 3.70E+07 | |
| | 3.41E+07 | |
| 20 mM PIPES, 75 mM NaCl, 2.5% Sucrose, pH 6.5 | 3.25E+07 | 3.46E+07 |
| | 9.43E+06 | |
| Lentigen Vector | 1.19E+07 | 1.05E+07 |
| | 1.02E+07 | |

Fig. 28: Stability data comparison

| | | | |
|---|---|---|---|
| Extent of Aggregation (25 vs. 50°C) Average Rh of 4 conditions / given pH | Low 85.8 – 93.3 nm | High 84.9 – 114.8 nm | Moderate 96.9 – 98.8 nm |
| Activity at High Temperature (25 vs. 50°C) Average TU/mL of 4 conditions / given pH | High 3.5E+08 – 5.54E+07 TU/mL | Low 3.43E+08 – 0 (No activity) TU/mL | Moderate 3.5E+08 – 3.18E+07 TU/mL |
| Freeze-Thaw Stability after 9 cycles in selected Formulation with 2.5% Sucrose | High 102.8% | High 117.6% | Moderate 80.9% |
| Transduction of Final Formulation with 2.5% Sucrose on primary T lymphocytes | High 3.46E+07 TU/mL | Moderate 2.77E+07 TU/mL | Moderate 2.56E+07 TU/mL |

Fig. 29: Purification of lentiviral vector in PIPES, histidine, and HEPES buffers

| Process Step | Volume (mL) | TU/mL | Total TU | Step Recovery (%TU) |
|---|---|---|---|---|
| Millipak-20: PIPES Buffer<br>• Area: 0.01 m²<br>• Flow rate: 20 mL/min<br>• Buffer Flush: 2 L / m²<br>• Tubing Size: 25 | 61 | 1.22 E+08 | 3.06 E+10 | 81% |
| Millipak-20: Histidine Buffer<br>• Area: 0.01 m²<br>• Flow rate: 20 mL/min<br>• Buffer Flush: 2 L / m²<br>• Tubing Size: 25 | 60 | 1.08 E+08 | 2.67 E+10 | 58% |
| Millipak-20: HEPES Buffer<br>• Area: 0.01 m²<br>• Flow rate: 20 mL/min<br>• Buffer Flush: 2 L / m²<br>• Tubing Size: 25 | 61 | 1.30 E+08 | 3.26 E+10 | 72% |

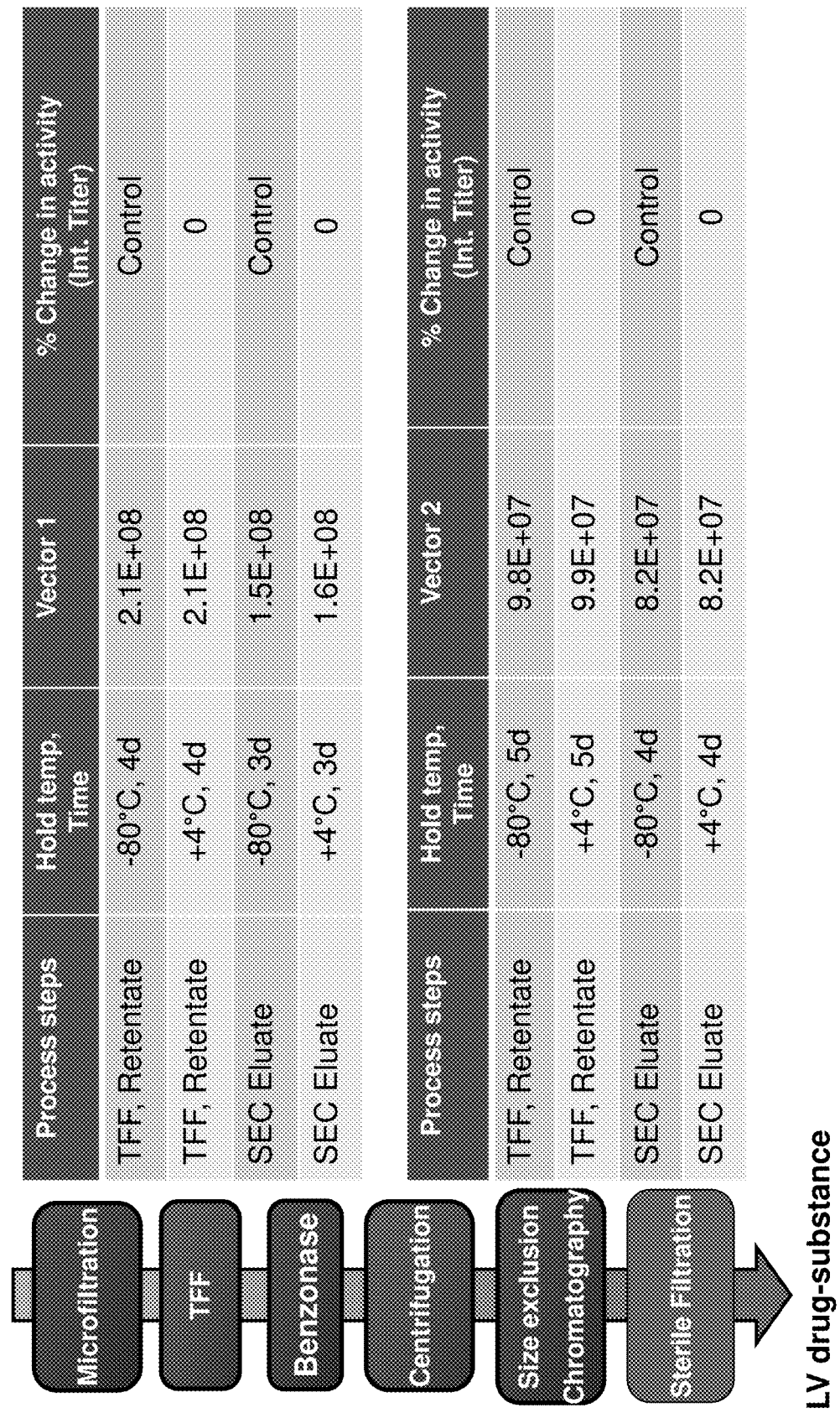
Fig. 30: Stability study of additional lentiviral vectors – short term storage of TFF and SEC samples

Fig. 31: Dynamic light scattering analysis of lentiviral vector aggregation

| Rep | Sample | Z-Avrg (d,nm) | PDI | SD | CV | %CV |
|---|---|---|---|---|---|---|
| 1 | Vector 1 | 139.1 | 0.108 | 58.90 | 0.42 | 42.3 |
| 1 | Vector 1 - 10x diluted | 142.6 | 0.038 | 30.17 | 0.21 | 21.2 |
| 2 | Vector 1 | 140.3 | 0.089 | 53.53 | 0.38 | 38.2 |
| 2 | Vector 1 - 10x diluted | 141.9 | 0.042 | 30.10 | 0.21 | 21.2 |
| 3 | Vector 1 | 140.3 | 0.101 | 56.87 | 0.41 | 40.5 |
| 3 | Vector 1 - 10x diluted | 143.9 | 0.045 | 29.57 | 0.21 | 20.5 |

Combined Result

| Sample | Z-Avrg (d,nm) | PDI | SD | CV | %CV |
|---|---|---|---|---|---|
| Vector 1 | 139.8 | 0.099 | 56.43 | 0.40 | 40.4 |
| Vector 1 - 10x diluted | 142.2 | 0.042 | 29.94 | 0.21 | 21.1 |

Fig. 32: Dynamic light scattering analysis of lentiviral vector aggregation

| Rep | Sample | Z-Avrg (d,nm) | PDI | SD | CV | %CV |
|---|---|---|---|---|---|---|
| 1 | Vector 2 | 142.5 | 0.108 | 51.67 | 0.36 | 36.3 |
| 1 | Vector 2 - 10x diluted | 140.5 | 0.073 | 35.67 | 0.25 | 25.4 |
| 2 | Vector 2 | 142.9 | 0.133 | 42.73 | 0.30 | 29.9 |
| 2 | Vector 2 - 10x diluted | 142.1 | 0.113 | 35.67 | 0.25 | 25.1 |
| 3 | Vector 2 | 140.7 | 0.149 | 51.63 | 0.37 | 36.7 |
| 3 | Vector 2 - 10x diluted | 142.9 | 0.085 | 32.30 | 0.23 | 22.6 |

Combined Result

| Sample | Z-Avrg (d,nm) | PDI | SD | CV | %CV |
|---|---|---|---|---|---|
| Vector 2 | 142 | 0.13 | 48.68 | 0.34 | 34.3 |
| Vector 2 - 10x diluted | 141.9 | 0.09 | 34.54 | 0.24 | 24.3 |

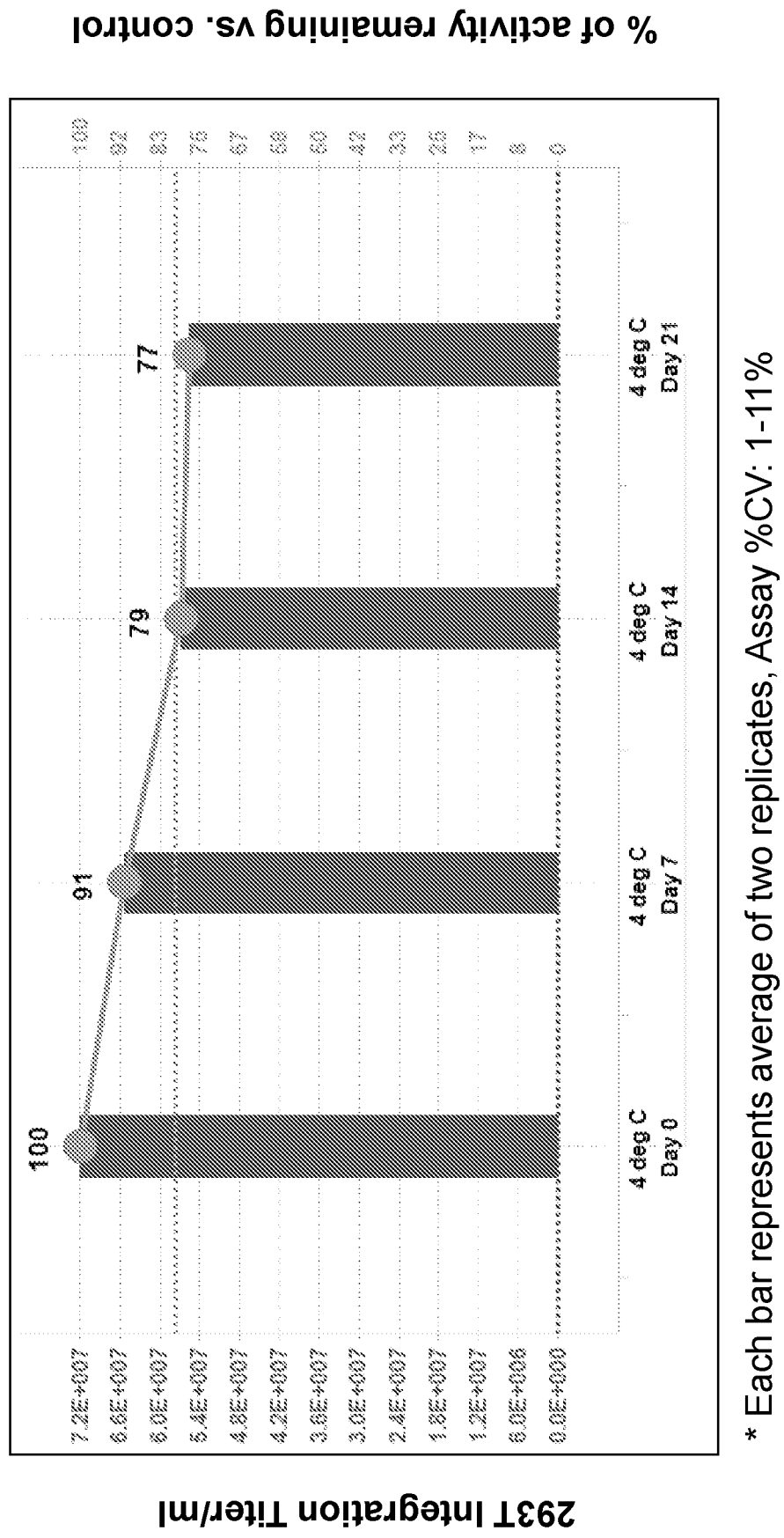
Fig. 33: Stability in long-term storage

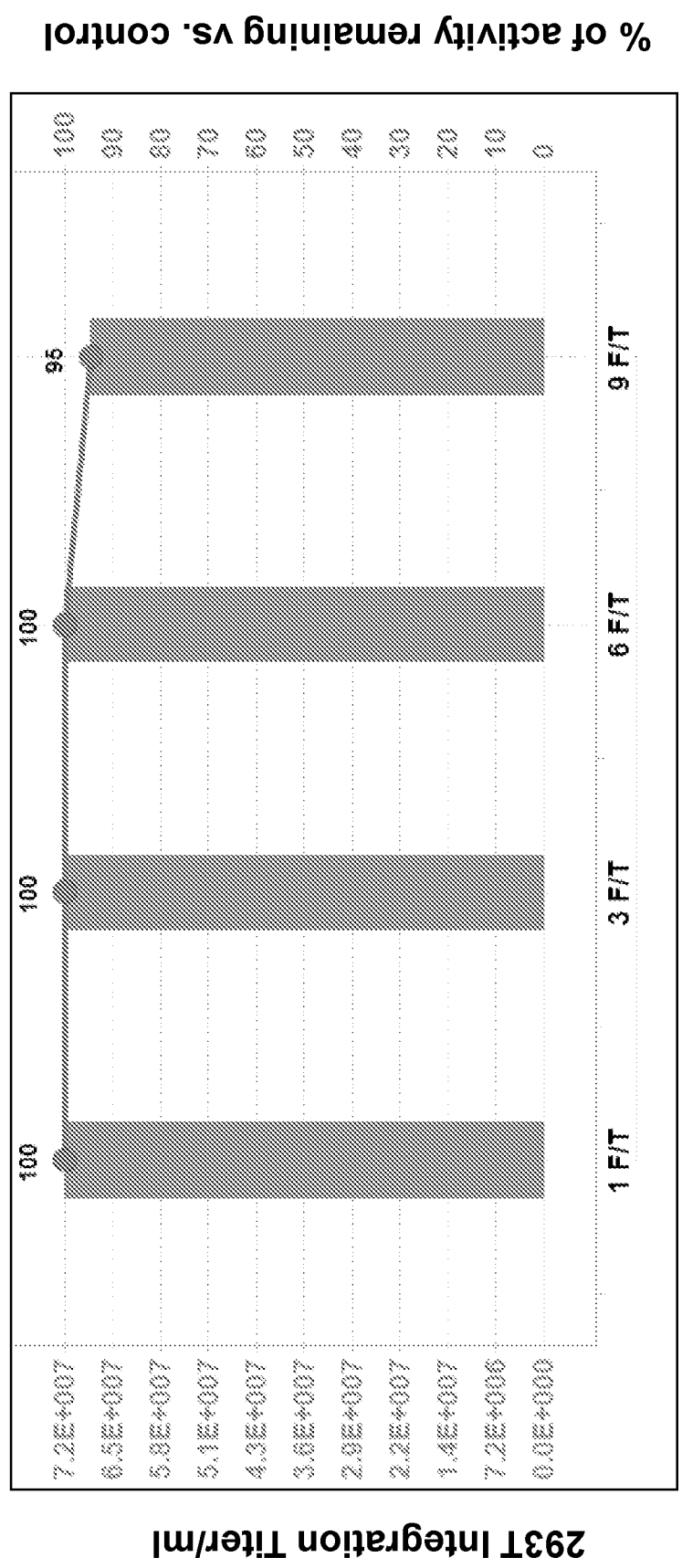
Fig. 34: Lentiviral vector stability after multiple freeze-thaw cycles
* Each bar represents average of two replicates, Assay %CV: 4-22%

BUFFERS FOR STABILIZATION OF LENTIVIRAL PREPARATIONS

FIELD OF THE INVENTION

The invention relates to lentiviral preparations that exhibit improved transducing capabilities and storage stability, as well as to methods of heterologous gene expression in target cells.

BACKGROUND OF THE INVENTION

With advances in gene therapy technologies, the use of therapeutic viral vectors represents an increasingly effective paradigm for treating human diseases. Among the viral vectors available for gene therapy applications are lentiviral vectors. Such vectors include reconstructed viral vector systems derived from human immunodeficiency virus-1 (HIV-1) and are capable of introducing a gene of interest into animal and human primary cells or cell lines. The genomes of lentiviral vectors include a coding strand of RNA, which is reverse-transcribed into DNA upon entering the cytoplasm of a host cell by a viral reverse transcriptase so as to form a DNA pre-integration complex. This complex is transported into the nucleus of the host cell, where a portion of the viral DNA is subsequently integrated into the host cell genome. The integrated DNA can then be transcribed into RNA, such as protein-coding mRNA, which can ultimately be exported to the cytoplasm for subsequent expression of a protein of interest.

Lentiviral vector-mediated gene expression can be used to achieve continuous and stable protein production, because the gene of interest has been integrated into a host cell's genome and is thus replicated upon division of the cell. Lentiviral vectors can effectively infect non-dividing cells as well as those actively progressing through the cell cycle. In contrast, other viral vectors, such as adenoviral vectors, adeno-associated viral vectors, and classical retroviral vectors, are only capable of infecting dividing cells. Tissues and cells in which lentiviral vector-mediated chronic expression of a gene of interest can occur include the brain, liver, muscle cells, retina, hematopoietic stem cells, marrow mesenchymal stem cells, and macrophages, among others.

The production of lentiviral vectors has been hindered by several challenges, one of which is low stability of the vectors. The manufacturing operation of lentiviral vectors includes several steps: production, purification, storage, and application of gene transfer (Carmo et al., J. Gene Med. 11:670-678, 2009). Lentiviral vectors are susceptible to inactivation during these processes, which can contribute to diminished final quality and efficacy of the vector preparation. In previous studies, it has been shown that one mechanism by which viral vectors are inactivated is by the loss of viral capacity to perform reverse transcription (Carmo et al., Hum. Gene Ther. 20:1168-76, 2009; and Carmo et al., J. Gene Med. 10:383-391, 2008). Moreover, there remains a need for methods to stabilize lentiviral vector preparations so as to prevent irreversible aggregation that can be accompanied by loss of infectivity. Additionally, during the purification of lentiviral vectors, stabilizing components are removed from the lentiviral preparation, which can cause the vector to become increasingly unstable. Therefore, there is also a need for lentiviral formulations that preserve vector stability throughout the purification process.

During purification and storage, vectors are often stored at 4° C. (Rodrigues et al., J. Biotechnol. 127:520-541, 2007). It has been reported that lentiviral vectors have an additional need for stabilizing components, such as human serum albumin (HSA) (Carmo et al., J. Gene Med. 11:670-678, 2009). This is in sharp contrast to gamma-retroviruses, where simply adding exogenous proteins brings back the stability comparable to cell culture supernatant. Lipoproteins are complex structures composed of several lipids, including cholesterol, phospholipids, and proteins (Olson, J. Nutr. 128:S439-S443, 1998). They act as lipid transporters in blood along with HSA. It is possible that a lipoprotein-HSA structure forms a protective arrangement around the membrane of lentiviral vectors (Carmo et al., J. Gene Med. 11:670-678, 2009). Because albumin is also known to associate tightly with cell surfaces (Dziarski et al., J. Biol. Chem. 269:20431-20436, 1994), these lipoprotein/HSA complexes can associate with the membrane of the vector, which is similar to a cell membrane. This association may provide protection to their structure and prevent conformational changes more efficiently than HSA alone.

In order to ensure stability during storage, stocks of infective viral vectors have commonly been stored at low temperatures (e.g., at −80° C.) due to their complexity. It has been suggested that lipid-enveloped viruses survive well at temperatures below −60° C., and that storage at −20° C. or 4° C. should only be used if "retention of virus infectivity is not essential" (Gould et al., Mol. Biotechnol. 13:57-66, 1999). Other investigations have concluded that certain viral vectors should be stored at −70° C. or lower in order to retain infectivity (Harper, Virology Ed. BIOS Scientific Publishers Limited, Oxford, UK, 1993). Typically, lentiviral vector preparations contain proteins encoded by the viral genome, including envelope proteins embedded in a lipid bilayer membrane. At low temperatures, the protein can be susceptible to denaturation and the lipid bilayer may be prone to loss of structural integrity. Therefore, a need exists for lentiviral formulations capable of increasing the stability of a viral vector preparation at a low temperature, for extended periods of time.

Lentiviral vectors are often maintained at these low temperatures for long-term storage, as iterative freezing and thawing of viral vectors can lead to a loss of transducing capacity. As such, there remains a need for lentiviral preparations that retain infectivity after undergoing multiple freeze/thaw cycles.

In addition to stability during purification and storage, a lentiviral vector useful for ex vivo applications, such as chimeric antigen receptor T (CART) cell therapy, desirably will retain stability at physiologically relevant temperatures, such as 37° C., the temperature at which lentiviral vectors may be incubated with host cells in order to promote transduction. Therefore, there also exists a need for lentiviral preparations that maintain structural integrity of the viral vector during gene transfer events ex vivo.

In addition to the above-noted biological considerations, lentiviral vector preparations that preserve viral vector stability can additionally be useful from a commercial perspective. When a recombinant lentiviral vector is stored at low temperatures for excessive periods of time or when the recombinant vector undergoes multiple freeze/thaw cycles during experimental use or manufacturing operations, the biological activity decreases significantly. This leads to a diminished recovery of infectious particles, further raising the cost of goods (COGs). In addition, a higher susceptibility of vector particles to lose activity can lead to inaccurate results in preclinical or clinical studies. For a clinical setting, use of an ultra-low temperature (e.g., −60° C. or below) storage device is an additional cost burden and poses a logistical challenge in hospitals and other point-of-care facilities. Generally, these facilities are expected to have an ultra-low freezing apparatus to deliver the treatment. Therefore, there remains a need for recombinant lentiviral vector preparations that preserve vector stability so as to promote efficient manufacturing operations and viable low-temperature storage methods.

SUMMARY OF THE INVENTION

The invention provides aqueous compositions that each include a lentiviral vector, a 1,4-piperazinediethanesulfonic acid (PIPES) buffer, and a salt.

In various embodiments, the PIPES buffer is present at a concentration of from about 10 to about 50 mM (e.g., about 20 mM); the pH of the aqueous composition is from about 6.0 to about 7.0 (e.g., about 6.5); and/or the salt is selected from the group consisting of sodium chloride, magnesium chloride, and calcium chloride. The concentration of the salt in the aqueous compositions can be, e.g., from about 25 mM to about 150 mM (e.g., about 50 mM or about 75 mM). In particular embodiments, the aqueous compositions include a lentiviral vector, 20 mM PIPES, and 75 mM sodium chloride, and have a pH of about 6.5.

The aqueous compositions can further include a carbohydrate, for example, a non-reducing carbohydrate, e.g., sucrose or trehalose. In various embodiments, the carbohydrate is present at a concentration of from about 1% to about 10% (e.g., from about 2% to about 5%, or about 2.5%) by weight per volume of the aqueous composition. In particular embodiments, the aqueous compositions include a lentiviral vector, 20 mM PIPES, 75 mM sodium chloride, and 2.5% sucrose by weight per volume of the aqueous composition, and the aqueous composition has a pH of about 6.5.

In various embodiments, the osmolality of the aqueous compositions is from about 270 mOsm/kg to about 330 mOsm/kg (e.g., from about 275 mOsm/kg to about 300 mOsm/kg, or about 285 mOsm/kg), and/or the lentiviral vector is present at a concentration of from about $2 \times 10^8$ transducing units per milliliter (TU/mL) to about $1 \times 10^9$ TU/mL (e.g., about $3 \times 10^8$ TU/mL to about $5 \times 10^8$ TU/mL).

The lentiviral vectors can be recombinant human immunodeficiency viruses (e.g., HIV-1) and, optionally, can include a vesicular stomatitis virus G (VSV-G) protein (e.g., present on the surface of the lentiviral vectors). Furthermore, the lentiviral vectors can include one or more transgenes, including, for example, transgenes that encode proteins (e.g., one or more chimeric antigen receptors (CARs)).

In various embodiments, the CARs each include, in an N-terminal to C-terminal direction, an antigen binding domain, a transmembrane domain, and one or more signaling domains. The signaling domains can include one or more primary signaling domains (e.g., a CD3-zeta stimulatory domain) and/or one or more costimulatory signaling domains (e.g., an intracellular domain selected from a costimulatory protein selected from the group consisting of CD27, CD28, 4-1 BB (CD137), OX40, GITR, CD30, CD40, ICOS, BAFFR, HVEM, ICAM-1, lymphocyte function-associated antigen-1 (LFA-1), CD2, CDS, CD7, CD287, LIGHT, NKG2C, NKG2D, SLAMF7, NKp80, NKp30, NKp44, NKp46, CD160, B7-H3, and a ligand that specifically binds with CD83).

The antigen binding domain of the CARs can optionally be or include an scFv. Furthermore, the antigen binding domain can optionally bind to an antigen selected from the group consisting of CD19; CD123; CD22; CD30; CD171; CS-1; C-type lectin-like molecule-1, CD33; epidermal growth factor receptor variant III (EGFRvIII); ganglioside G2 (GD2); ganglioside GD3; TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2; mesothelin; Interleukin 11 receptor alpha (IL-11Ra); prostate stem cell antigen (PSCA); Protease Serine 21; vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3; transglutaminase 5 (TGS5); high molecular weight-melanoma-associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1, melanoma antigen recognized by T cells 1; Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TM-PRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like, Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In particular embodiments, the antigen binding domain binds to CD19, mesothelin, or CD123. In a further particular embodiment, the CAR includes an anti-CD19 antibody or a fragment thereof, a 4-1BB (CD137) transmembrane domain, and a CD3-zeta signaling domain.

In various embodiments, the aqueous compositions are free of one or more (e.g., all) proteins, e.g., one or more (e.g., all) of the proteins selected from the group consisting of human serum albumin (HSA), recombinant human serum albumin (rHSA), bovine serum albumin (BSA), and a lipoprotein; and/or the lentiviral vectors are produced in cells cultured in the absence of serum.

In certain embodiments, the lentiviral vectors are characterized by a hydrodynamic radius of 100±25 nm as measured by dynamic light scattering (DLS). For example, the lentiviral vectors may maintain a hydrodynamic radius of 100±25 nm within a temperature range of from 25° C. to 55° C.

In certain embodiments, the lentiviral vectors are characterized by a polydispersity of from 10% to 25%. For example, the lentiviral vectors may maintain a polydispersity of from 10% to 25% within a temperature range of from 25° C. to 55° C.

In various embodiments, the lentiviral vectors maintains a concentration after 3, 6, or 9 freeze/thaw cycles of from about 70% to about 100% relative to the concentration of the lentiviral vector in the aqueous composition prior to the freeze/thaw cycles, wherein each of the freeze/thaw cycles includes freezing the aqueous composition and subsequently allowing the aqueous composition to thaw at room temperature.

The invention also provides aqueous compositions that each include a lentiviral vector, a buffer selected from the group consisting of a phosphate buffer, a sodium citrate buffer, a 2-(N-morpholino)ethanesulfonic acid (MES) buffer, a 3-morpholinopropane-1-sulfonic acid (MOPS) buffer, and a salt (e.g., sodium chloride, magnesium chloride, or calcium chloride). These compositions can further include a carbohydrate, for example, a non-reducing carbohydrate (e.g., sucrose or trehalose).

The invention further includes dried or lyophilized compositions, which are prepared by drying or lyophilizing the aqueous compositions described herein, as well as aqueous compositions that are prepared by reconstituting such dried or lyophilized compositions in a buffer described herein (or another, standard vehicle for administration).

Also included in the invention are methods of purifying lentiviral vectors. In these methods, an aqueous composition as described herein is passed through a filter, thereby producing an aqueous composition that is substantially free of microorganisms. In various embodiments, the filter includes a plurality of pores, e.g., pores having a diameter of about 0.2 µm. In various embodiments, an aqueous composition that is substantially free of microorganisms includes the lentiviral vector at a concentration of about 80% relative to the concentration of the lentiviral vector in the aqueous composition prior to the contacting.

The invention also provides methods of purifying lentiviral vectors, including (a) contacting an aqueous composition as described herein with a material including a plurality of particles; and (b) separating substances that flow through the material from substances that remain within the material, thereby producing an aqueous composition that is enriched with the lentiviral vector.

Further, the invention provides methods of purifying lentiviral vectors, including contacting an aqueous composition as described herein with a nuclease, thereby producing an aqueous composition that is substantially free of contaminating polynucleotides.

Also provided in the invention are methods of expressing one or more transgenes in a cell, which include contacting the cell with an aqueous composition as described herein. In various embodiments, the cell is a mammalian cell (e.g., a T cell, such as a human T cell). In specific embodiments, the cell is a 293T cell, a Jurkat T cell, or a primary human T cell.

The invention also includes kits that include an aqueous composition as described herein and optionally a package insert, e.g., a package insert that instructs a user of the kit to express a transgene in a cell according to a method as described herein. The kits optionally can further include one or more reagents that can be used to culture a cell as described herein.

The invention further includes the use of an aqueous composition as described herein in methods for delivering a viral vector, which optionally includes a transgene, into a cell of a subject, the method involving administering the composition to the subject. Methods of preventing or treating disease or conditions, e.g., as described herein, and/or delivering transgenes (e.g., genes encoding CARS), e.g., as described herein, are also included in the invention, and can involve administration of the compositions described herein.

Definitions

As used herein, the term "about" refers to a value that is within 10% above or below the value being described. For instance, a value of "about 50 mM" denotes a concentration of from 45 mM to 55 mM.

As used herein, the term "buffer" refers to a mixture of a weak acid and its conjugate base or a weak base and its conjugate acid. For instance, as used herein, a "1,4-piperazinediethanesulfonic acid buffer" refers to a mixture that includes 1,4-piperazinediethanesulfonic acid and the 1,4-piperazinediethanesulfonate anion (e.g., sodium 1,4-piperazinediethanesulfonate). Likewise, a "sodium citrate buffer" as used herein refers to a mixture that includes sodium citrate, as well as its conjugate acid, citric acid. Due to the chemical equilibrium that is established between a weak acid and its conjugate base, a solution containing a buffer resists abrupt changes in pH upon the addition of small quantities of acid or base to the solution.

As used herein, the term "contaminating polynucleotide" refers to a polynucleotide not derived from a lentiviral vector. Contaminating polynucleotides may include, e.g., non-lentiviral polynucleotides derived from a cell in which the lentiviral vector was produced, such as chromosomal mammalian DNA (e.g., human DNA) that is not included within a transgene or other component of a lentiviral vector.

As used herein, the term "freeze/thaw cycle" refers to exposure of a liquid mixture, such as an aqueous solution or suspension, to a temperature at or less than its freezing point until the mixture is frozen, followed by thawing the mixture at a temperature greater than its freezing point. The freezing step can be performed, e.g., by placing the mixture in an environment in which the temperature is from about −80° C. to about −20° C. The mixture can remain frozen, e.g., for a period of one or more days, weeks, months, or years prior to thawing. The thawing step can be performed by exposing the mixture to conditions in which the temperature is from about 2° C. to about 8° C., or by storing the mixture at room temperature (e.g., the ambient temperature of a laboratory, or about 25° C.). Alternatively, thawing can take place by use of a water bath (e.g., at 37° C.).

As used herein, the term "hydrodynamic radius" refers to the apparent radius ($R_h$, in nm) of a particle in a solution as inferred from the diffusional characteristics of the particle. The hydrodynamic radius of a viral particle is one factor that dictates the rate of diffusion of the viral particle in aqueous solution, as well as the ability of the particle to migrate in gels of macromolecules. The hydrodynamic radius of a viral particle is determined in part by the mass and molecular structure of each of the components of the particle, as well as its hydration state. Methods for determining the hydrodynamic radius of a viral particle are well known in the art, and include the use of dynamic light scattering and size exclusion chromatography.

As used herein, the term "non-reducing carbohydrate" refers to a carbohydrate that does not exist in a state of chemical equilibrium with an aldehyde, and thus lacks the ability to be oxidized to a carboxylic acid by transition metal cations, such as silver ($Ag^+$) and copper ($Cu^{2+}$). Exemplary non-reducing carbohydrates include, without limitation, disaccharides such as sucrose, trehalose, and palatinitol, trisaccharides such as raffinose and melezitose, as well as tetrasaccharides such as stachyose. Non-reducing carbohydrates additionally include monosaccharide derivatives such as sorbitol, mannitol, erythritol, and xylitol, disaccharide derivatives such as lacitol and maltitol, aldonic acids and their lactones such as gluconic acid, gluconic acid γ-lactone, aldaric acids and their lactones such as ribaraic acid, arabinaric acid, and galactaric acid, uronic acids such as glucuronic acid, galacuronic acid, and itiannuronic acid, ester derivatives such as trehalose octaacetate, sucrose octaacetate, and cellobiose octaacetate, and ether derivatives in which hydroxyl groups are O-alkylated. Non-reducing carbohydrates include those that have a D or L stereochemical orientation.

As used herein, the term "osmolality" refers to a measure of the osmotic pressure of dissolved solute particles in an aqueous solution. The solute particles include both ions as well as non-ionized molecules. Osmolality is expressed as the concentration of osmotically active particles (i.e., osmoles) dissolved in 1 kg of solvent (i.e., water). Osmolality is expressed herein in units of milliosmoles per 1 kg of water (mOsm/kg).

As used herein, the term "percent by weight per volume" or "% w/v" denotes the percentage weight (in grams) of a single component relative to the total volume of the mixture that contains the component. For instance, 500 mg of a component in a total volume of 8 ml is 6.25% w/v, and 500 mg of a component in a total volume of 5 ml is 10% w/v.

As used herein, the term "polydispersity" refers to the degree of homogeneity of the sizes of particles, such as lentiviral particles, within a sample. A higher polydispersity indicates less homogeneity and a lower polydispersity indicates a higher level of homogeneity. For instance, when the level of homogeneity is high, lentiviral particles can be considered to be approaching identical sizes and are thus monodisperse. As will be understood by one of ordinary skill in the art, as the polydispersity decreases, the level of homogeneity increases. As such, a lower polydispersity indicates a higher level of homogeneity. For example, a formulation with 15% polydispersity has less homogeneity than a formulation with 10% polydispersity. When the level of homogeneity is low, the particle population can be considered to contain significantly different sizes and thus be polydisperse.

As used herein, the term "scFv" refers to a single chain Fv antibody in which the variable domains of the heavy chain and the light chain from an antibody have been joined to form one chain. scFv fragments contain a single polypeptide chain that includes the variable region of an antibody light chain (VL) (e.g., CDR-L1, CDR-L2, and/or CDR-L3) and the variable region of an antibody heavy chain (VH) (e.g., CDR-H1, CDR-H2, and/or CDR-H3) separated by a linker. The linker that joins the VL and VH regions of a scFv fragment can be a peptide linker composed of proteinogenic amino acids. Alternative linkers can be used to so as to increase the resistance of the scFv fragment to proteolytic degradation (e.g., linkers containing D-amino acids), in order to enhance the solubility of the scFv fragment (e.g., hydrophilic linkers such as polyethylene glycol-containing linkers or polypeptides containing repeating glycine and serine residues), to improve the biophysical stability of the molecule (e.g., a linker containing cysteine residues that form intramolecular or intermolecular disulfide bonds), or to attenuate the immunogenicity of the scFv fragment (e.g., linkers containing glycosylation sites). ScFv molecules are known in the art and are described, e.g., in U.S. Pat. No. 5,892,019; Flo et al. (Gene 77:51, 1989); Bird et al. (Science 242:423, 1988); Pantoliano et al. (Biochemistry 30:10117, 1991); Milenic et al. (Cancer Research 51:6363, 1991); and Takkinen et al. (Protein Engineering 4:837, 1991). The VL and VH domains of an scFv molecule can be derived from one or more antibody molecules. It will also be understood by one of ordinary skill in the art that the variable regions of the scFv molecules of the invention can be modified such that they vary in amino acid sequence from the antibody molecule from which they were derived. For example, in one embodiment, nucleotide or amino acid substitutions leading to conservative substitutions or changes at amino acid residues can be made (e.g., in CDR and/or framework residues). Alternatively or in addition, mutations are made to CDR amino acid residues to optimize antigen-binding using art-recognized techniques. ScFv fragments are described, for example, in WO 2011/084714; incorporated herein by reference.

As used herein, the phrases "specifically binds" and "binds" refer to a binding reaction which is determinative of the presence of a particular protein in a heterogeneous population of proteins and other biological molecules that is recognized, e.g., by a ligand with particularity. A ligand (e.g., a protein, proteoglycan, or glycosaminoglycan) that specifically binds to a protein will bind to the protein with a $K_D$ of less than 500 nM. For example, a ligand that specifically binds to a protein will bind to the protein with a $K_D$ of up to 500 nM (e.g., between 1 pM and 500 nM). A ligand that does not exhibit specific binding to a protein or a domain thereof will exhibit a $K_D$ of greater than 500 nM (e.g., greater than 600 nm, 700 nM, 800 nM, 900 nM, 1 µM, 100 µM, 500 µM, or 1 mM) for that particular protein or domain thereof. A variety of assay formats may be used to determine the affinity of a ligand for a specific protein. For example, solid-phase ELISA assays are routinely used to identify ligands that specifically bind a target protein. See, e.g., Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), for a description of assay formats and conditions that can be used to determine specific protein binding.

As used herein, the term "transgene" may refer to a nucleic acid sequence that encodes a protein or functional RNA product that is not naturally expressed in the cell into which the transgene is to be introduced. Alternatively, a transgene may be homologous to an endogenous gene of the cell into which the transgene is to be introduced, but is designed to be inserted into the genome of the target cell so as to alter the genome of the cell into which it is inserted. For instance, a transgene may be homologous to an endogenous gene of a target cell, but is to be inserted at a location within the genome of the target cell that differs from the location of the naturally occurring gene.

As used herein, the term "vesicular stomatitis virus G protein" or "VSV-G protein" refers to an isolated polypeptide having substantial homology to the G protein of vesicular stomatitis virus. A polypeptide has substantial homology to the VSV-G protein, e.g., if it exhibits the membrane-fusing properties of the wild-type VSV-G protein. A VSV-G protein may be, e.g., the full-length VSV-G protein or a polypeptide that contains fragments thereof, as long as the polypeptide retains the ability to associate with nucleic acid-lipid particles and facilitate transfection.

As used herein, the term "viral titer" refers to the number of infectious vector particles, or "transducing units," that result in the production of a transgene product in a target cell. Viral titer can be measured by a functional assay, such as an assay described in Xiao et al., Exp. Neurobiol. 144: 113-124, 1997, or Fisher et al., J. Virol. 70:520-532, 1996, the disclosures of both of which are incorporated herein by reference. Alternatively, viral titer can be measured by determining the quantity of viral DNA that has integrated into a host cell genome, e.g., using polymerase chain reaction (PCR) techniques known in the art.

As used herein, the term "viral vector" refers to a viral particle which has a capability of introducing a nucleic acid molecule into a host. "Lentiviral vectors" includes viral vectors that include sequences derived from HIV-1. A lentiviral vector carrying an exogenous gene(s) is packaged into an infectious virus particle via virus packaging with the aid of packaging plasmids using specific cell-lines. The infectious virus particle infects a cell to achieve expression of the exogenous gene. A "recombinant" viral vector refers to a viral vector constructed by gene recombinant technologies. A recombination viral vector can be constructed using methods known in the art, such as by transducing a packaging cell-line with a nucleic acid encoding the viral genome and subsequently isolating newly packaged viral particles.

BRIEF DESCRIPTION OF THE FIGURES

FIG. 1 is a flow chart illustrating strategies for the identification of buffers capable of stabilizing lentiviral preparations. A tiered approach (left) to buffer identification involves conducting stability assays, such as dynamic light scattering (DLS), and determining lentiviral titer (in transducing units, TU) in cells transduced with lentiviral vectors, optionally after one or more freeze/thaw (F/T) cycles, in order to sample a wide range of buffer, salt, and pH conditions and to gradually select for conditions that optimally promote storage stability and transduction capacity. In a parallel approach (right), various lentiviral preparation conditions are sampled simultaneously, and the conditions that most effectively prevent lentiviral aggregation and preserve infectivity are subsequently chosen, e.g., for chimeric antigen receptor T-cell (CART) applications.

FIG. 2 is a graph showing the lentiviral titer (in TU/mL) of cells transduced with lentiviral preparations containing various buffers and salts and exhibiting a range pH values from 6.0 to 8.0.

FIG. 3 is a series of graphs illustrating different hydrodynamic radius distributions. A monomodal monodisperse distribution (top) is characterized by a single species that is likely to be a lentiviral monomer. A monomodal polydisperse distribution (middle) typically indicates multiple species that often cannot be resolved by dynamic light scattering, and may be a manifestation of an increased presence of aggregating lentiviral particles relative to a monomodal monodisperse distribution. A polymodal polydisperse distribution (bottom) indicates multiple aggregated species of lentiviral particles that can be resolved by dynamic light scattering.

FIG. 4 is a series of graphs demonstrating the effect of an increase in temperature on the hydrodynamic radius and polydispersity of lentiviral preparations containing a histidine buffer.

FIG. 5 is a series of graphs demonstrating the effect of an increase in temperature on the hydrodynamic radius and polydispersity of lentiviral preparations containing a PIPES buffer.

FIG. 6 is a series of graphs demonstrating the effect of an increase in temperature on the hydrodynamic radius and polydispersity of lentiviral preparations containing a sodium citrate buffer.

FIG. 7 is a series of graphs demonstrating the effect of an increase in temperature on the hydrodynamic radius and polydispersity of lentiviral preparations containing a HEPES buffer.

FIG. 8 is a series of graphs demonstrating the effect of an increase in temperature on the hydrodynamic radius and polydispersity of lentiviral preparations containing a MOPS buffer.

FIG. 9 is a series of graphs demonstrating the effect of an increase in temperature on the hydrodynamic radius and polydispersity of lentiviral preparations containing a MES buffer.

FIG. 10 is a series of graphs demonstrating the effect of an increase in temperature on the hydrodynamic radius and polydispersity of lentiviral preparations containing a phosphate buffer.

FIG. 11 is a series of graphs demonstrating the effect of an increase in temperature on the hydrodynamic radius and polydispersity of lentiviral preparations containing a 3-[4-(2-hydroxyethyl)piperazin-1-yl]propane-1-sulfonic acid (HEPPS) buffer.

FIG. 12 is a series of graphs demonstrating the effect of an increase in temperature on the hydrodynamic radius and polydispersity of lentiviral preparations containing a 2-amino-2-hydroxymethyl-propane-1,3-diol (Tris) buffer.

FIG. 13 is a series of graphs demonstrating the effect of changes in pH and sodium chloride concentration on the hydrodynamic radii of lentiviral preparations containing histidine (top, left), citrate (top, middle), MOPS (top, right), PIPES (bottom, left), HEPES (bottom, middle), or MES (bottom, right) buffers. Conditions highlighted with a star designate pH values and salt concentrations that result in the highest lentiviral titer in transduction experiments performed at elevated temperatures (see, e.g., FIGS. 15 and 16).

FIG. 14 is a series of graphs demonstrating the effect of changes in pH and sodium chloride concentration on the hydrodynamic radii of lentiviral preparations containing phosphate (left), HEPPS (middle), and Tris (right) buffers. Conditions highlighted with a star designate pH values and salt concentrations that result in the highest lentiviral titer in transduction experiments performed at elevated temperatures (see, e.g., FIGS. 17 and 18).

FIG. 15 is a series of graphs demonstrating the effect of changes in pH and sodium chloride concentration on the transducing ability of lentiviral preparations containing a histidine (top) or a PIPES (bottom) buffer at elevated temperatures of 42° C. (as indicated by "$TU^{42}$") and 50° C. (as indicated by "$TU^{50}$"). $TU^{42}$ and $TU^{50}$ values shown denote the lentiviral titer of cells transduced with the indicated lentiviral preparation at the indicated temperature, expressed as a percentage of the lentiviral titer of cells transduced with the indicated lentiviral preparation at 37° C.

FIG. 16 is a series of graphs demonstrating the effect of changes in pH and sodium chloride concentration on the transducing ability of lentiviral preparations containing a citrate (top) or a HEPES (bottom) buffer at elevated temperatures of 42° C. (as indicated by "$TU^{42}$") and 50° C. (as indicated by "$TU^{50}$"). $TU^{42}$ and $TU^{50}$ values shown denote the lentiviral titer of cells transduced with the indicated lentiviral preparation at the indicated temperature, expressed as a percentage of the lentiviral titer of cells transduced with the indicated lentiviral preparation at 37° C.

FIG. 17 is a series of graphs demonstrating the effect of changes in pH and sodium chloride concentration on the transducing ability of lentiviral preparations containing a MOPS (top) or a MES (bottom) buffer at elevated temperatures of 42° C. (as indicated by "$TU^{42}$") and 50° C. (as indicated by "$TU^{50}$"). $TU^{42}$ and $TU^{50}$ values shown denote the lentiviral titer of cells transduced with the indicated lentiviral preparation at the indicated temperature, expressed as a percentage of the lentiviral titer of cells transduced with the indicated lentiviral preparation at 37° C.

FIG. 18 is a series of graphs demonstrating the effect of changes in pH and sodium chloride concentration on the transducing ability of lentiviral preparations containing a phosphate (top) or a HEPPS (bottom) buffer at elevated temperatures of 42° C. (as indicated by "$TU^{42}$") and 50° C. (as indicated by "$TU^{50}$"). $TU^{42}$ and $TU^{50}$ values shown denote the lentiviral titer of cells transduced with the indicated lentiviral preparation at the indicated temperature, expressed as a percentage of the lentiviral titer of cells transduced with the indicated lentiviral preparation at 37° C.

FIG. 19 is a series of graphs demonstrating the effect of changes in pH and sodium chloride concentration on the transducing ability of lentiviral preparations containing a Tris buffer at elevated temperatures of 42° C. (as indicated by "$TU^{42}$") and 50° C. (as indicated by "$TU^{50}$"). $TU^{42}$ and $TU^{50}$ values shown denote the lentiviral titer of cells transduced with the indicated lentiviral preparation at the indicated temperature, expressed as a percentage of the lentiviral titer of cells transduced with the indicated lentiviral preparation at 37° C.

FIG. 20 is a graph showing the capability of various lentiviral vector preparations to maintain infectivity in the absence of a carbohydrate after 3 (left), 6 (middle), or 9 (right) freeze/thaw cycles. Infectivity is measured as the quantity of transducing units of the lentiviral vector present in each preparation after the corresponding number of freeze/thaw cycles as a percentage of the quantity of transducing units present in the lentiviral vector preparation prior to the first freeze/thaw process.

FIG. 21 is a graph showing the relative infectivities of screened lentiviral vector preparations in the absence of a carbohydrate after 3, 6, or 9 freeze/thaw cycles. Infectivity is measured as the quantity of transducing units of the lentiviral vector present in each preparation after the corresponding number of freeze/thaw cycles as a percentage of the quantity of transducing units present in the lentiviral vector preparation prior to the first freeze/thaw process.

FIG. 22 is a table showing the relative infectivities of screened lentiviral vector preparations in the absence of a carbohydrate after 3, 6, or 9 freeze/thaw cycles. Infectivity is measured as the quantity of transducing units of the lentiviral vector present in each preparation after the corresponding number of freeze/thaw cycles as a percentage of the quantity of transducing units present in the lentiviral vector preparation prior to the first freeze/thaw process.

FIG. 23 is a table showing the relative infectivities of select lentiviral vector preparations in the absence of a carbohydrate after 3, 6, or 9 freeze/thaw cycles. Infectivity is measured as the quantity of transducing units of the lentiviral vector present in each preparation after the corresponding number of freeze/thaw cycles as a percentage of the quantity of transducing units present in the lentiviral vector preparation prior to the first freeze/thaw process.

FIG. 24 is a graph showing the capability of screened lentiviral vector preparations to maintain infectivity in the presence of a carbohydrate after 3, 6, or 9 freeze/thaw cycles. Infectivity is measured as the quantity of transducing units of the lentiviral vector present in each preparation after the corresponding number of freeze/thaw cycles as a percentage of the quantity of transducing units present in the lentiviral vector preparation prior to the first freeze/thaw process.

FIG. 25 is a table showing the relative infectivities of screened lentiviral vector preparations in the presence of a carbohydrate after 3, 6, or 9 freeze/thaw cycles. Infectivity is measured as the quantity of transducing units of the lentiviral vector present in each preparation after the corresponding number of freeze/thaw cycles as a percentage of the quantity of transducing units present in the lentiviral vector preparation prior to the first freeze/thaw process.

FIG. 26 is a table showing the relative infectivities of select lentiviral vector preparations in the presence of a carbohydrate after 3, 6, or 9 freeze/thaw cycles. Infectivity is measured as the quantity of transducing units of the lentiviral vector present in each preparation after the corresponding number of freeze/thaw cycles as a percentage of the quantity of transducing units present in the lentiviral vector preparation prior to the first freeze/thaw process.

FIG. 27 is a table showing the relative infectivities of select lentiviral preparations in primary T cells. Details regarding the measurement of lentiviral titer are provided in Example 7, below.

FIG. 28 is a table comparing the stability of a lentiviral vector in PIPES, HEPES, and histidine buffers, as assessed by extent of aggregation, activity at high temperature, freeze-thaw stability, and transduction of primary T lymphocytes.

FIG. 29 is a table showing the levels of lentivirus titer (% TU) maintained after purification under the indicated conditions, using a PIPES, histidine, or HEPES buffer.

FIG. 30 is a table showing the maintenance of titer of two different lentiviral vectors (1 and 2) purified in a PIPES-based buffer.

FIG. 31 shows dynamic light scattering (DLS) analysis of the aggregation status of a lentiviral vector (vector 1).

FIG. 32 shows dynamic light scattering (DLS) analysis of the aggregation status of a lentiviral vector (vector 2).

FIG. 33 is a graph showing the stability of a lentiviral vector (vector 2) after 0, 7, 14, and 21 days at 4° C.

FIG. 34 is a graph showing the stability of a lentiviral vector (vector 2) after 1, 3, 6, and 9 freeze-thaw cycles.

DETAILED DESCRIPTION

The present invention is based on the discovery that lentiviral preparations containing a PIPES buffer exhibit improved biological properties relative to lentiviral preparations containing a conventional lentiviral formulation buffer, such as HEPES. These improved biological characteristics include elevated resistance to aggregation across a range of temperatures and salt concentrations, improved transduction capacity at physiological and at elevated temperatures (such as 42° C. and 50° C.), and greater resistance to loss of infectivity during multiple freeze/thaw cycles. Other buffers useful in conjunction with lentiviral preparations of the invention include phosphate buffers, sodium citrate buffers, MES buffers, and MOPS buffers. Lentiviral preparations of the invention may optionally include a salt, such as sodium chloride, and may optionally contain a carbohydrate, such as a non-reducing carbohydrate (see below). As described herein, lentiviral vectors for use with the compositions and methods of the invention may include a transgene, e.g., a protein-encoding gene designed for integration into the chromosomal DNA of a host cell. Additionally, the lentiviral preparations described herein can be used in conjunction with purification techniques, such as filtration and chromatographic procedures, in order to purify lentiviral vectors with improved recovery. The methods of the invention also encompass processes for the transduction of host cells, such as mammalian cells (e.g., human T cells).

Lentiviral Preparation Components

Lentiviral vector preparations of the invention may include a variety of components, such as one or more salts and/or carbohydrates. Surprisingly, the lentiviral vector preparations described herein do not require an added protein component in order to promote viral stability. The compositions described herein can thus each optionally be characterized as lacking added protein components. A number of different types of albumin have been tested for their ability to promote stability of lentiviral vectors (e.g. bovine serum albumin (BSA), human serum albumin (HAS), and recombinant HSA (rHSA)). rHSA, for instance, has often been incorporated into lentiviral preparations, as it is produced in genetically modified yeast and thus provides a higher level of safety since it is not of animal origin (Chuang et al., Pharm. Res. 19:569-577, 2002). Through the use of the present invention, HSA and similar protein components can be avoided in lentiviral vector preparations, as these may interfere with analytical characterization of vectors. The present invention is unique in part because of the ability of the buffers described herein to impart stability to lentiviral vectors in the absence of added protein components. As is demonstrated, e.g., in FIG. 2-19, the buffers described herein can prevent viral aggregation, promote enhanced transduction capacity, and preserve infectivity following multiple freeze/thaw cycles. The compositions described herein can also, optionally, be characterized as including or lacking added carbohydrate components.

Lentiviral vector preparations of the invention may be aqueous mixtures, such as aqueous solutions or suspensions. Lentiviral vector preparations can optionally include a salt, such as sodium chloride, magnesium chloride, or calcium chloride. The salt may be present, e.g., at a concentration of from about 1 mM to about 1 M in the aqueous lentiviral preparation (e.g., 1 mM, 2 mM, 3 mM, 4 mM, 5 mM, 6 mM, 7 mM, 8 mM, 9 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 100 mM, 125 mM, 150 mM, 175 mM, 200 mM, 225 mM, 250 mM, 275 mM, 300 mM, 325 mM, 350 mM, 375 mM, 400 mM, 450 mM, 475 mM, 500 mM, 525 mM, 575 mM, 600 mM, 625 mM, 650 mM, 675 mM, 700 mM, 725 mM, 750 mM, 775 mM, 800 mM, 825 mM, 850 mM, 875 mM, 900 mM, 925 mM, 950 mM, 957 mM, or 1 M). In some embodiments, the concentration of salt is from about 25 mM to about 250 mM, about 50 mM to about 75 mM, about 50 mM to about 200 mM, or about 100 mM to about 150 mM (e.g., 25 mM, 30 mM, 35 mM, 40 mM, 45 mM, 50 mM, 55 mM, 60 mM, 65 mM, 70 mM, 75 mM, 80 mM, 85 mM, 90 mM, 100 mM, 125 mM, or 150 mM). In some embodiments, the concentration of salt may be 50 mM or 75 mM, as desired.

Lentiviral vector preparations described herein may exhibit a pH, e.g., of from about 5.0 to about 8.0, e.g., 6.0 to about 7.0 (e.g., 6.0, 6.1, 6.2, 6.3, 6.4, 6.5, 6.6, 6.7, 6.8, 6.9, or 7.0). In some embodiments, the pH of the lentiviral vector preparation is 6.5.

A lentiviral vector preparation of the invention may optionally contain a carbohydrate, such as a non-reducing carbohydrate as described herein. Exemplary non-reducing carbohydrates include sucrose and trehalose, among others. When included in a lentiviral vector preparation, a carbohydrate may be present at a concentration of, e.g., from about 1% to about 10%, from about 2.5% to about 10%, or from about 2.5% to about 5% by weight per volume (w/v) of the aqueous lentiviral preparation. For instance, a carbohydrate, such as a non-reducing carbohydrate described herein, can be present within an aqueous lentiviral preparation at a concentration of 1% w/v, 1.5% w/v, 2% w/v, 2.5% w/v, 3% w/v, 3.5% w/v, 4% w/v, 4.5% w/v, 5% w/v, 5.5% w/v, 6% w/v, 6.5% w/v, 7% w/v, 7.5% w/v, 8% w/v, 8.5% w/v, 9% w/v, 9.5% w/v, or 10% w/v.

A lentiviral vector may be present within a lentiviral preparation of the invention within a range of concentrations. For instance, a lentiviral vector may be present within a lentiviral preparation at a concentration of, e.g., from about $2 \times 10^8$ transducing units per milliliter (TU/mL) to about $1 \times 10^9$ TU/mL (e.g., $2 \times 10^8$ TU/mL, $2.5 \times 10^8$ TU/mL, $3 \times 10^8$ TU/mL, $3.5 \times 10^8$ TU/mL, $4 \times 10^8$ TU/mL, $4.5 \times 10^8$ TU/mL, $5 \times 10^8$ TU/mL, $5.5 \times 10^8$ TU/mL, $6 \times 10^8$ TU/mL, $6.5 \times 10^8$ TU/mL, $7 \times 10^8$ TU/mL, $7.5 \times 10^8$ TU/mL, $8 \times 10^8$ TU/mL, $8.5 \times 10^8$ TU/mL, $9 \times 10^8$ TU/mL, $9.5 \times 10^8$ TU/mL, or $1 \times 10^9$ TU/mL). When desirable, a lentiviral preparation may contain a lentiviral vector at a concentration of from about $3 \times 10^8$ TU/mL to about $5 \times 10^8$ TU/mL (e.g., $3 \times 10^8$ TU/mL, $3.5 \times 10^8$ TU/mL, $4 \times 10^8$ TU/mL, $4.5 \times 10^8$ TU/mL, or $5 \times 10^8$ TU/mL).

Transgene Expression

Lentiviral vectors for use with the compositions and methods of the invention may include a transgene, such as a protein-encoding transgene designed for integration into the chromosomal DNA of a target cell. Exemplary transgenes include those that encode a chimeric antigen receptor (CAR). The CAR may include several domains, such as an antigen binding domain, a transmembrane domain, and one or more signaling domains. In these cases, the signaling domains may contain one or more primary signaling domains (such as a CD3-zeta stimulatory domain) and/or one or more costimulatory signaling domains (such as CD27, CD28, 4-1BB (CD137), OX40, GITR, CD30, CD40, ICOS, BAFFR, HVEM, ICAM-1, lymphocyte function-associated antigen-1 (LFA-1), CD2, CDS, CD7, CD287, LIGHT, NKG2C, NKG2D, SLAMF7, NKp80, NKp30, NKp44, NKp46, CD160, B7-H3, or a ligand that specifically binds with CD83.

In certain cases, the transgene can include an antigen-binding domain (such as a scFv) that binds a particular target protein or carbohydrate. Exemplary antigens include CD19, CD123, CD22, CD30, CD171, CS-1, C-type lectin-like molecule-1, CD33, epidermal growth factor receptor variant III (EGFRvIII), ganglioside G2 (GD2), ganglioside GD3, TNF receptor family member B cell maturation (BCMA), Tn antigen ((Tn Ag) or (GalNAcα-Ser/Thr)), prostate-specific membrane antigen (PSMA), Receptor tyrosine kinase-like orphan receptor 1 (ROR1), Fms-Like Tyrosine Kinase 3 (FLT3), Tumor-associated glycoprotein 72 (TAG72), CD38, CD44v6, Carcinoembryonic antigen (CEA), Epithelial cell adhesion molecule (EPCAM), B7H3 (CD276), KIT (CD117), Interleukin-13 receptor subunit alpha-2, mesothelin, Interleukin 11 receptor alpha (IL-11Ra), prostate stem cell antigen (PSCA), Protease Serine 21, vascular endothelial growth factor receptor 2 (VEGFR2), Lewis(Y) antigen, CD24, Platelet-derived growth factor receptor beta (PDGFR-beta), Stage-specific embryonic antigen-4 (SSEA-4), CD20, Folate receptor alpha, Receptor tyrosine-protein kinase ERBB2 (Her2/neu), Mucin 1, cell surface associated (MUC1), epidermal growth factor receptor (EGFR), neural cell adhesion molecule (NCAM), Prostase, prostatic acid phosphatase (PAP), elongation factor 2 mutated (ELF2M), Ephrin B2, fibroblast activation protein alpha (FAP), insulin-like growth factor 1 receptor (IGF-I receptor), carbonic anhydrase IX (CAIX), Proteasome (Prosome, Macropain) Subunit, Beta Type, 9 (LMP2), glycoprotein 100 (gp100), oncogene fusion protein consisting of breakpoint cluster region (BCR) and Abelson murine leukemia viral oncogene homolog 1 (Abl) (bcr-abl), tyrosinase, ephrin type-A receptor 2 (EphA2), Fucosyl GM1, sialyl Lewis adhesion molecule (sLe), ganglioside GM3, transglutaminase 5 (TGS5), high molecular weight-melanoma-associated antigen (HMWMAA), o-acetyl-GD2 ganglioside (OAcGD2), Folate receptor beta, tumor endothelial marker 1 (TEM1/CD248), tumor endothelial marker 7-related (TEM7R), claudin 6 (CLDN6), thyroid stimulating hormone receptor (TSHR), G protein-coupled receptor class C group 5, member D (GPRC5D), chromosome X open reading frame 61 (CXORF61), CD97, CD179a, anaplastic lymphoma kinase (ALK), Polysialic acid, placenta-specific 1 (PLAC1), hexasaccharide portion of globoH glycoceramide (GloboH), mammary gland differentiation antigen (NY-BR-1), uroplakin 2 (UPK2), Hepatitis A virus cellular receptor 1 (HAVCR1), adrenoceptor beta 3 (ADRB3), pannexin 3 (PANX3), G protein-coupled receptor 20 (GPR20), lymphocyte antigen 6 complex, locus K 9 (LY6K), Olfactory receptor 51E2 (OR51E2), TCR Gamma Alternate Reading Frame Protein (TARP), Wilms tumor protein (WT1), Cancer/testis antigen 1 (NY-ESO-1), Cancer/testis antigen 2 (LAGE-1a), Melanoma-associated antigen 1 (MAGE-A1), ETS translocation-variant gene 6, located on chromosome 12p (ETV6-AML), sperm protein 17 (SPA17), X Antigen Family, Member 1A (XAGE1), angiopoietin-binding cell surface receptor 2 (Tie 2), melanoma cancer testis antigen-1 (MAD-CT-1), melanoma cancer testis antigen-2 (MAD-CT-2), Fos-related antigen 1, tumor protein p53 (p53), p53 mutant, prostein, surviving, telomerase, prostate carcinoma tumor antigen-1, melanoma antigen recognized by T cells 1, Rat sarcoma (Ras) mutant, human Telomerase reverse transcriptase (hTERT), sarcoma translocation breakpoints, melanoma inhibitor of apoptosis (ML-IAP), ERG (transmembrane protease, serine 2 (TMPRSS2) ETS fusion gene), N-Acetyl glucosaminyl-transferase V (NA17), paired box protein Pax-3 (PAX3), Androgen receptor, Cyclin B1, v-myc avian myelocytomatosis viral oncogene neuroblastoma derived homolog (MYCN), Ras Homolog Family Member C (RhoC), Tyrosinase-related protein 2 (TRP-2), Cytochrome P450 1B1 (CYP1B1), CCCTC-Binding Factor (Zinc Finger Protein)-Like, Squamous Cell Carcinoma Antigen Recognized By T Cells 3 (SART3), Paired box protein Pax-5 (PAX5), proacrosin binding protein sp32 (OY-TES1), lymphocyte-specific protein tyrosine kinase (LCK), A kinase anchor protein 4 (AKAP-4), synovial sarcoma, X breakpoint 2 (SSX2), Receptor for Advanced Glycation Endproducts (RAGE-1), renal ubiquitous 1 (RU1), renal ubiquitous 2 (RU2), legumain, human papilloma virus E6 (HPV E6), human papilloma virus E7 (HPV E7), intestinal carboxyl esterase, heat shock protein 70-2 mutated (mut hsp70-2), CD79a, CD79b, CD72, Leukocyte-associated immunoglobulin-like receptor 1 (LAIR1), Fc fragment of IgA receptor (FCAR or CD89), Leukocyte immunoglobulin-like receptor subfamily A member 2 (LILRA2), CD300 molecule-like family member f (CD300LF), C-type lectin domain family 12 member A (CLEC12A), bone marrow stromal cell antigen 2 (BST2), EGF-like module-containing mucin-like hormone receptor-like 2 (EMR2), lymphocyte antigen 75 (LY75), Glypican-3 (GPC3), Fc receptor-like 5 (FCRL5), and immunoglobulin lambda-like polypeptide 1 (IGLL1).

Methods of Purifying Lentiviral Vectors

The methods of the invention include processes for purifying lentiviral vectors with improved efficiency, e.g., such that higher quantities of lentiviral vector are recovered relative to purification of lentiviral preparations containing conventional buffers (e.g., HEPES). For instance, the lentiviral vector preparations described herein can be purified by filtration (e.g., microfiltration or ultrafiltration) and/or by chromatography (e.g., size-exclusion chromatography) with high lentiviral recovery. Filtration techniques, such as those described above and known in the art, can be used so as to produce lentiviral preparations that are substantially free of microorganisms and cells (e.g., mammalian cells) from which the lentiviral vector is prepared. Additionally or alternatively, lentiviral vector preparations of the invention can be treated with nucleases so as to produce a preparation that is substantially free of contaminating polynucleotides (e.g., non-lentiviral polynucleotides derived from the cell in which the lentiviral vector was produced, such as chromosomal mammalian DNA, human DNA, RNA, or other polynucleotides that are not included within the lentiviral transgene).

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1. Production of Lentiviral Vectors in Serum-Free Cell Culture

A GFP gene transfer vector, a packaging vector, a rev expression vector, and a VSV-G expression vector were generated. The gene transfer vector contains both cPPT and WPRE elements. In more detail, the lentiviral vector used in the study was self-inactivating transfer construct pELPS-EGFP, which is based on pRRL transfer construct (Dull et al., J. Virol. 72(11):8463-8471, 1998). pELPS-EGFP was constructed using pELPS-19-BBz (Milone et al., Mol. Ther. 17(8):1453-1464, 2009) by replacing CAR transgene with EGFP. Lentivirus was produced using third generation packaging system consisting of pMDLgpRRE, pRSV-Rev and pMD.G plasmids (Dull et al., supra), where ampicillin resistance gene was substituted with kanamycin resistance neomycin phosphotransferase II.

The viral production is done at 10 liter scale. The reagents needed to generate 10 liters of supernatant are described below. Expi293F (Life Technologies) cells were seeded at a cell density of $5$-$6\times10^6$ cells/ml with 96% viability, containing Freestyle medium (Life Technologies) without serum. 12.5 ml PEIpro (Polyplus) was added to 0.25 liter of medium and added slowly to the plasmid mix (12.8 mgs of plasmids in 0.25 liter). After 15 minutes of incubation, 0.5 liter transfection mix is split between 2×5 liter flasks with addition of another 2.25 liter of FreeStyle media per flask. After 24 hours of incubation, cells were centrifuged at 2000 RPM for 5 minutes, and supernatant was discarded. This is followed by addition of pH 6 media (FreeStyle media, pH adjusted) with 8 mM of sodium-butyrate (Sigma). At 48 hours of transfection, the cells were centrifuged at 2000 rpm for 5 minutes, and supernatant is saved for purification (Harvest 1). Another 2.5 liters of pH 6.0 media were added to each of the shake flasks for incubation in a rotatory shaker (Infors HT incubator, shake speed 100 RPM, 8% $CO_2$, 37° C.). The second harvest (harvest 2) is collected at 72 hours, followed by low speed centrifugation. The 48 and 72 hour harvests were pooled and processed for further purification. The partially pooled material is stored at 4° C., if required.

For one 2×2.5 liters medium, 6 µg of GFP gene transfer vector, 3 µg of the packaging vector, 3 µg of rev expression vector, and 0.75 µg of VSVG expression vector were used. Once the transfection mixture is added to cells, shake flasks were carefully shaken to achieve uniform mixing. This is followed by incubation of cells as described above.

Example 2. Purification of Lentiviral Vectors Produced in Serum-Free Cell Culture The 48 and 72 hour partially centrifuged harvest is passed through three differential graded filters, 5 micron glass filter (GE Healthcare), 1.2 micron Polypropylene filter (Sartorius), and 0.6/0.2 micron Polyethersulfone filter (GE Healthcare). The filtration train removes producer cells, cell debris and organelles. This is followed by tangential flow filtration using 500 MWCO hollow fiber membranes (GE Healthcare) for 100 fold concentration of virus containing supernatant. Benzonase (EMD-Millipore) treatment was performed at room temperature for 30 minutes with 50 units/ml followed by centrifugation at 3000 RPM for 20 minutes. A white pellet is visible, but there is minimal loss (<5%) of virus particles in the supernatant. A size-exclusion chromatography is performed using PIPES and other buffers (showing high stability of vectors described in this invention), which follows sterile filtration using 0.2 micron filters (EMD Millipore).

Example 3. Sample Preparation for High-Throughput Screening of Stability of Lentiviral Preparations ZEBA™ spin desalting plates (7K MWCO, Life Technologies) were buffer exchanged 4× times with 250 µl of specific buffers and salts. 100 µl of virus stock solution was loaded at each well followed by centrifugation at 1000×g for 2 minutes. No loss of volume is observed post buffer exchange. 20-100 µl was used for each of the analytics (DLS, infectivity and freeze/thaw studies). To study the effect of temperature on infectivity of vectors, temperature shock was carried out in 96 well thin-walled PCR plates in a C-1000 Touch Thermal Cycler (range 25 to 55° C. for an hour).

Example 4. Analysis of Lentiviral Aggregation by Dynamic Light Scattering in High-Throughput Screens 20 µl of purified recombinant lentiviral vector ($10^6$-$10^7$ TU/ml) was pipetted in a 384 well plate (Black polystyrene base, hydrophilic plate, Greiner Bio). The plate is centrifuged to remove trapped air bubbles at 2000 RPM for 3 minutes at room temperature, followed by sealing with Microseal 'B' seal (Bio-Rad). It is placed in DynaPro plate reader (Wyatt Technology Corporation, CA, USA) equipped with an 830 nm laser and a temperature control module. The Dynamics® software (Version 7.1.8.93, Wyatt Technology Corporation) was used for scheduled data acquisition and analysis. Five 5-second measurements were taken for each well. A single, sealed 384 well plate is measured at 25° C., followed by incubation at 37° C. for 2 hours, and measured as described. The same procedure is repeated for 42° C., 50° C., and 55° C. Regularization analysis was performed using algorithm bundled with the Dynamics® software. The upper and lower correlation function cut off were 0.5 and $1\times10^6$ µs, respectively. The hydrodynamic radius of the lentiviral peak is assigned as 50-200 nm.

Example 5. Determination of Lentiviral Titer in High-Throughput Screens

The titer of lentiviral vector includes a functional titer calculated by the number of cells expressing GFP protein coded by the carried gene (TU/ml). HEK293T cells were seeded at a certain density ($2\times10^4$/well) in a 96 well plate (Corning, Flat bottom) at a volume of 50 µl of D-MEM medium (Life Technologies) containing 10% fetal bovine serum (Life Technologies) and 8 µg/ml Polybrene (EMD Millipore). Diluted GFP standard virus and samples are prepared in complete DMEM and are added (50 µl) to the cells.

10 fold serial dilutions of virus solutions were prepared in a dilution series with DMEM as the diluent. The 96 well plates were incubated in a $CO_2$ incubator at 37° C. for 72 hours. The cells were treated with trypsin followed by addition of 200 µl of complete DMEM. The plate was centrifuged at 1000 RPM for 10 minutes and the media is exchanged with 200 µl of flow-buffer autoMACS running buffer, Miltenyi Biotec). This is followed by GFP analysis done in Guava Viacount (EMD Millipore). Cell counting and health of untransduced cells were monitored at the time of harvest.

Example 6. Analysis of Lentiviral Stability after Repetitive Freeze/Thaw Cycles To address loss of infectivity with repeated freeze/thaw cycles, small aliquots (~100 μl) of lentiviral vectors were frozen at −80° C. for 20 minutes, followed by a thawing slowly at room temperature for 20 minutes (representing a worst case scenario). The freeze/thaw cycles were performed for 3, 6, 9 cycles and vector activity is compared to the control. Trend analysis is done using Spotfire where a high value signifies preservation of activity of lentiviral vectors.

Example 7. Determination of Lentiviral Titer in Primary T-Cells

Vials containing PBMC from three healthy donors were thawed, centrifuged, and resuspended in X-Vivo medium (Lonza) supplemented with 2% human AB serum (Access) and IL-2 (Prometheus Ther.). Cells were counted and seeded at a density of $1.6\times10^6$ cells/ml in 100 μL in duplicates for each donor. Anti-CD3/CD28 beads (Life Technologies) were washed in X-vivo Simple Medium and added at a final bead density of $4.8\times10^5$ beads/well. Cells were placed in incubator at 37° C. at 5% $CO_2$.

Lentiviral vector aliquots were thawed at room temperature and serial dilutions were prepared in a 1:3 dilution fashion in X-Vivo medium. Vector aliquots used were GFP (stock 26Sept14, JDG, 250 μL), Lentigen (Lentigen Corp, hCART019, LN0127-0214-064), and four different formulations of a GFP vector as follows: AD1 (20 mM His, 100 mM NaCl, 2.5% sucrose pH6.5), AD2 (20 mM Citrate, 75 mM NaCl, 2.5% sucrose pH 6.5), AD3 (20 mM HEPES, 75 mM NaCl, 2.5% Sucrose, pH 7), and AD4 (20 mM PIPES, 75 mM NaCl, 2.5% Sucrose, pH 6.5).

Cells were split 1:3 on day 3 by resuspending cells and adding 60 μL of cell suspension into 120 μL of X-vivo Simple Medium in corresponding wells of new plate. Cells were returned to the incubator. Cells were split again on day 5 in 1:2 into new plates (90 μL of cells into 110 μL of X-Vivo Simple Medium) and returned to the incubator.

Cells from each plate were pooled; an aliquot was debeaded by placing cell suspension on magnet and taking supernatant and counting on Guava Viacount solution at a 1:10 dilution. Then, 200 μL of cells were spun down at 1000 rpm for 5 minutes at 20° C. and resuspended in 200 μL of AutoMacs buffer (Miltenyi), transferred to a new U-bottom 96-well plate and GFP fluorescence measured using Guava instrument (Millipore). The percent of GFP transduced cells was calculated. Cells transduced with Lentigen Vector, were spun down at 1000 rpm for 5 minutes at 20° C. and stained using a mixture of AutoMacs buffer and PE-labeled anti-idiotype antibody at a 1:160 dilution (with one well left unstained). The preparation was left in the dark at room temperature and washed twice in 200 μL of AutoMacs buffer. Cells were resuspended in 200 μL of AutoMacs buffer and monitored using Guava instrument. Titers as TU/mL for both GFP and Lentigen were calculated based on the formula: Cells at D0*(% transduced cells/100)/virus volume (mL).

Example 8. Summary of Experimental Results—Stability Studies

Screening studies were carried out using a parallel approach (FIG. 1) to identify conditions that can be used to stabilize lentiviral vectors. The stability of a commercially available lentiviral vector (Lentigen) was assessed in a screen varying buffer, pH, and salt conditions, as indicated in FIG. 2. The lentiviral vector was incubated overnight (about 18 hours) at room temperature (about 25° C.). Stability was determined by assessment of titer (TU/ml) using the method described in Example 5, above. PIPES buffer with NaCl stabilized the vector almost to the same extent as the control formulation (Lentigen Formulation), which may include excipients in addition to buffer and salt components. The lentiviral vector used in this experiment was CAR19 LV from Lentigen. All other studies described in this Example utilized the GFP-LV described in Example 1, above.

Hydrodynamic radius distributions of various formulations were determined to assess levels of lentivirus vector aggregation (FIG. 3), using methods described in Example 4, above.

FIG. 4 shows that histidine buffer (20 mM histidine, 50-150 mM NaCl, pH 6.0, 6.5, and 7.0) has a very low tendency for lentiviral vector aggregation with increase in temperature (monitored by change in Rh). FIG. 5 shows that lentiviral vector in 20 mM PIPES, pH 6.5 with NaCl concentrations ranging from 50-150 mM, showed no tendency for aggregation at all temperatures (with the exception of 100 mM NaCl at 55° C.). Also, lentiviral vector in 20 mM PIPES, pH 7.0 with NaCl ranging from 50-150 mM, showed aggregation tendencies at temperatures 42-55° C. FIG. 6 shows that citrate buffer (20 mM citrate, 50-150 mM NaCl, pH 6.0, 6.5) has a very low tendency for lentiviral vector aggregation with increases in temperature (monitored by change in Rh). FIG. 7 shows that HEPES buffer (20 mM HEPES, 50-150 mM NaCl, pH 7.0, 7.5 and 8.0) has large aggregation propensities at pH 7.5 and 8.0, whereas pH 7.0 preserves monomeric virus at different temperatures. FIG. 8 shows that MOPS buffer (20 mM MOPS, 50-150 mM NaCl, pH 6.5, 7.0 and 7.5) has high aggregation propensity at pH 6.5 and 7.0 at 50 mM NaCl and all conditions at pH 7.5. Only 20 mM MOPS, 75 mM NaCl, pH 6.5 shows aggregation at high temperature (55° C., which is significantly high as the virus would never be exposed to such a temperature in a real case situation). FIG. 9 shows that MES buffer (20 mM MES, 50-150 mM NaCl, pH 6.0 and 6.5) has low aggregation propensity of lentivirus vector under these conditions. FIG. 10 shows that phosphate buffer (20 mM phosphate, 50-150 mM NaCl, pH 6.5, 7.0, 7.5, 8.0) has low aggregation propensity of lentivirus vector at pH 6.5; all other pH conditions have higher aggregation propensity. FIG. 11 shows that for HEPPS buffer (20 mM HEPPS, 50-150 mM NaCl, pH 7.5 and 8.0), all of the conditions promote aggregation of LV (except at 25° C.). FIG. 12 shows that for Tris buffer (20 mM Tris, 50-150 mM NaCl, pH 7.5 and 8.0), all of the conditions promote aggregation of LV (except at 25° C.).

These results show that improved stability of a lentiviral vector can be obtained in histidine, citrate, MOPS, PIPES, and MES buffers. DLS was used to measure hydrodynamic radius of the lentiviral particles. Because DLS is a semi-quantitative assay, we relied on the trend analysis on aggregation at different temperatures (low to high).

Additional analysis was carried out to determine the robustness of Rh in different buffer conditions (FIGS. 13-19). The analyses included DLS (see, e.g., Example 4, above) and determination of titer (see Example 5, above). FIG. 13 shows that histidine, citrate, MOPS, PIPES, HEPES, and MES buffers selectively promote stability to lentiviral vector in stabilizing monomers, as assessed by DLS only. FIG. 14 shows that phosphate, HEPPS, and Tris based buffers do not offer any protective action from aggregation at high temperature, as assessed by DLS only.

FIGS. 15-19 show the results of studies in which two criteria (protection from aggregation and protection from loss of infectivity at high temperatures) are analyzed together. FIG. 15 shows that histidine and PIPES buffers provide stability even at high temperatures in preserving infectivity (with unique pH and salt combinations). FIG. 16 shows that citrate buffer provides protection from loss of infectivity as compared to HEPES at high temperatures, while FIG. 17 shows that MOPS and MES buffers provide protection from loss of infectivity at high temperatures. FIG. 18 shows that phosphate buffer provides protection from loss of infectivity as compared to HEPPS at high temperatures, while FIG. 19 shows that Tris buffer does not provide protection from loss of infectivity at high temperatures. These results show that selected buffers (e.g., histidine, PIPES, citrate etc.) have significant stabilizing effects in preserving infectivity and monomers, as determined by two orthogonal analytical techniques.

Freeze-thaw studies were carried out to further assess stability. The methods used are described in Example 6, above. FIG. 20 shows the number of conditions under which lentiviral vectors survived three, six, and nine freeze-thaw cycles, with greater than 65% retention of titer. FIG. 21 shows that inactivation kinetics of lentiviral vectors from third, sixth, and ninth freeze-thaw cycles differentiated buffers providing high or low stability for the vectors. Analysis of the data (see, e.g., FIG. 22) identified five conditions under which lentiviral vectors survived nine freeze-thaw cycles with greater than 65% retention of titer. The details of these conditions are set forth in FIG. 23.

Additional studies were carried out to assess the effects of including a carbohydrate, sucrose, on maintenance of stability after multiple freeze-thaw cycles. The methods of Example 6, above, were employed for these experiments. For citrate, HEPES, and PIPES-based buffers, there is no loss of activity of lentivirus vectors, as compared to histidine buffer, which shows about 20% loss of activity after the ninth freeze-thaw cycle (see FIGS. 24 and 25). Examples of selected stabilizing buffer conditions with carbohydrate are shown in FIG. 26.

Viral titers were assessed in primary T cells, using the methods described in Example 7, above. The results are set forth in FIG. 27. PIPES and citrate buffers were found to provide very high titer in primary cells, showing efficient transduction in cells. HEPES and histidine buffers provided high titers as well. All of the identified conditions outperformed commercial vector purchased from Lentigen Corp. (commercial formulation, unknown).

A comparison of certain results of the stability studies using PIPES, HEPES, and histidine buffers is set forth in FIG. 28. The aggregation results show an increase in lentivirus vector hydrodynamic radius as a function of temperature, as measured by DLS. Average values with a specific pH is shown (with 50-150 mM NaCl). The activity of lentivirus vector at high temperature was assessed in 293T cells. The values at 50° C. were compared to values at 25° C. Average values with a specific pH are shown (with 50-150 mM NaCl). Activity of a lentivirus vector in 293T cells after the ninth freeze-thaw cycle is shown as an example to indicate lentivirus vector stability (>100% activity meaning no loss of activity; the assay being variable as an in vivo assay). Activity of lentivirus vector in primary T cells is shown as an additional test for transduction ability. Lentiviral vector in PIPES buffer was able to transfect ~25% and ~35% more primary T cells, as compared to lentiviral vector in HEPES and histidine buffer, respectively. PIPES buffer thus provides an alternative to the standard HEPES-based formulation because, for example, lentiviral vectors are more stable in PIPES buffer. Furthermore, lentiviral vectors in PIPES buffer were able to transfect ~20-25% more primary T cells as compared to HEPES and histidine buffers Example 9. Purification of Lentiviral Vectors in PIPES, Histidine, and HEPES Buffers Lentiviral vectors were produced and purified using the methods described in Examples 1 and 2, above. A post chromatographic purification step, involving passage through a 0.2 micron filter, is carried out to maintain sterility. As low recovery can result from purification, due to aggregation, different buffers were tested to identify conditions the result in optimal recovery. As shown in FIG. 29, PIPES buffer showed better recovery, as compared to HEPES and histidine buffers.

Example 10. Stabilization of Additional Lentiviral Vectors

As noted above, the studies carried out above were carried out using a GFP lentiviral vectors (except for the stability studies illustrated in FIG. 2, as noted above). We carried out additional experiments, which show that a PIPES-based buffer (20 mM PIPES, pH 6.5, 75 mM NaCl, 2.5% sucrose) is effective at stabilizing two additional lentiviral vectors (vectors 1 and 2) expressing a different transgene.

Two lentiviral vectors, present in a PIPES-based buffer (20 mM PIPES, pH 6.5, 75 mM NaCl, 2.5% sucrose) were purified using a method including the steps of microfiltration, tangential flow filtration (TFF), benzonase treatment, centrifugation, size exclusion chromatography (SEC), and sterile filtration. Samples were obtained from the TFF retentate and held for 4 days at −80° C. or +4° C. In addition, samples were obtained from the SEC eluate and held for 3 days at −80° C. or +4° C. Viral titers were obtained from the samples before and after the holding periods. Both vectors were stable in the PIPES buffer during purification. As shown in FIG. 30, no significant changes in activity, as measured by titer determinations, were found during short-term storage of the TFF and SEC samples at −80° C. or +4° C.

Dynamic light scattering was used to assess the aggregation status of the vectors stored in PIPES buffer (20 mM PIPES, pH 6.5, 75 mM NaCl, 2.5% sucrose). As shown in FIGS. 31 and 32, both vectors were found to be monomeric in the PIPES formulation at 25° C., with the determined d,nm being around 140 nm. The methods used are as described in Example 4, above.

Stability of purified vector 2 was assessed after storage in PIPES buffer (20 mM PIPES, pH 6.5, 75 mM NaCl, 2.5% sucrose) at 4° C. for three weeks. As shown in FIG. 33, this vector maintains high stability under these conditions, as measured by determination of titers in 293T cells, as well as percentage of activity remaining compared to a control (4° C., Day 0; the first bar in FIG. 33, activity of control is taken as 100%). The x-axis bars show activities on Days 14 and 21, respectively (expressed as percent vs. control).

In further studies, freeze-thaw stability of vector 2 in PIPES buffer (20 mM PIPES, pH 6.5, 75 mM NaCl, 2.5% sucrose) was assessed (see Example 6, above, for methods). As shown in FIG. 34, this vector maintains high stability after multiple cycles of freeze-thaw (up to 9 cycles were carried out), as measured by determination of titers in 293T cells, as well as percentage of activity remaining compared to a control (titer after 1 freeze-thaw cycle, as purified lentiviral sample is stored at −80° C. immediately after purification). The activity of the control sample is taken as 100%, represented in the first bar in FIG. 34. The x-axis bars show residual activities (in percent) after 3, 6, and 9 freeze-thaw cycles (expressed as percent vs. control).

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

The invention claimed is:

1. An aqueous composition comprising a lentiviral vector, a 1,4-piperazinediethanesulfonic acid (PIPES) buffer, and a salt, wherein the lentiviral vector comprises a transgene encoding a chimeric antigen receptor (CAR), which comprises, in an N-terminal to C-terminal direction, an antigen binding domain, a transmembrane domain, and one or more signaling domains.

2. The aqueous composition of claim 1, wherein said PIPES buffer is present at a concentration of from about 10 mM to about 50 mM.

3. The aqueous composition of claim 1, wherein the pH of said aqueous composition is from about 6.0 to about 7.0.

4. The aqueous composition of claim 1, wherein said salt is selected from the group consisting of sodium chloride, magnesium chloride, and calcium chloride.

5. The aqueous composition of claim 1, wherein the concentration of said salt in said aqueous composition is from about 25 mM to about 150 mM.

6. The aqueous composition of claim 1, wherein said aqueous composition comprises 20 mM PIPES and 75 mM sodium chloride, and said aqueous composition has a pH of about 6.5.

7. The aqueous composition of claim 1, wherein said aqueous composition further comprises a carbohydrate, which is optionally a non-reducing carbohydrate, and is optionally present at a concentration of from about 1% to about 10% by weight per volume of said composition.

8. The aqueous composition of claim 7, wherein the aqueous composition comprises said non-reducing carbohydrate, which is selected from the group consisting of sucrose and trehalose.

9. The aqueous composition of claim 1, wherein said aqueous composition comprises 20 mM PIPES, 75 mM sodium chloride, and 2.5% sucrose by weight per volume of said aqueous composition, and said aqueous composition has a pH of about 6.5.

10. The aqueous composition of claim 1, wherein the osmolality of said aqueous composition is from about 270 mOsm/kg to about 330 mOsm/kg.

11. The aqueous composition of claim 1, wherein said lentiviral vector is present at a concentration of from about $2\times10^8$ transducing units per milliliter (TU/mL) to about $1\times10^9$ TU/mL.

12. The aqueous composition of claim 1, wherein said lentiviral vector is a recombinant human immunodeficiency virus.

13. The aqueous composition of claim 1, wherein one of said one or more signaling domains comprises a primary signaling domain comprising a CD3-zeta stimulatory domain.

14. The aqueous composition of claim 1, wherein one or more of said one or more signaling domains comprises a costimulatory domain comprising an intracellular domain of a costimulatory protein selected from the group consisting of CD27, CD28, 4-1 BB (CD137), OX40, GITR, CD30, CD40, ICOS, BAFFR, HVEM, ICAM-1, lymphocyte function-associated antigen-1 (LFA-1), CD2, CDS, CD7, CD287, LIGHT, NKG2C, NKG2D, SLAMF7, NKp80, NKp30, NKp44, NKp46, CD160, B7-H3, and a ligand that specifically binds with CD83.

15. The aqueous composition of claim 1, wherein said antigen binding domain is an scFv.

16. The aqueous composition of claim 1, wherein said antigen binding domain binds to an antigen selected from the group consisting of CD19; CD123; CD22; CD30; CD171; CS-1; C-type lectin-like molecule-1, CD33; epidermal growth factor receptor variant III (EGFRvIII); ganglioside G2 (GD2); ganglioside GD3; TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2; mesothelin; Interleukin 11 receptor alpha (IL-11 Ra); prostate stem cell antigen (PSCA); Protease Serine 21; vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3; transglutaminase 5 (TGS5); high molecular weight-melanoma-associated antigen (HMWMAA); o-acetyl-G D2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1, melanoma antigen recognized by T cells 1; Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TM-PRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like, Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

17. The aqueous composition of claim 1, wherein said CAR comprises an anti-CD19 antibody or an anti-CD19 scFV, a 4-1 BB (CD137) transmembrane domain, and a CD3-zeta signaling domain.

18. The aqueous composition of claim 1, wherein said aqueous composition is free of one or more proteins selected from the group consisting of human serum albumin (HSA), recombinant human serum albumin (rHSA), bovine serum albumin (BSA), and a lipoprotein, or said lentiviral vector is produced in cells cultured in the absence of serum.

19. The aqueous composition of claim 1, wherein said lentiviral vector (i) is characterized by a hydrodynamic radius of 100±25 nm as measured by dynamic light scattering (DLS), which is optionally maintained within a temperature range of from 25° C. to 55° C.; (ii) is characterized by a polydispersity of from 10% to 25%, which is optionally maintained within a temperature range of from 25° C. to 55° C., or (iii) maintains a concentration after 3 freeze/thaw cycles of from about 70% to about 100% relative to the concentration of said lentiviral vector in said aqueous composition prior to said freeze/thaw cycles, wherein each of said freeze/thaw cycles comprises freezing said aqueous composition and subsequently allowing said aqueous composition to thaw at room temperature.

20. An aqueous composition comprising a lentiviral vector, a buffer selected from the group consisting of a phosphate buffer, a sodium citrate buffer, a 2-(N-morpholino)ethanesulfonic acid (MES) buffer, a 3-morpholinopropane-1-sulfonic acid (MOPS) buffer, and a salt, wherein the lentiviral vector comprises a transgene encoding a chimeric antigen receptor (CAR), which comprises, in an N-terminal to C-terminal direction, an antigen binding domain, a transmembrane domain, and one or more signaling domains.

21. A method of purifying a lentiviral vector, said method comprising passing the aqueous composition comprising a lentiviral vector, a 1,4-piperazinediethanesulfonic acid (PIPES) buffer, and a salt through a filter or a material comprising a plurality of particles, or contacting the aqueous composition with a nuclease, thereby producing an aqueous composition that is substantially free of microorganisms.

22. A method of expressing a transgene in a cell, said method comprising contacting said cell with the aqueous composition comprising a lentiviral vector, a 1,4-piperazinediethanesulfonic acid (PIPES) buffer, and a salt.

23. A kit comprising the aqueous composition comprising a lentiviral vector, a 1,4-piperazinediethanesulfonic acid (PIPES) buffer, and a salt and a package insert or a reagent that can be used to culture a cell transduced with said lentiviral vector.

* * * * *

UNITED STATES PATENT AND TRADEMARK OFFICE
CERTIFICATE OF CORRECTION

PATENT NO. : 10,724,006 B2
APPLICATION NO. : 15/777290
DATED : July 28, 2020
INVENTOR(S) : Amitabha Deb et al.

Page 1 of 1

It is certified that error appears in the above-identified patent and that said Letters Patent is hereby corrected as shown below:

In the Specification

Column 4, Line 63, replace "Family MemberC" with --Family Member C--.

In the Claims

Column 24, Line 57, Claim 16 replace "o-acetyl-G D2" with --o-acetyl-GD2--.

Column 25, Line 49, Claim 17 replace "4-1 BB" with --4-1BB--.

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*